(12) United States Patent
Kriesell et al.

(10) Patent No.: US 6,394,980 B2
(45) Date of Patent: *May 28, 2002

(54) FLUID DELIVERY APPARATUS WITH FLOW INDICATOR AND VIAL FILL

(75) Inventors: Marshall S. Kriesell, St. Paul; Steven M. Arnold, Minnetonka; James Garrison, Minneapolis; Farhad Kazemzadeh, Bloomington; William Kuester, Blaine; Rolf Hogan, Brooklyn Center, all of MN (US)

(73) Assignee: Science Incorporated, Bloomington, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/767,665

(22) Filed: Jan. 22, 2001

Related U.S. Application Data

(63) Continuation of application No. 09/165,706, filed on Oct. 2, 1998, now Pat. No. 6,176,845, which is a continuation-in-part of application No. 08/768,663, filed on Dec. 18, 1996, now Pat. No. 5,840,071.

(51) Int. Cl.[7] ............................................. A61M 37/00
(52) U.S. Cl. ...................... 604/132; 604/153; 604/246
(58) Field of Search .............................. 604/30, 83, 85, 604/89, 90, 88, 132, 406, 133, 153, 246

(56) References Cited

U.S. PATENT DOCUMENTS

| | | | | |
|---|---|---|---|---|
| 4,058,123 A | * | 11/1977 | May | 128/278 |
| 5,005,604 A | * | 4/1991 | Aslanian | 137/556 |
| 6,176,845 B1 | * | 1/2001 | Kriesel et al. | 604/132 |

* cited by examiner

*Primary Examiner*—Brian L. Casler
*Assistant Examiner*—Jennifer Maynard
(74) *Attorney, Agent, or Firm*—James E. Brunton

(57) ABSTRACT

An apparatus for accurately infusing medicinal agents into an ambulatory patient at specific rates over extended periods of time. The apparatus is of a compact, low profile, laminate construction and includes an elastic distendable membrane, chamber having a fluid outlet. Disposed within the fluid chamber is a thin fluid permeable member which precisely controls the rate of fluid flow through the fluid outlet. The apparatus also includes a highly novel fluid flow indicator that provides a readily discernible visible indication of fluid flow through the apparatus. Additionally, the apparatus includes a fill assembly comprising a prefilled vial that can be used to fill the fluid reservoir of the device with a selected medicinal fluid.

6 Claims, 43 Drawing Sheets

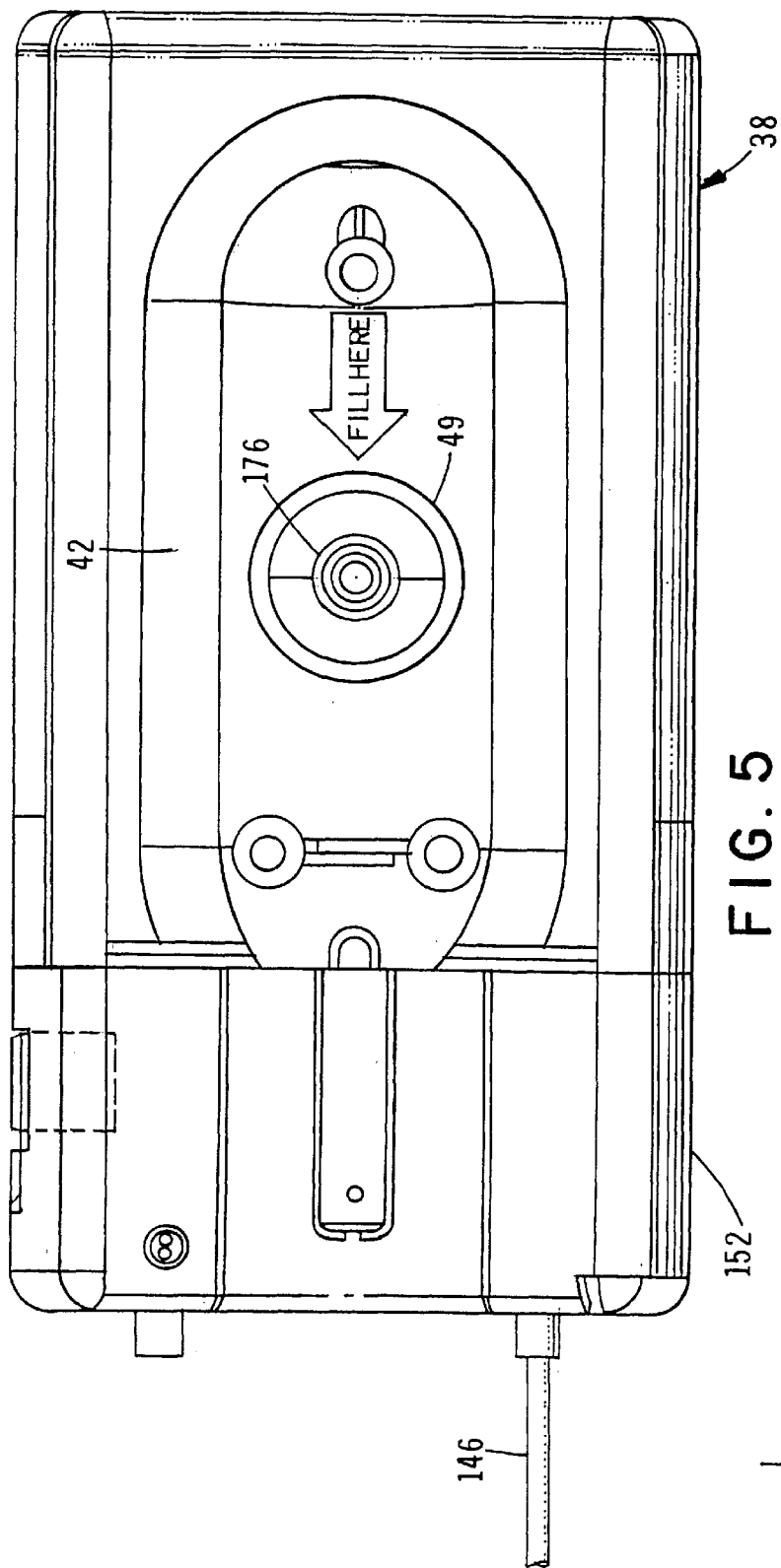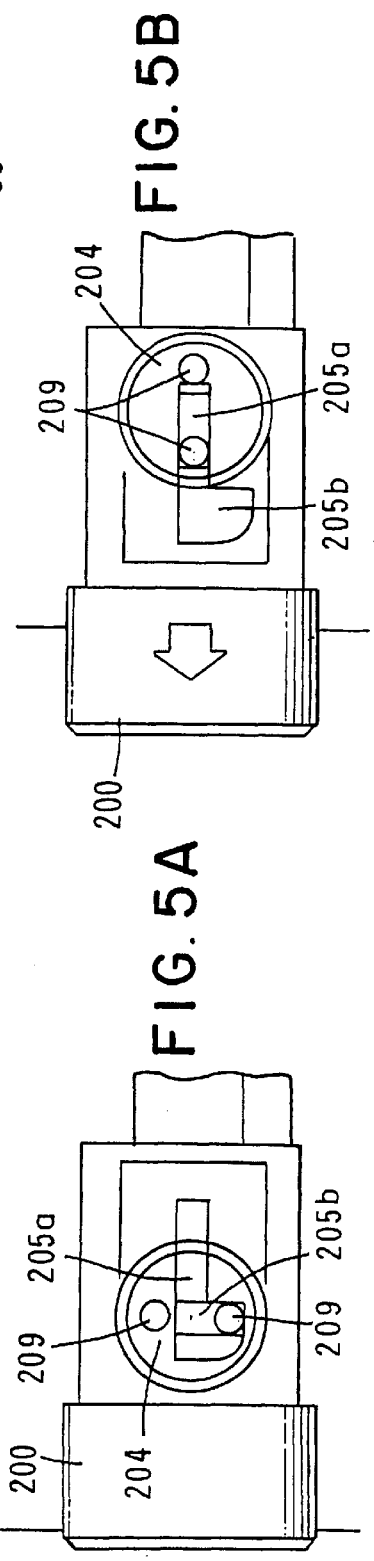

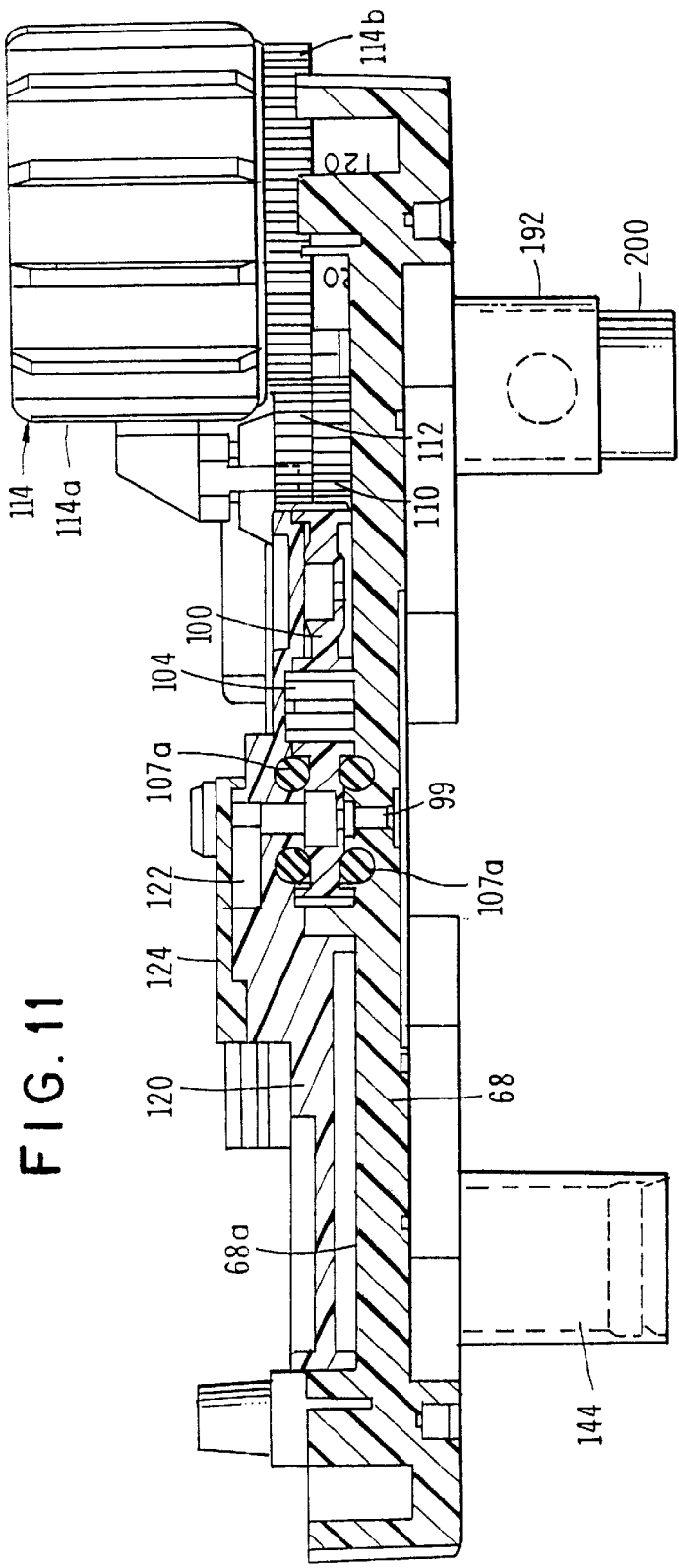
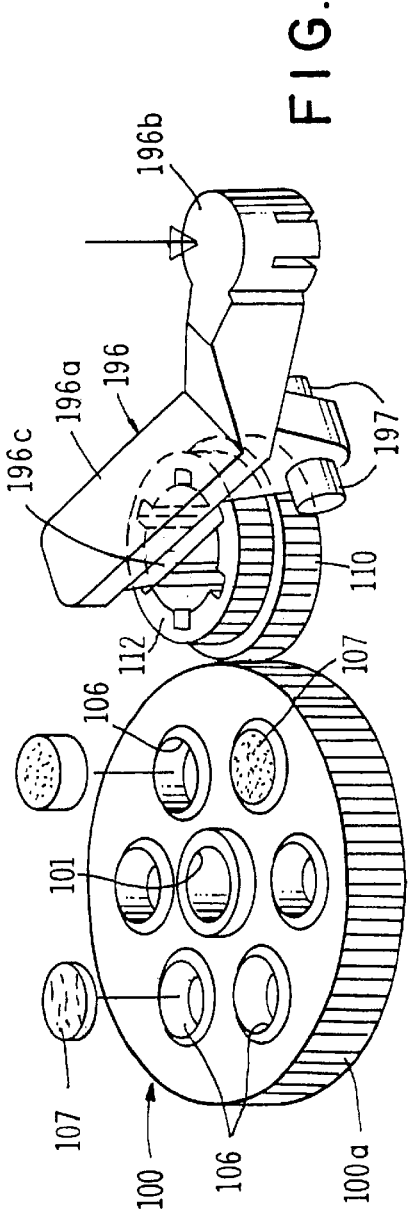
FIG. 11
FIG. 11A

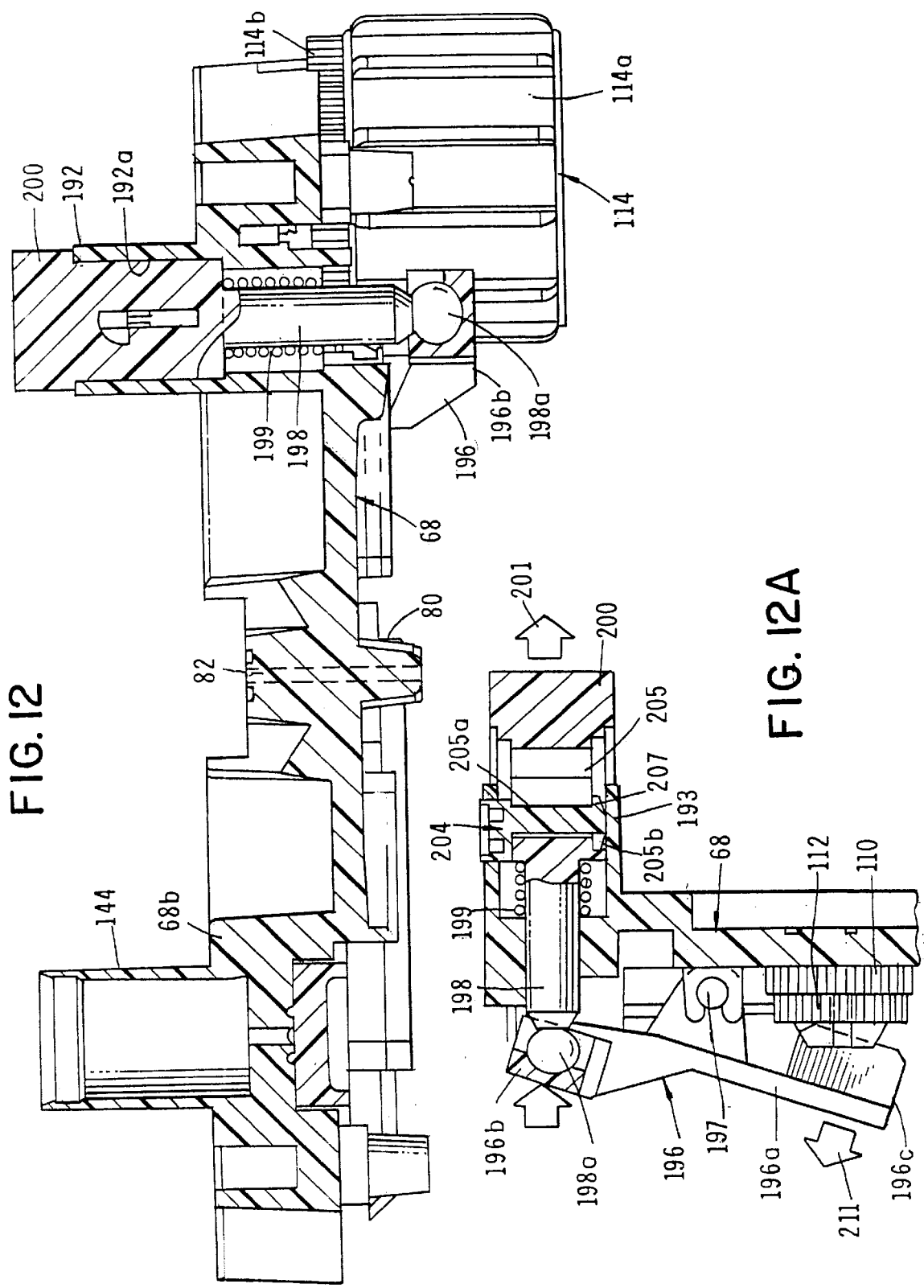

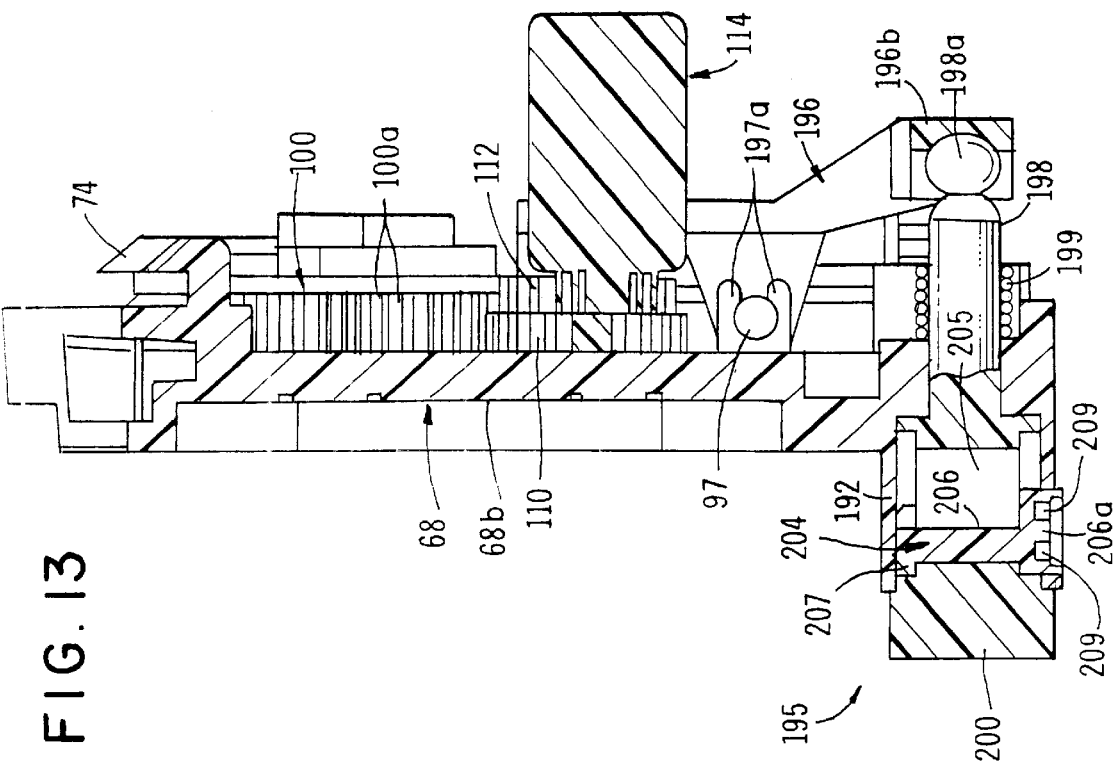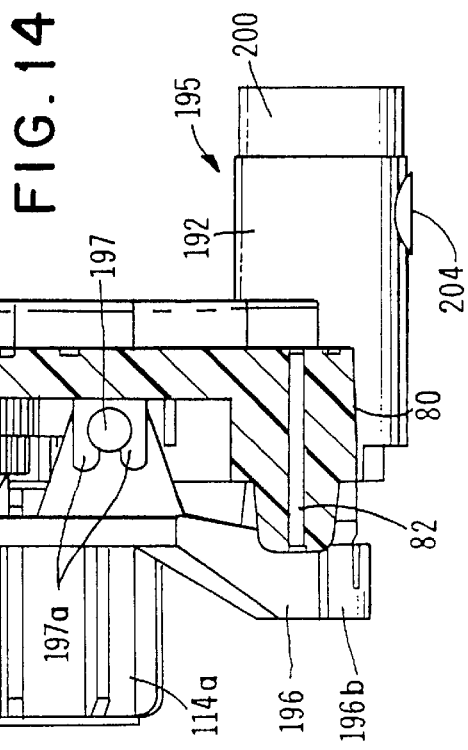

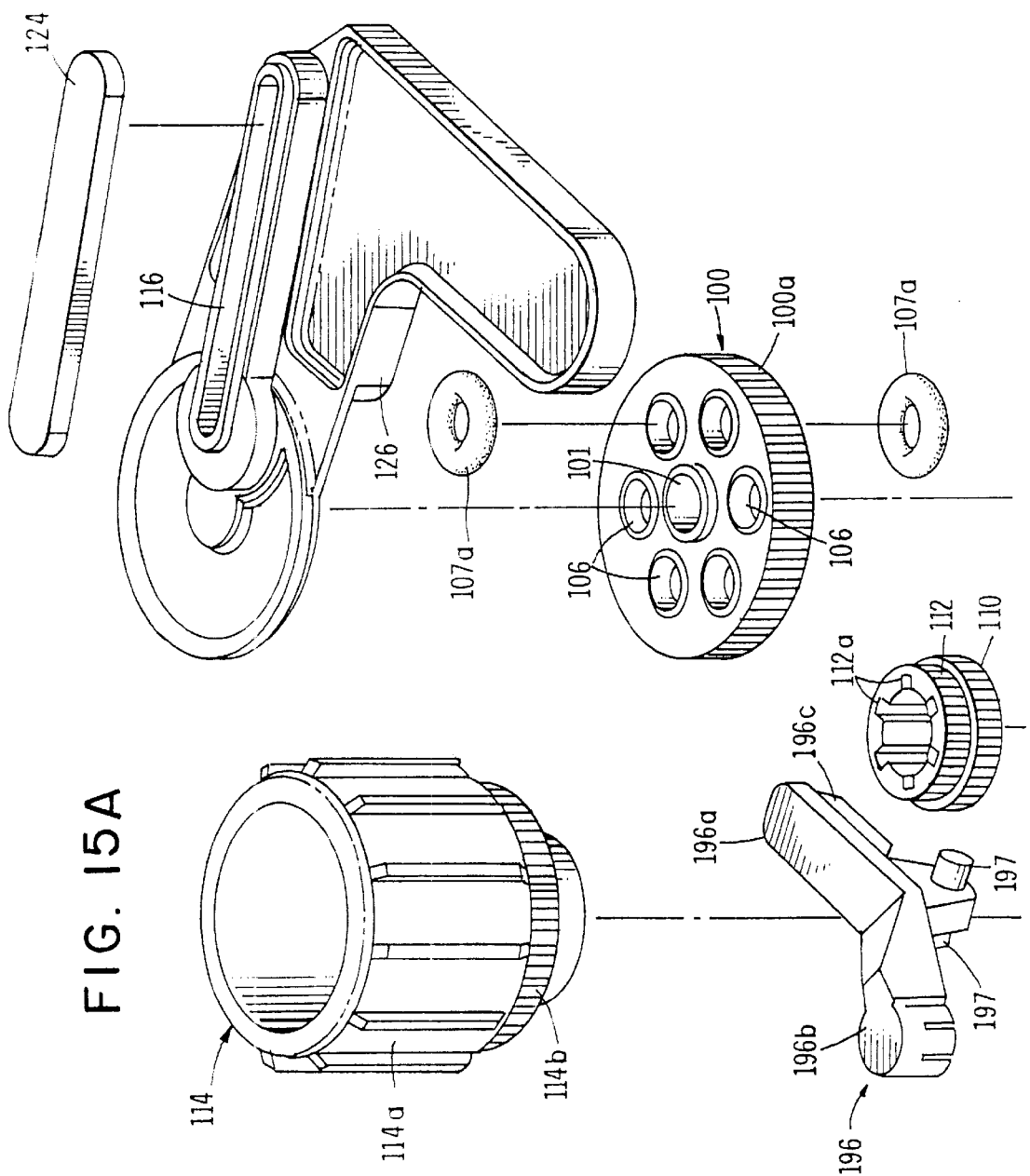

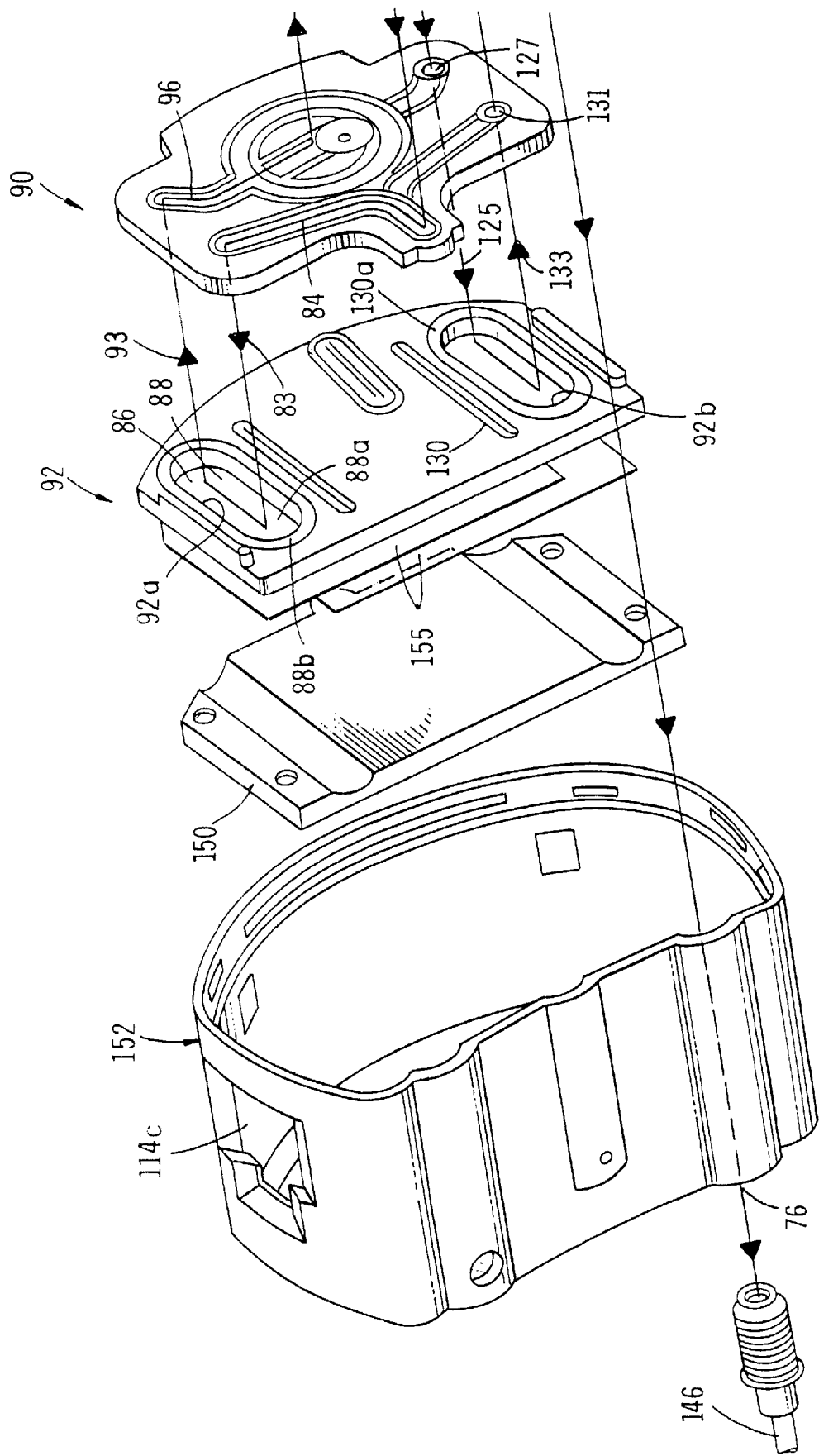

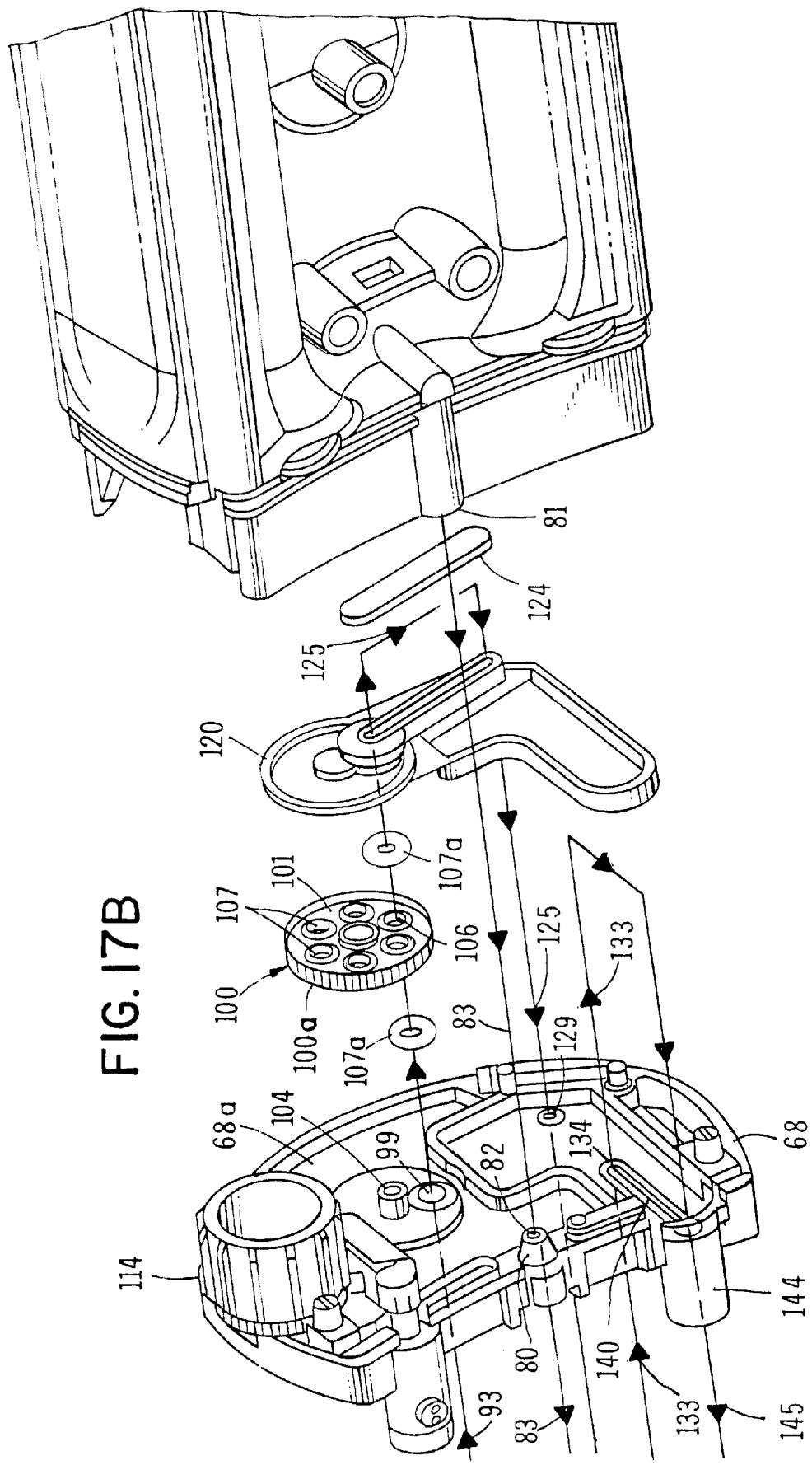

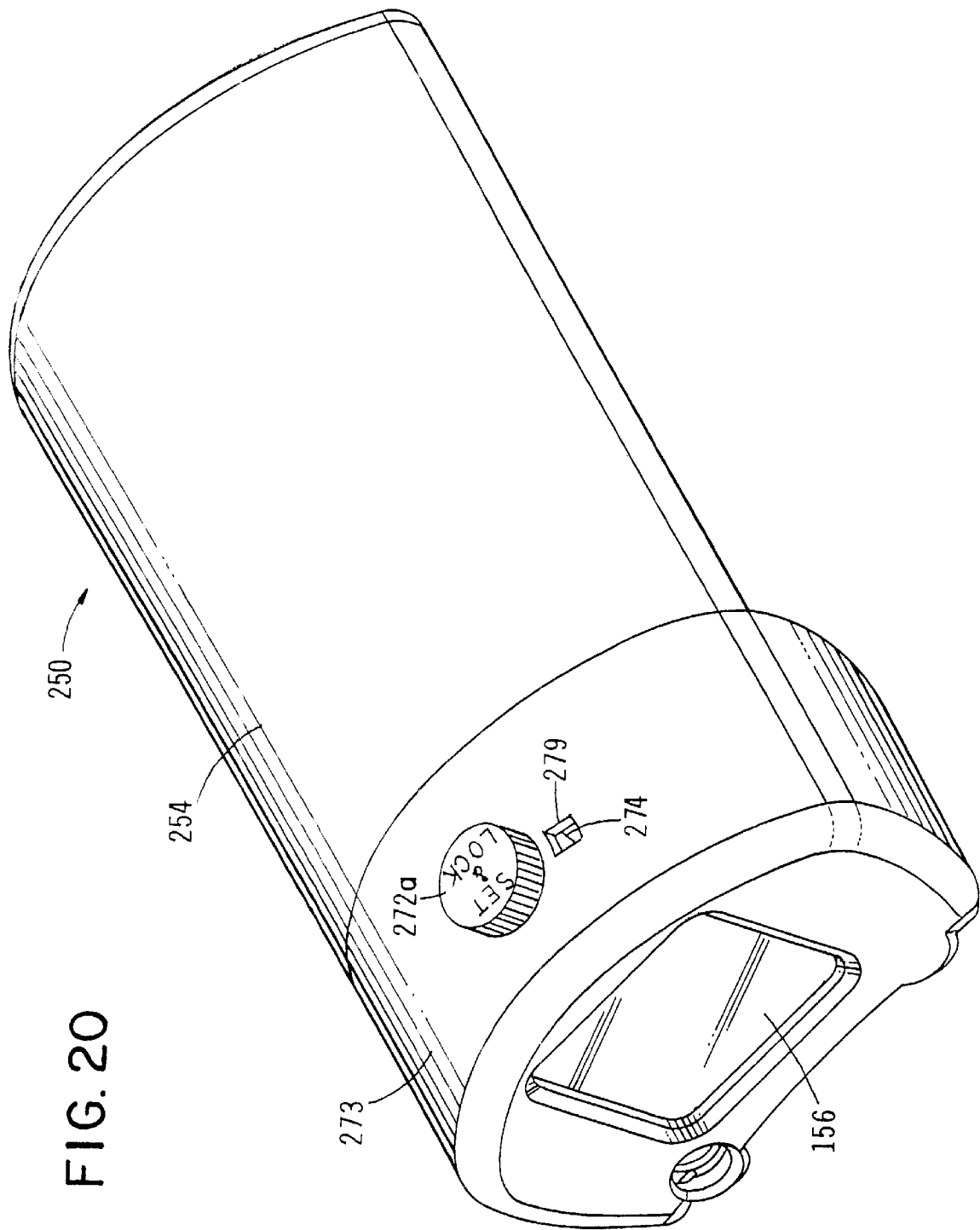

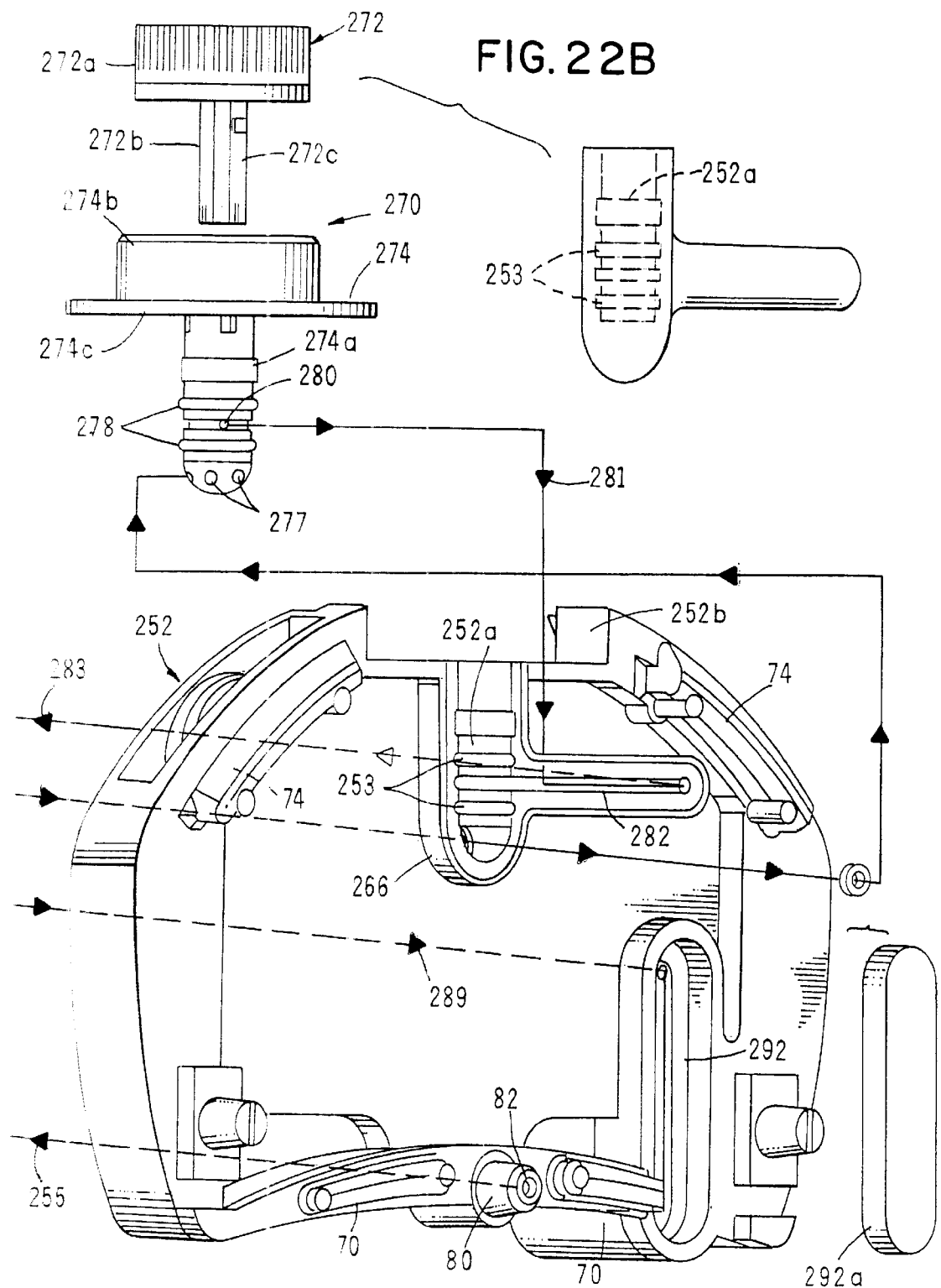

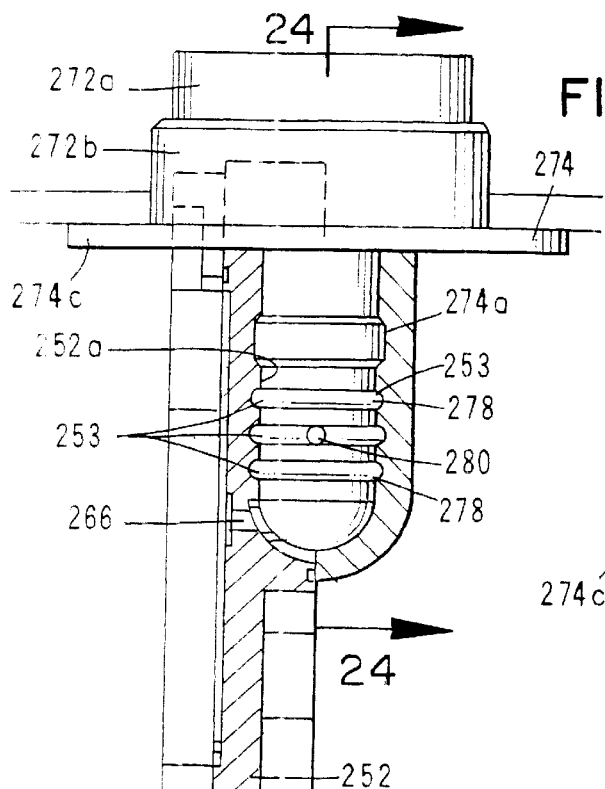
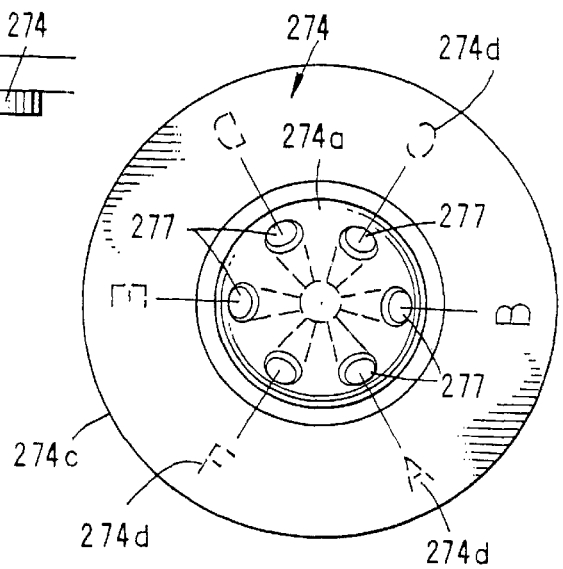
FIG. 23
FIG. 25
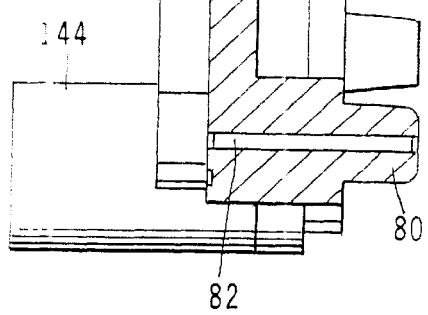
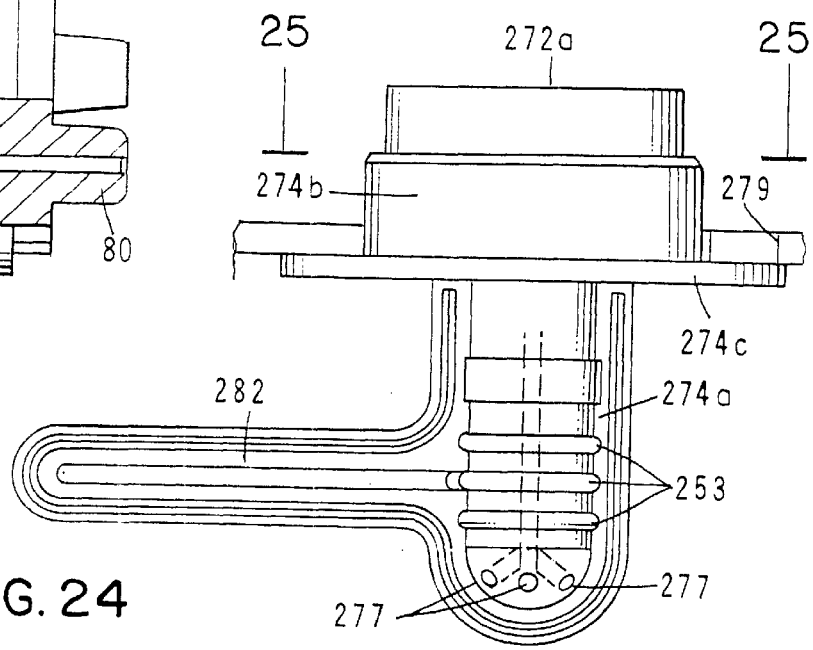
FIG. 24

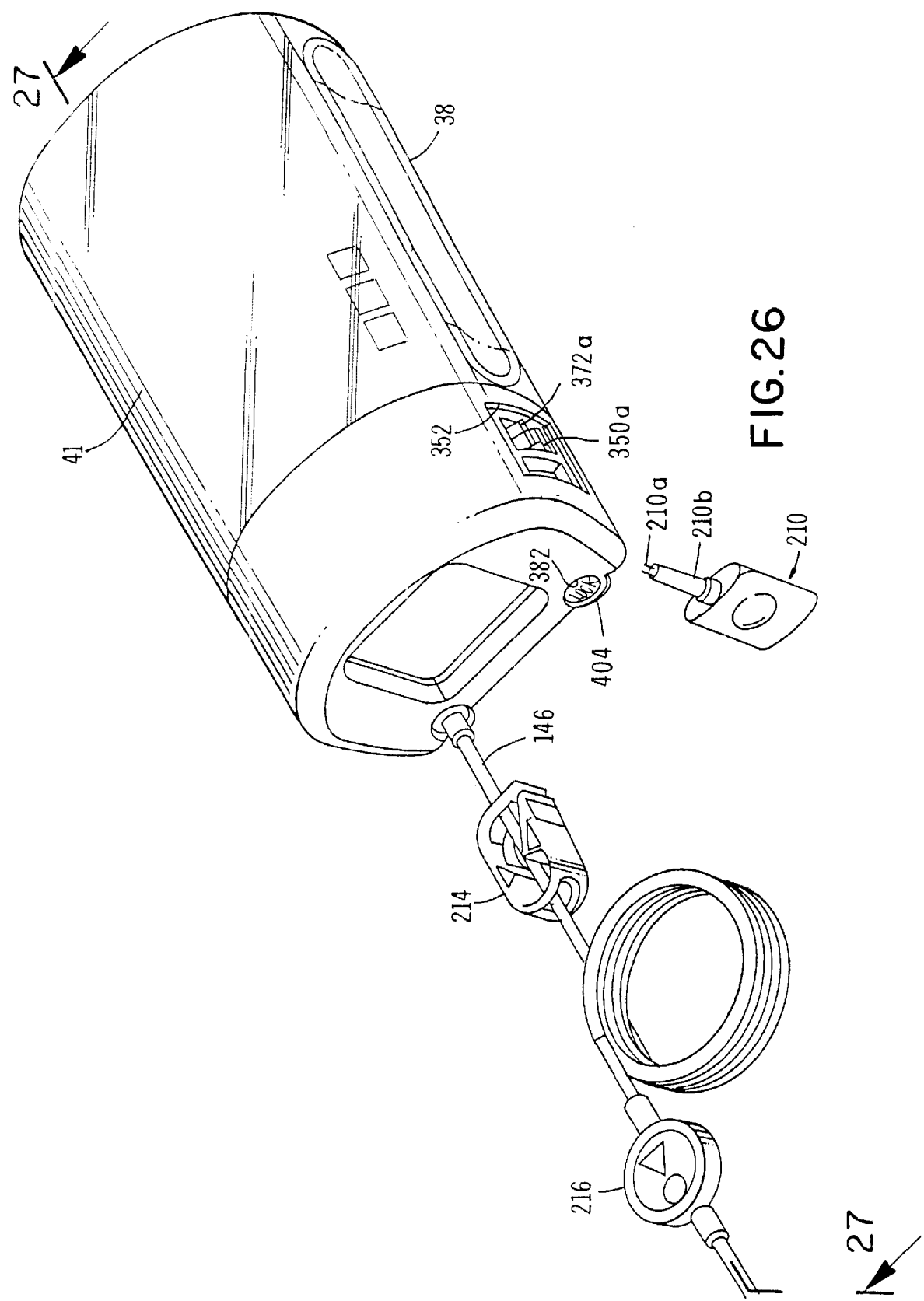

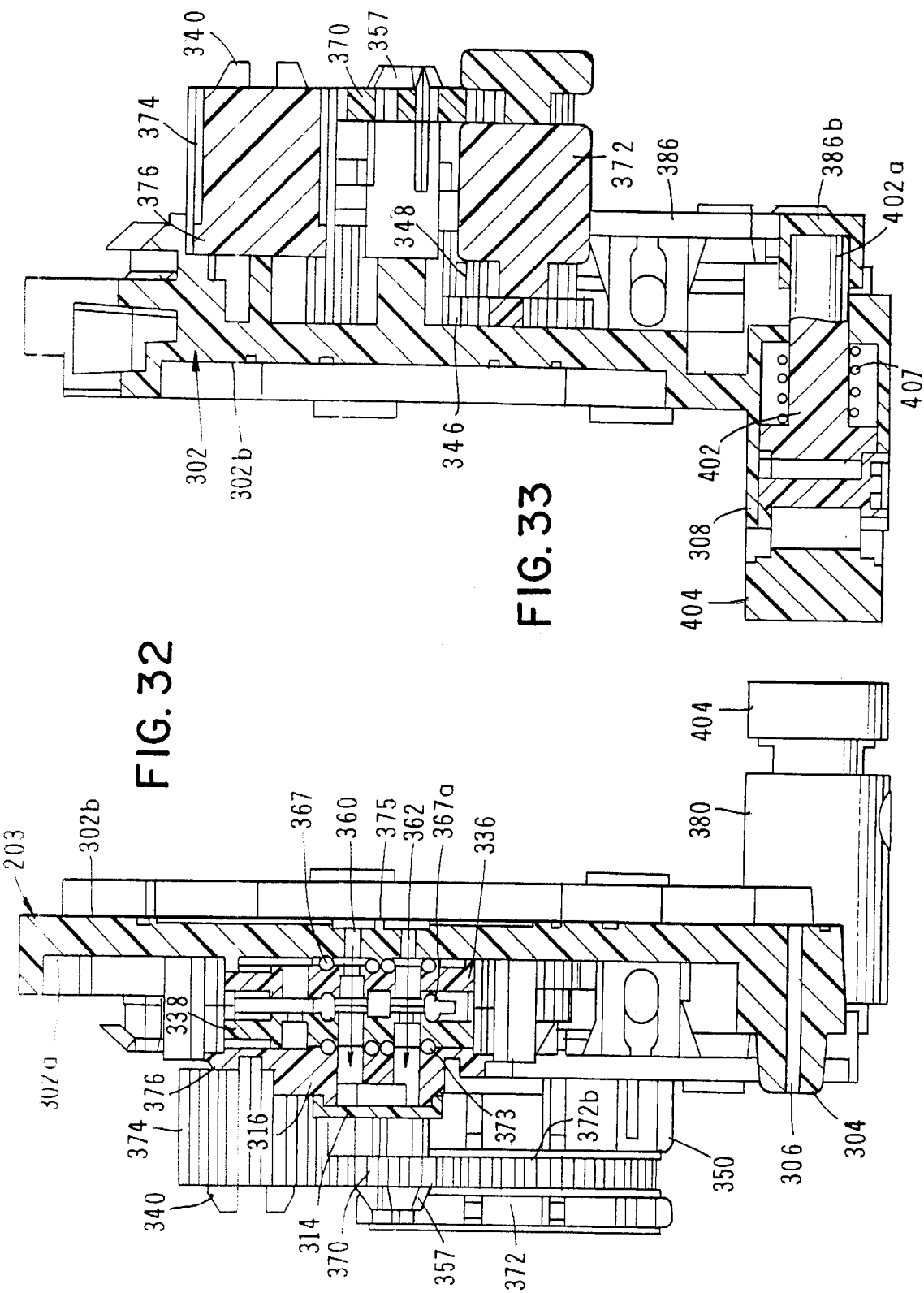

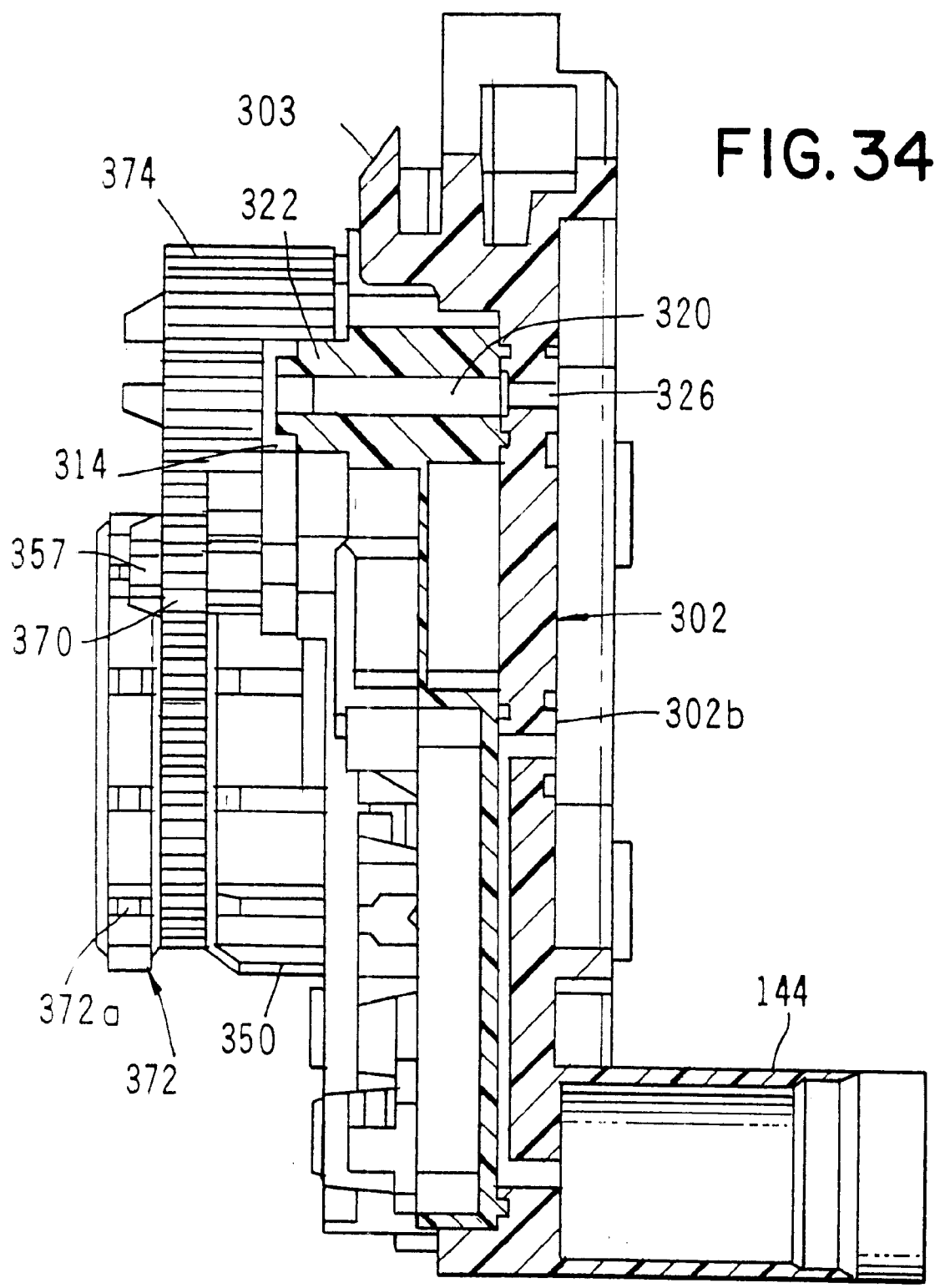

$R_1$ = PRIMARY RATE CONTROL, COARSE ADJUSTMENT (B-D)
$R_2$ = PRIMARY RATE CONTROL, FINE ADJUSTMENT (A-C)

FLUID DELIVERY APPARATUS WITH FLOW INDICATOR AND VIAL FILL

This is a Continuation of U.S. application Ser. No. 09/165,706 filed Oct. 2, 1998 U.S. Pat. No. 6,176,845 which is a Continuation-In-Part of U.S. application Ser. No. 08/768,663 filed Dec. 18, 1996, now U.S. Pat. No. 5,840,071.

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time, which apparatus includes fluid flow indicator means and a novel adjustable flow rate control means for precisely adjustably controlling the rate of fluid flow from the reservoir of the device.

2. Discussion of the Prior Art

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus. Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder. The prior art bladder type infusion devices are not without drawbacks. Generally, because of the very nature of the bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films and similar materials, which, in cooperation with a base define a fluid chamber that contains the fluid which is to be dispensed. The elastomeric film membrane controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to the present inventor. Therefore, U.S. Pat. No. 5,205,820 is hereby incorporated by reference in its entirety as though fully set forth herein. Co-pending U.S. Ser. No. 08/768,663 filed by the present inventors on Dec. 18, 1996 also describes various alternate constructions and modified physical embodiments of the invention. Because the present application discloses improvements to the apparatus described in U.S. Ser. No. 08/768,663, this co-pending application is also hereby incorporated by reference in its entirety as though fully set forth herein. U.S. Pat. No. 5,721,382 issued to the present inventor on Feb. 24, 1998 discloses an apparatus for indicating fluid pressure within a conduit. The present invention comprises an improvement to the devices disclosed in this latter patent and, therefore, U.S. Pat. No. 5,721,382 is also incorporated by reference as though fully set forth herein.

The apparatus of the present invention can be used with minimal professional assistance in an alternate health care environment, such as the home. By way of example, devices of the invention can be comfortably and conveniently removably affixed to the patient's body and can be used for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

The embodiments of the invention described in U.S. Ser. No. 08/768,663, which application is incorporated herein by reference, comprises a fluid delivery apparatus having a fluid reservoir and an indicator assembly for indicating fluid flow through the apparatus. However, the apparatus of the present invention, also includes a unique, adjustable fluid flow rate mechanism which enables the fluid contained within the reservoir of the device to be precisely dispensed at various selected rates. As will be better understood from the description which follows, the novel adjustable fluid flow rate control mechanism of the present invention includes locking means which is operable only by a physician or health care worker who is in possession of a physician operating key. Accordingly, once a particular flow rate is selected, the patient cannot unilaterally change the flow rate.

SUMMARY OF THE INVENTION

It is an object of the present invention to provide an apparatus for expelling fluids at a precisely controlled rate which is of a compact, low profile, laminate construction. More particularly, it is an object of the invention to provide such an apparatus which can be used for the precise infusion of pharmaceutical fluids to an ambulatory patient at controlled rates over extended periods of time.

It is another object of the invention to provide an apparatus of the aforementioned character which is highly reliable and easy-to-use by lay persons in a non-hospital environment.

Another object of the invention is to provide an apparatus which can be factory prefilled with a wide variety of medicinal fluids or one which can readily be filled in the field shortly prior to use.

A further object of the invention is to provide a low profile, fluid delivery device of laminate construction which can be manufactured inexpensively in large volume by automated machinery.

Another object of the invention is to provide a device of the aforementioned character which includes novel adjustable flow rate control means disposed intermediate the fluid reservoir outlet and the outlet port of the device for precisely controlling the rate of fluid flow from the outlet port toward the patient.

Another object of the invention is to provide a device of the character described which embodies a highly novel fluid flow indicator that provides a readily discernible visual indication of fluid flow status through the device.

Another object of the invention is to provide an apparatus of the aforementioned character in which the stored energy source is of a novel laminate construction which can be precisely tailored to deliver fluid from the device at precise rates.

Another object of the invention is to provide unique fill means for use in controllably filling the fluid reservoir of the apparatus.

Another object of the present invention is to provide an apparatus of the aforementioned character in which the flow rate control means comprises a rotatable flow restrictor support disk that can be rotated by the treating physician to selectively position the flow restrictor between the fluid reservoir and the device outlet port.

Another object of the present invention is to provide a flow rate control means of the type described in the preceding paragraph in which the flow restrictors comprise porous frits of varying porosity.

Another object of the present invention is to provide a flow rate control means in which the flow restrictors comprise wafers which have been laser drilled to provide a plurality of micro bores of various sizes.

Another object of the invention is to provide an apparatus as described in the preceding paragraphs which includes locking means for locking the variable flow rate control disk in a preset position so that the rate control can be set only by the treating physician or an authorized health care worker having an operating key.

Another object of the invention is to provide a novel fill assembly for use in filling the fluid reservoir of the apparatus of the invention.

By way of summary, the improved fluid delivery apparatus of the present form of the invention comprises three major cooperating subassemblies, namely a reservoir subassembly, a highly novel adjustable, key-operated fluid flow rate control subassembly and a flow indicator subassembly for visually indicating fluid flow through the device. The reservoir subassembly, which readily lends itself to automated manufacture, is generally similar to that described in copending U.S. Ser. No. 08/768,663 and includes a base and a stored energy means comprising at least one distendable elastomeric membrane which cooperates with the base to form a fluid reservoir. The fluid flow indicator subassembly is also somewhat similar to that described in U.S. Ser. No. 08/768,663 and comprises a mechanical fluid flow indicator that provides a clear visual indication of normal fluid flow and absence of fluid flow either because the reservoir is empty or because the flow lines are occluded. Additionally, the apparatus of the invention includes fill means for use in filling the reservoir of the reservoir subassembly this fill means here comprises a fill assembly which can be mated with the base of the reservoir subassembly for use in controllably filling the reservoir thereof.

BRIEF DESCRIPTION OF THE DRAWINGS

FIG. 5 is a bottom plan view of the housing portion of the apparatus of the invention shown in FIG. 1.

FIG. 5A is an enlarged, fragmentary bottom view of one form of the physician locking means of the invention in a first configuration.

FIG. 5B is a fragmentary bottom view similar to FIG. 5A, but showing the locking means in a second unlocked configuration.

FIG. 11 is a cross-sectional view taken along lines 11—11 of FIG. 10.

FIG. 11 A is a generally perspective, fragmentary view of a portion of the adjustable flow rate control mechanism and a portion of the locking mechanism.

FIG. 12 is a cross-sectional view taken along lines 12—12 of FIG. 10.

FIG. 12A is a cross-sectional view of the locking mechanism of the invention in an unlocked configuration permitting rotation of the control knob of the device.

FIG. 13 is a cross-sectional view taken along lines 13—13 of FIG. 10 and showing the locking mechanism in a locked position preventing rotation of the control knob.

FIG. 14 is a cross-sectional view taken along lines 14—14 of FIG. 10.

FIGS. 15A and 15B when considered together comprise a greatly enlarged, generally perspective exploded rear view of the support means and the adjustable flow rate control mechanism of the apparatus of the invention showing the construction of the adjustable rate control mechanism and also showing a portion of the lockout means of the apparatus of the invention.

FIGS. 17A and 17B, when considered together, comprise a generally perspective, exploded bottom view of a portion of the reservoir assembly of the apparatus, a portion of the support means, a portion of the adjustable flow rate control mechanism and a portion of the flow indicator means with directional arrows illustrating the fluid flow path through the apparatus.

FIG. 20 is a generally perspective top view of the cover and the forward portion of the housing of an alternate form of the apparatus of the invention in which the adjustable flow rate control mechanism is mounted proximate the top of the housing rather than in the base portion thereof.

FIGS. 22A and 22B, when considered together, comprise a generally perspective, exploded view of the support means and of the manifold plate of the alternate form of the apparatus of the invention and depicted by use of directional arrows the fluid flow path there through the forward portion of the alternate embodiment of the invention.

FIG. 23 is a greatly enlarged, side-elevational, cross-sectional view of a portion of the support means and a portion of the adjustable flow rate control means of this latest form of the invention.

FIG. 24 is a cross-sectional view taken along lines 24—24 of FIG. 23.

FIG. 25 is a cross-sectional view taken along lines 25—25 of FIG. 24.

FIG. 26 is a generally perspective view of an alternate form of the apparatus of the present invention.

FIG. 32 is a cross-sectional view taken along lines 32—32 of FIG. 27B.

FIG. 33 is a cross-sectional view taken along lines 33—33 of FIG. 27B.

FIG. 34 is an enlarged, cross-sectional view taken along lines 34—34 of FIG. 27B.

FIG. 35 is a generally illustrative front view of one type of flow rate control members of the invention.

FIG. 36 is an enlarged, cross-sectional view taken along lines 36—36 of FIG. 35.

DISCUSSION OF THE INVENTION

Figure 1:
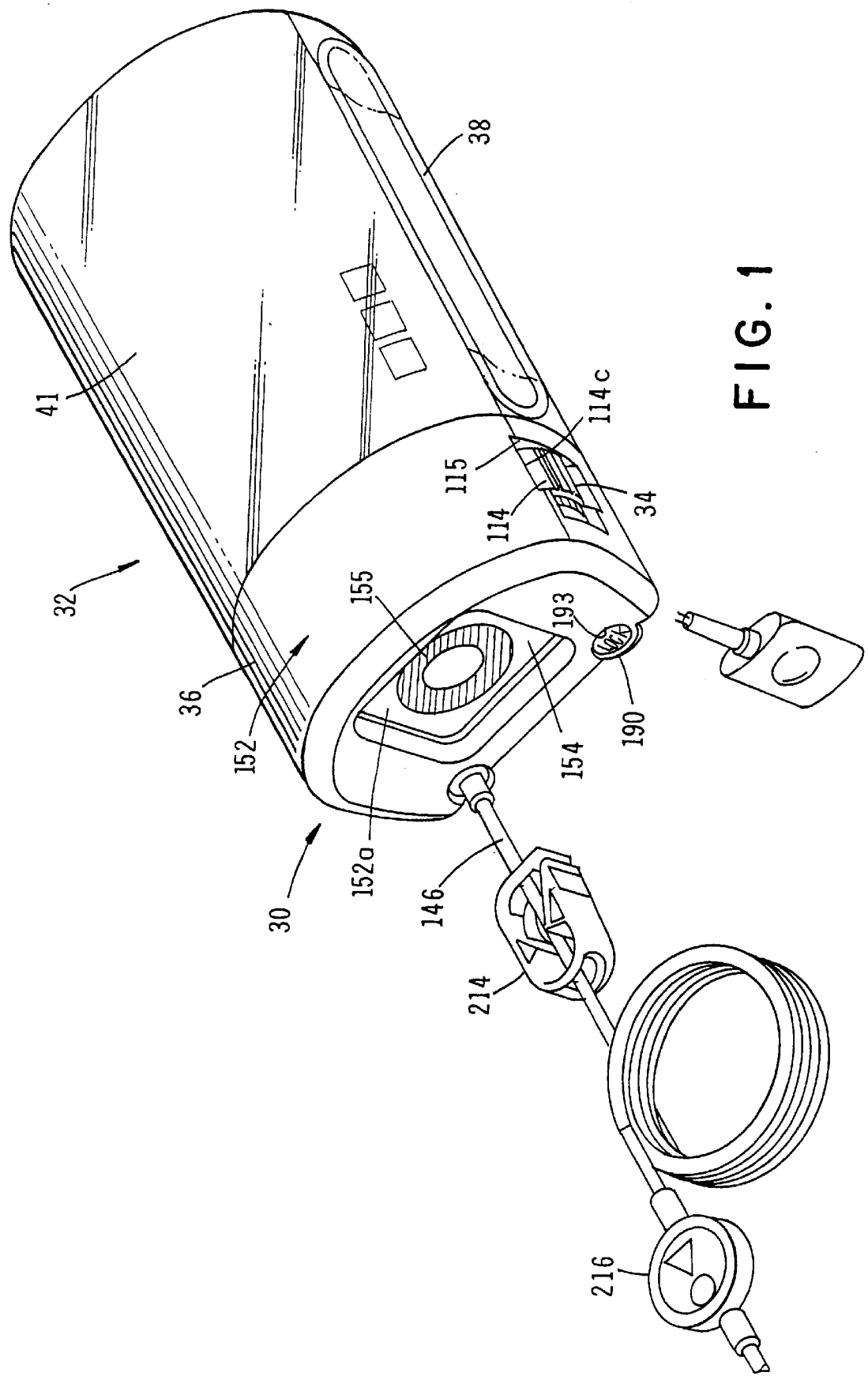
FIG. 1 is a generally perspective view of one form of the apparatus of the present invention which includes a flow indicator means for indicating fluid flow as well as a novel adjustable flow rate control means for precisely controlling the rate of fluid flow from the reservoir of the apparatus
Figure 1A:
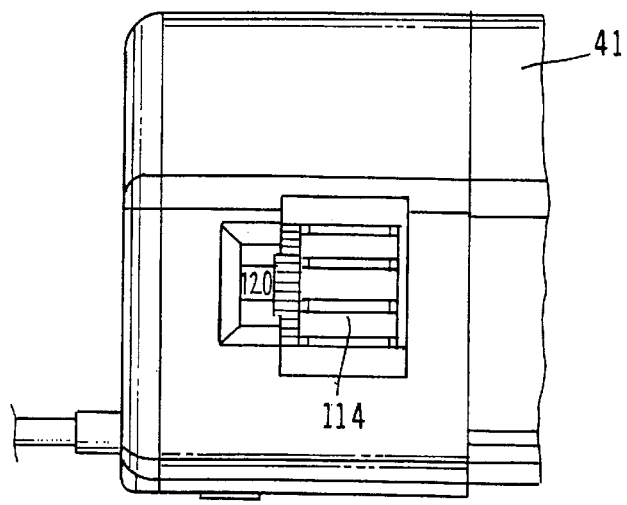
FIG. 1A is an enlarged, fragmentary side-elevational view of the forward portion of the apparatus shown in FIG. 1 showing the adjustable flow rate control means.
Figure 2A:
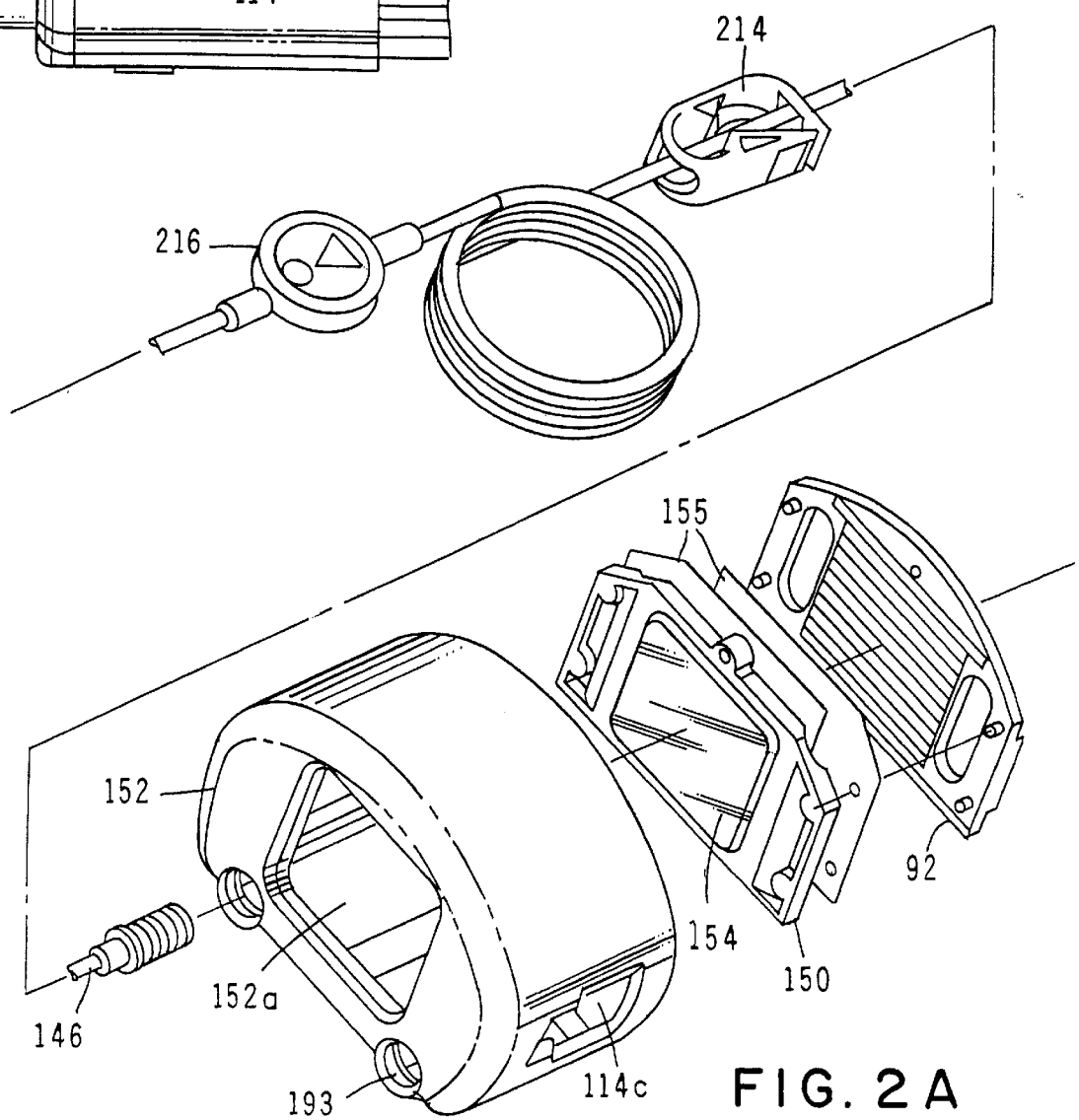
FIGS. 2A and 2B when considered together comprise a generally perspective, exploded view of the apparatus of the invention shown in FIG. 1.
Figure 2B:
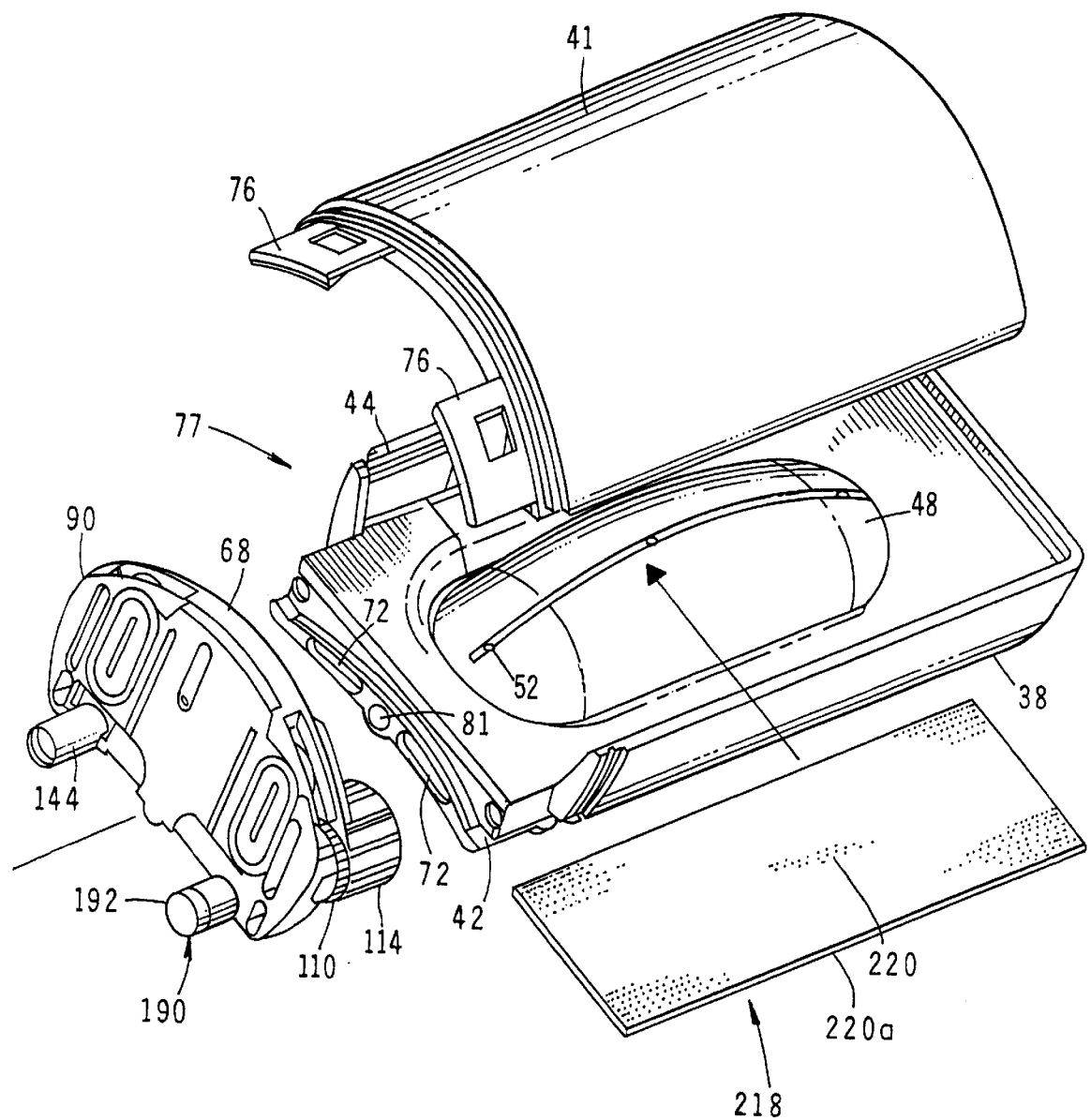
Figure 3:
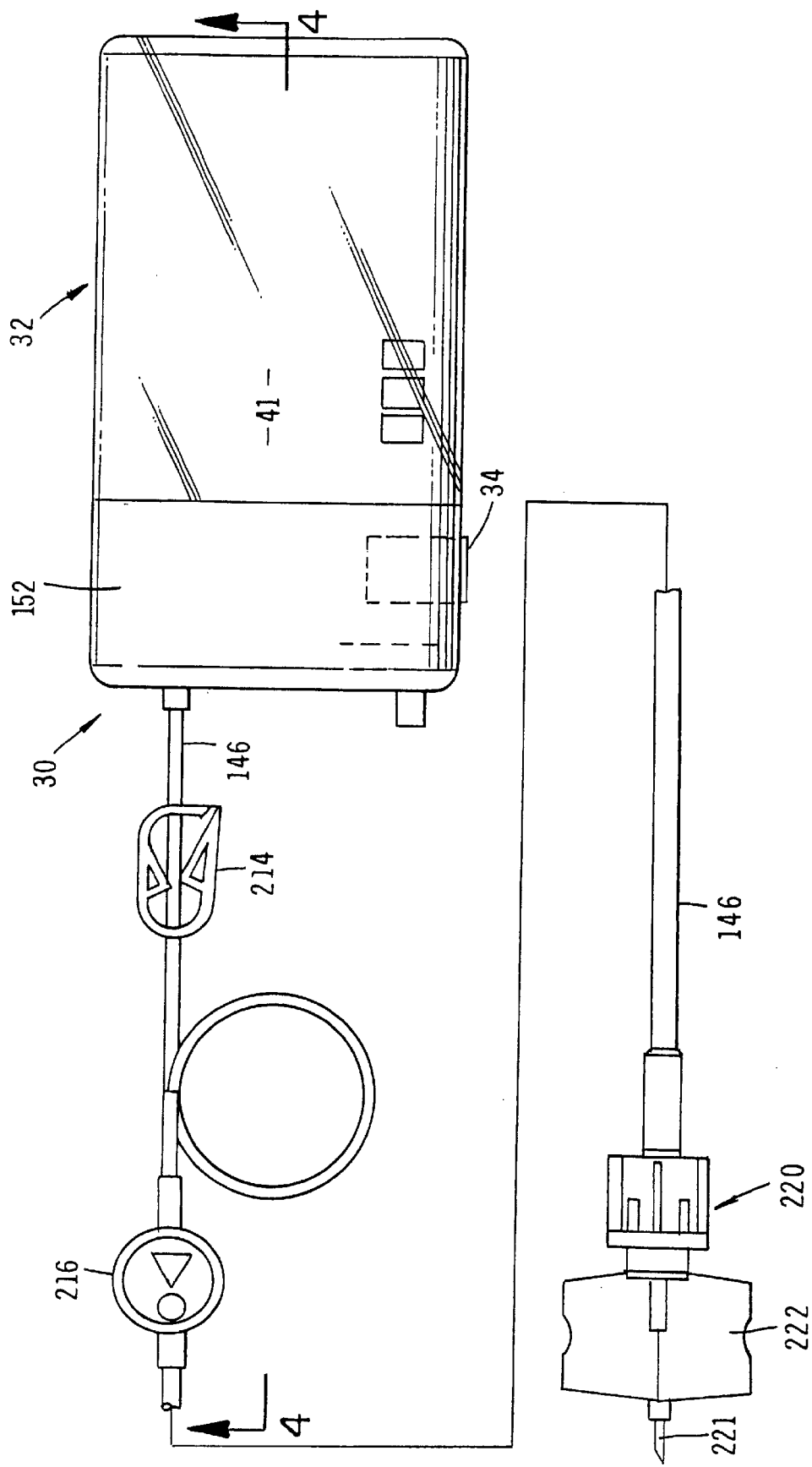
FIG. 3 is a top plan the view of the apparatus shown in FIG. 1.
Figure 4:
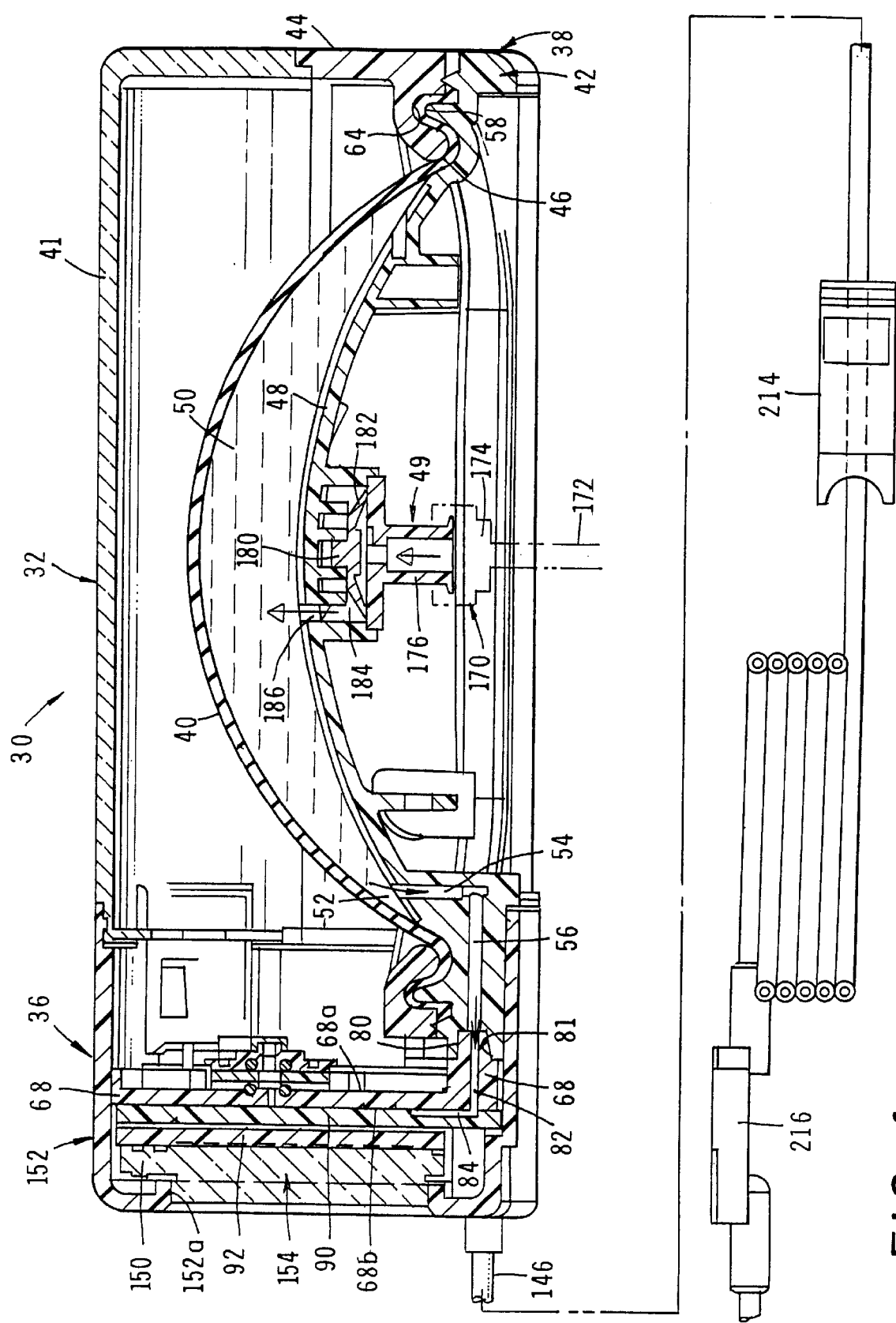
FIG. 4 is an enlarged, side-elevational, cross-sectional view taken along lines 4—4 of FIG. 3.
Figure 4A:
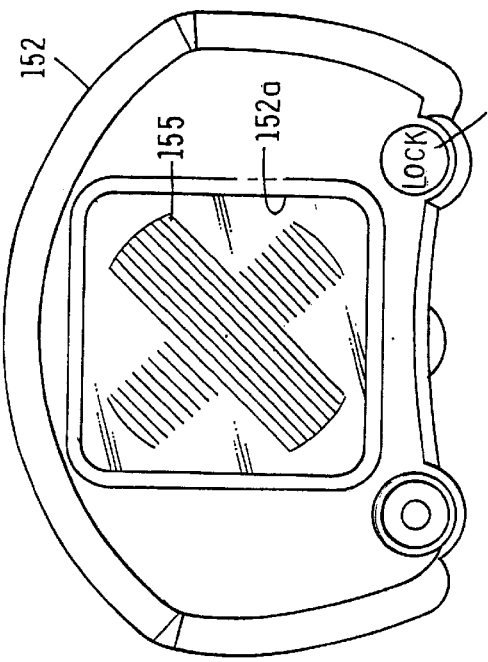
FIG. 4A is a greatly enlarged, fragmentary, cross-sectional view of the forward portion of the housing of the apparatus shown in FIG. 4.

Referring to the drawings and particularly to FIGS. 1 through 5, one form of the apparatus of the present form of the invention is there illustrated and generally designated by the numeral 30. As best seen in FIGS. 1 and 4, the apparatus here comprises four major cooperating subassemblies namely, a reservoir subassembly 32, an adjustable flow rate control subassembly 34, a flow indicator subassembly 36 and fill means for filling the fluid reservoir of the reservoir subassembly. The construction and operation of each of these cooperating subassemblies will be discussed in greater detail in the paragraphs which follow.

Considering first the reservoir subassembly shown in FIG. 4, this subassembly includes a base assembly 38, a stored energy source, shown here as a distendable membrane 40, and a cover 41 for enclosing the stored energy source. The base assembly includes an ullage substrate 42 and a membrane capture housing 44 having a bottom opening 46 which receives the distendable membrane engaging element or protuberance 48 of ullage substrate 42. Referring particularly to FIGS. 4 and 5, the ullage substrate, or base, 42 also includes a fill assembly 49, which forms a part of the fill means of the invention.

The stored energy means can be in the form of a single prestressed or unstressed isotropic, elastomeric, distendable membrane, or it can comprise a laminate assemblage made up of a plurality of initially generally planar distendable elements or films. The distendable membrane 40 is distended by fluid pressure exerted on the membrane by fluid flowing into the reservoir 50 under pressure. As membrane 40 is distended, additional internal stresses are formed therein which continuously urge the membrane in a direction toward engagement with protuberance 48. During the delivery operation, as the membrane moves toward protuberance 48, fluid within reservoir 50 will be uniformly and controllably forced outwardly through reservoir outlet 52, through passageway 54 and finally through longitudinally extending passageway 56 which is formed in ullage substrate 42.

An upstanding tongue 58 formed on ullage substrate 42 extends completely about the perimeter of member 42 and is closely receivable within a groove 64 formed in capture housing 44. When the ullage substrate and the membrane capture housing are assembled in the manner shown in FIG. 4, the periphery of distendable membrane 40 will be securely clamped within groove 64 by tongue 58. After the parts are thus assembled, capture housing 44 is bonded to member 42 by any suitable means such as adhesive or sonic bonding. This done, cover 41 is mated with capture housing 44 and bonded in place. This assembly and bonding step is discussed more fully in incorporated by reference U.S. application Ser. No. 08/768,663.

Reference should be made to U.S. Pat. No. 5,205,820 for the various materials that can be used to construct base assembly 38, membrane 40, cover 41, and the membrane capture housing 44 as identified in the preceding paragraph.

Turning now to a consideration of the important flow rate control means of the invention, for controlling the rate of fluid flow of fluid from the device, this means here comprises an adjustable rate control mechanism which is carried by a support means shown here as comprising a deck-like support 68 which includes first and second faces 68a and 68b. Support 68 is connected to base assembly 38 and cover 41 in the manner best seen in FIGS. 2B and 4. For this purpose wing-like protuberances 70 (FIG. 6) are formed on support 68, which protuberances are received within spaced-apart, arcuate-shaped cavities 72 formed in base assembly 38 (FIG. 2B). Located proximate the upper edge of support 68 are arcuately, spaced connector members 74 (FIG. 6) which mate with arcuately spaced connectors 76 provided on cover 41 (FIG. 2B) to enable secure interconnection of support 68 with the base assembly to form the hollow housing of the device generally designated by the numeral 77 (FIG. 2B).

Figure 16A:
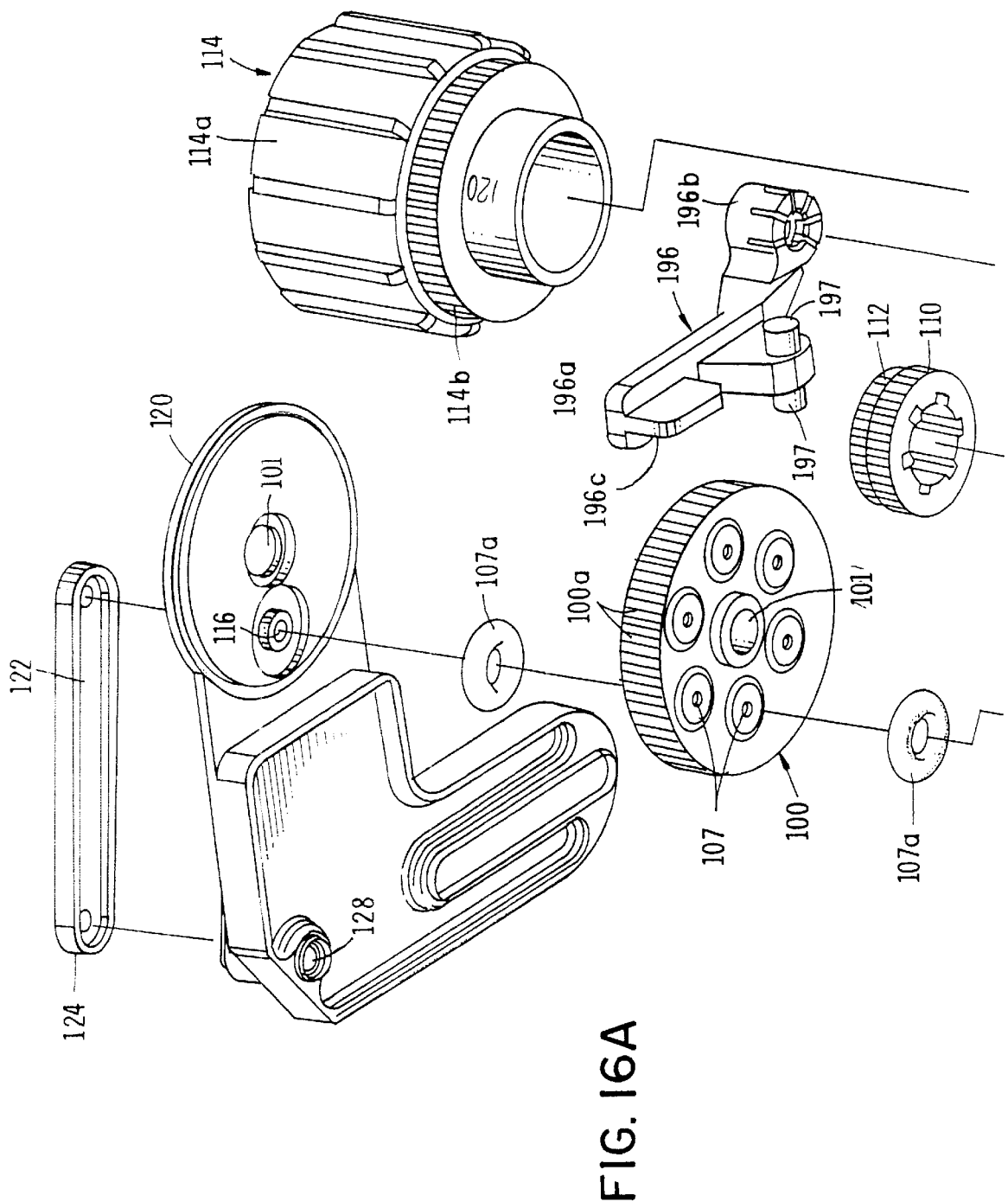
FIGS. 16A and 16B when considered together comprise a greatly enlarged generally perspective exploded front view of the support means, a portion of the adjustable flow rate control mechanism and another portion of the locking means of the invention as shown in FIGS. 15A and 15B.
Figure 16B:
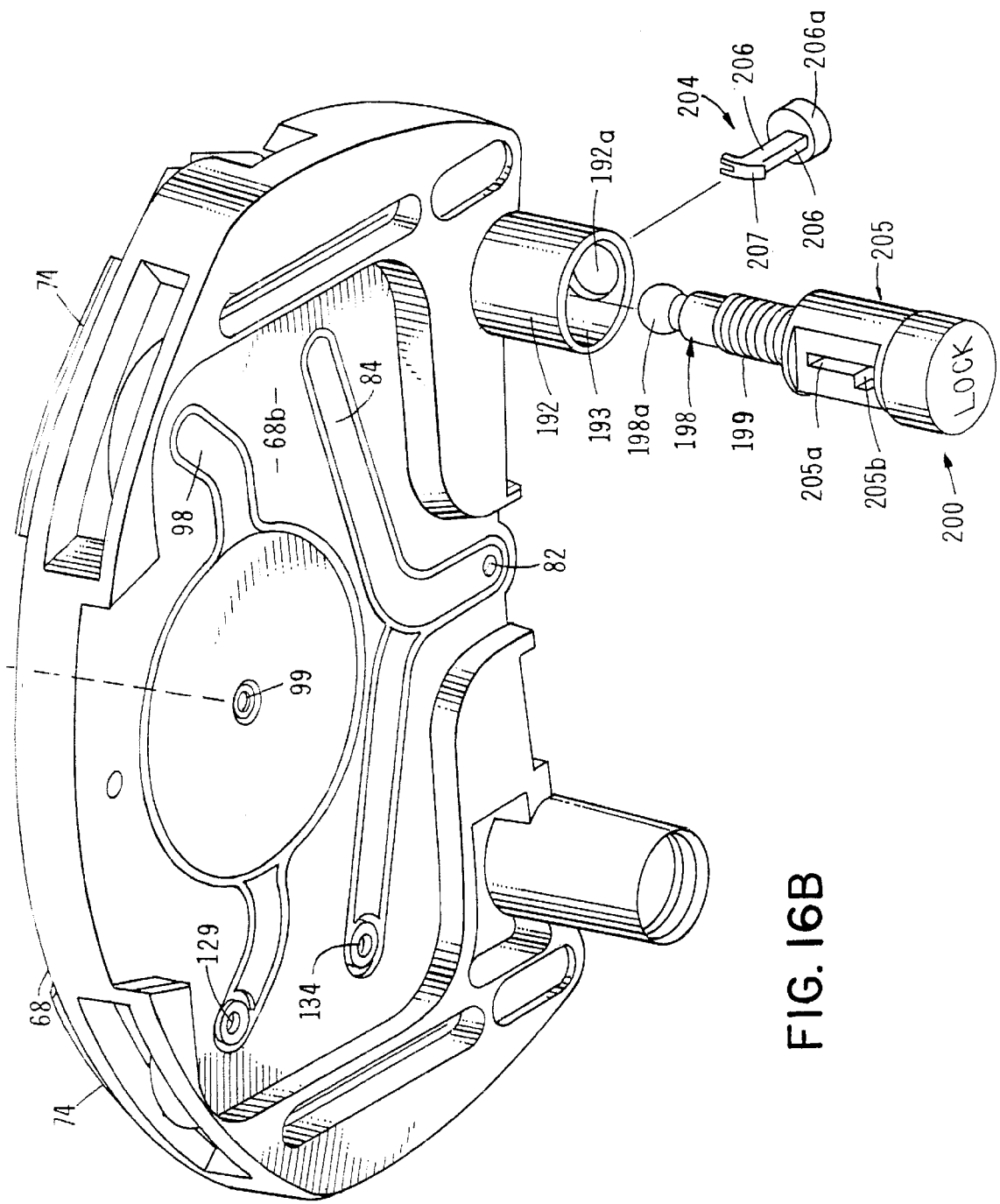
Figure 17C:
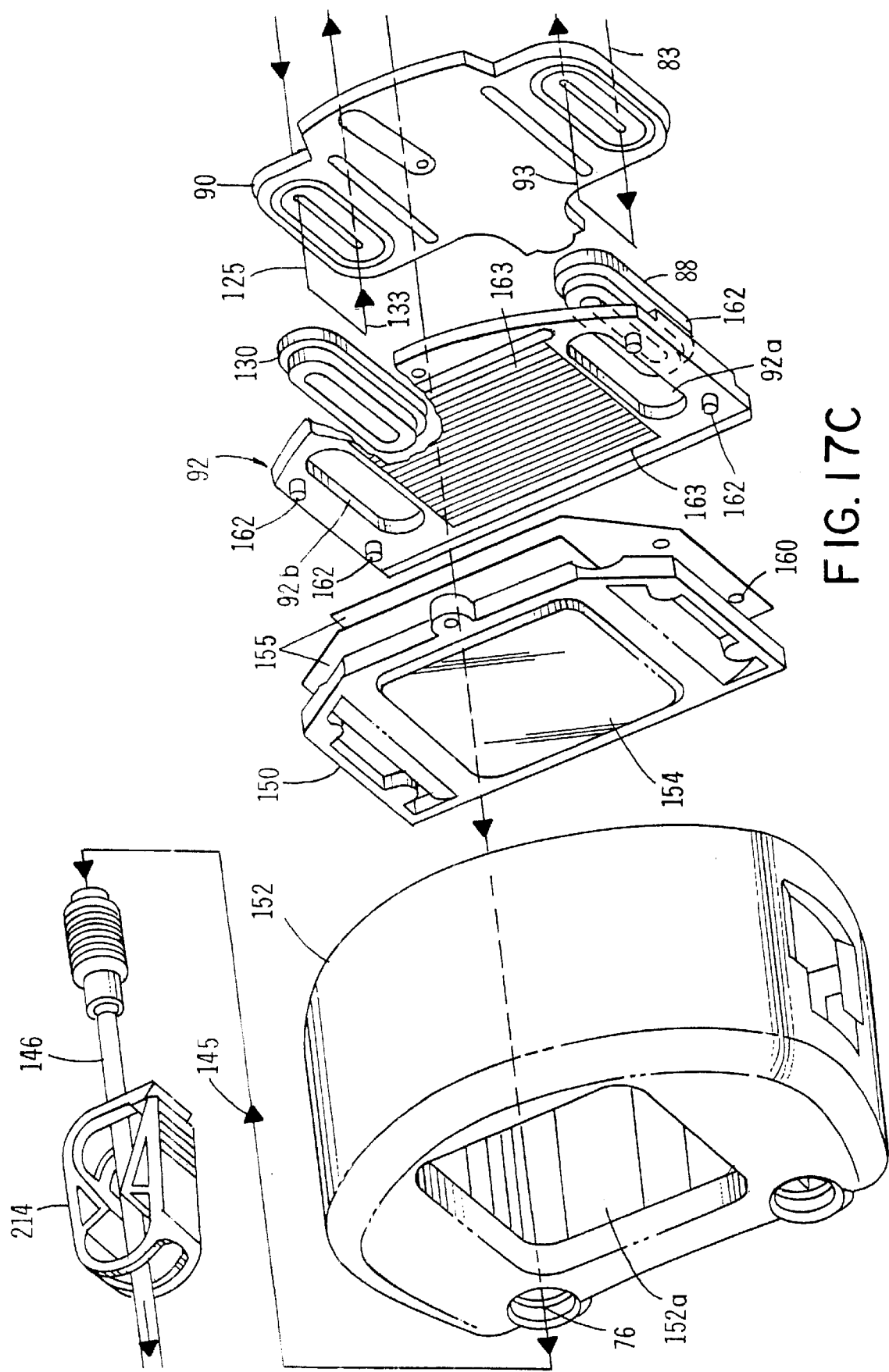
FIGS. 17C and 17D, when considered together, comprise a generally perspective exploded top view similar to FIGS. 17A and 17B further illustrating the operating system and indicating with directional arrows the fluid flow path through the apparatus.

As shown in FIG. 4, support 68 of the support means includes an outwardly extending, generally frustoconically shaped fluid inlet protuberance 80 which is closely receivable within a socket like cavity 81 formed in base member 42. When support 68 is mated with base assembly 38, a fluid inlet passageway 82 formed in protuberance 80 and is placed in fluid communication with reservoir 50 via passageways 54 and 56. With this construction, when fluid is forced through reservoir outlet 52 by the stored energy means, the fluid will flow into passageway 54, into passageway 56 and then into passageway 82 formed in protuberance 80. Next, the fluid will flow in the direction of arrow 83 (FIG. 17B) into a passageway 84 formed in face 68b of support 68 (FIGS. 16B and 17D) and finally into a chamber 86 formed in a distendable, elastomeric first boot 88 of the flow indicator means of the invention (FIG. 17A). Boot 88 is of similar construction to boot 266 shown in FIG. 13A of incorporated by reference U.S. Ser. No. 08/768,663 and reference should be made to this application for a more complete discussion of the construction and operation of the flow indicator boots. As best seen in FIGS. 17A and 17B, boot 88 includes a yieldably distendable fluid flow blocking body portion 88a which is circumscribed by a marginal portion 88b. Marginal portion 88b is clamped between a manifold plate 90 and a uniquely configured boot-supporting indicator base 92 so that the boot extends through an opening 92a formed in the indicator base 92. It is to be understood that, when the fluid flowing from reservoir 50 in the direction of arrow 83 fills passageways 56 and 82 and impinges upon boot 88, flow will be diverted in the direction of arrows 93 of FIGS. 17C and 17A rearwardly toward plate 90 and into a passageway 96 which is formed in plate 90. When plate 90 is abutted against support 68, passageway 96 will cooperate with a passageway 97 formed in support 68 (FIG. 17D) to form a closed fluid flow chamber like passageway 98 which is in communication with a control passageway 99 which extends through support 68 (FIGS. 16B and 17B) so that fluid will flow from chamber 98 toward a novel rate control flow passageway formed in a control member 100. Control member 100 and the flow restrictors carried thereby form an important aspect of the previously mentioned fluid rate control means of the invention for controlling the rate of fluid outwardly from the device.

Figure 6:
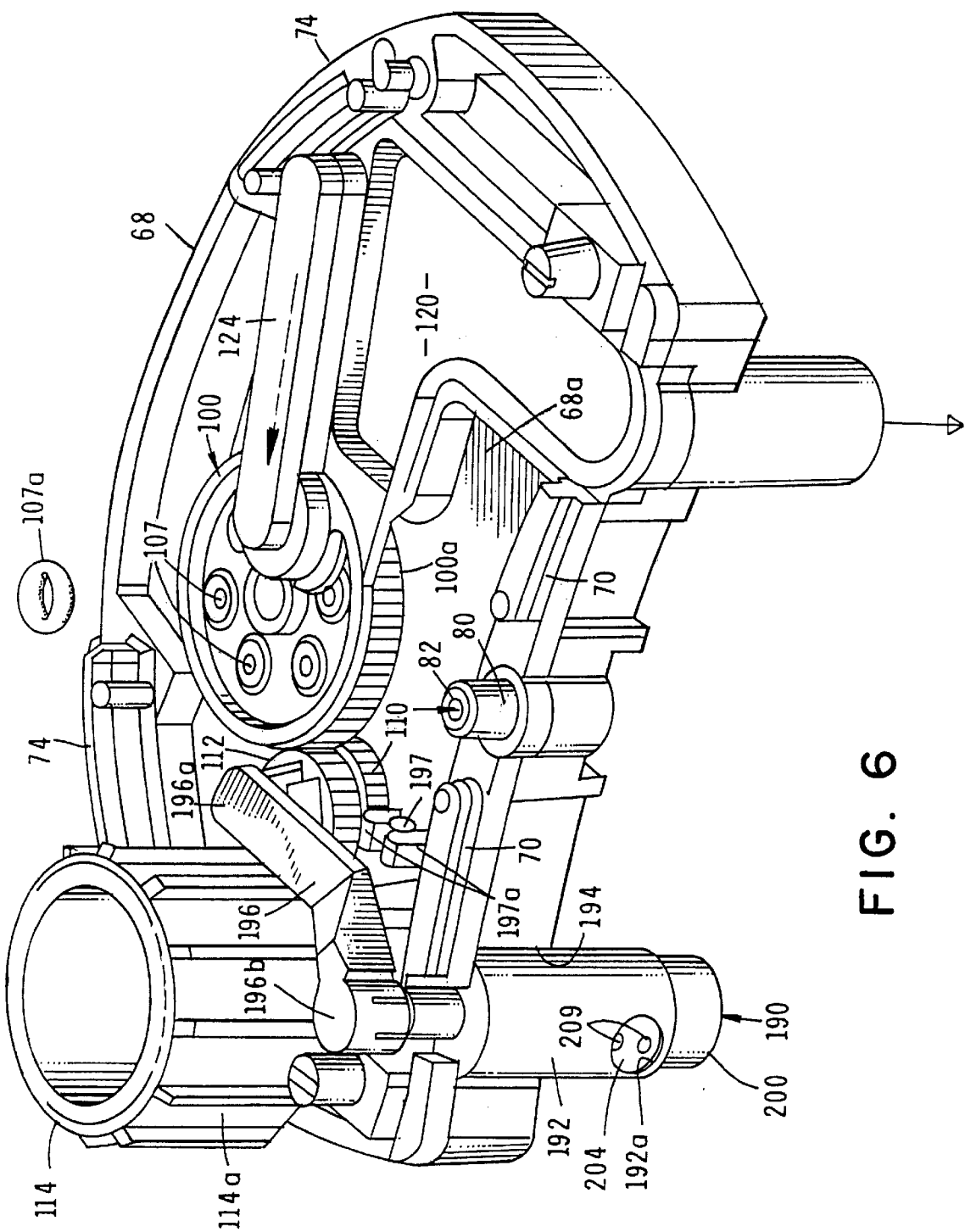
FIG. 6 is a greatly enlarged generally perspective rear view of the support means of the apparatus of the invention illustrating the construction of the adjustable flow rate control mechanism of the device and also showing the face of the locking mechanism of the apparatus for locking out the flow rate control means against adjustment.
Figure 7:
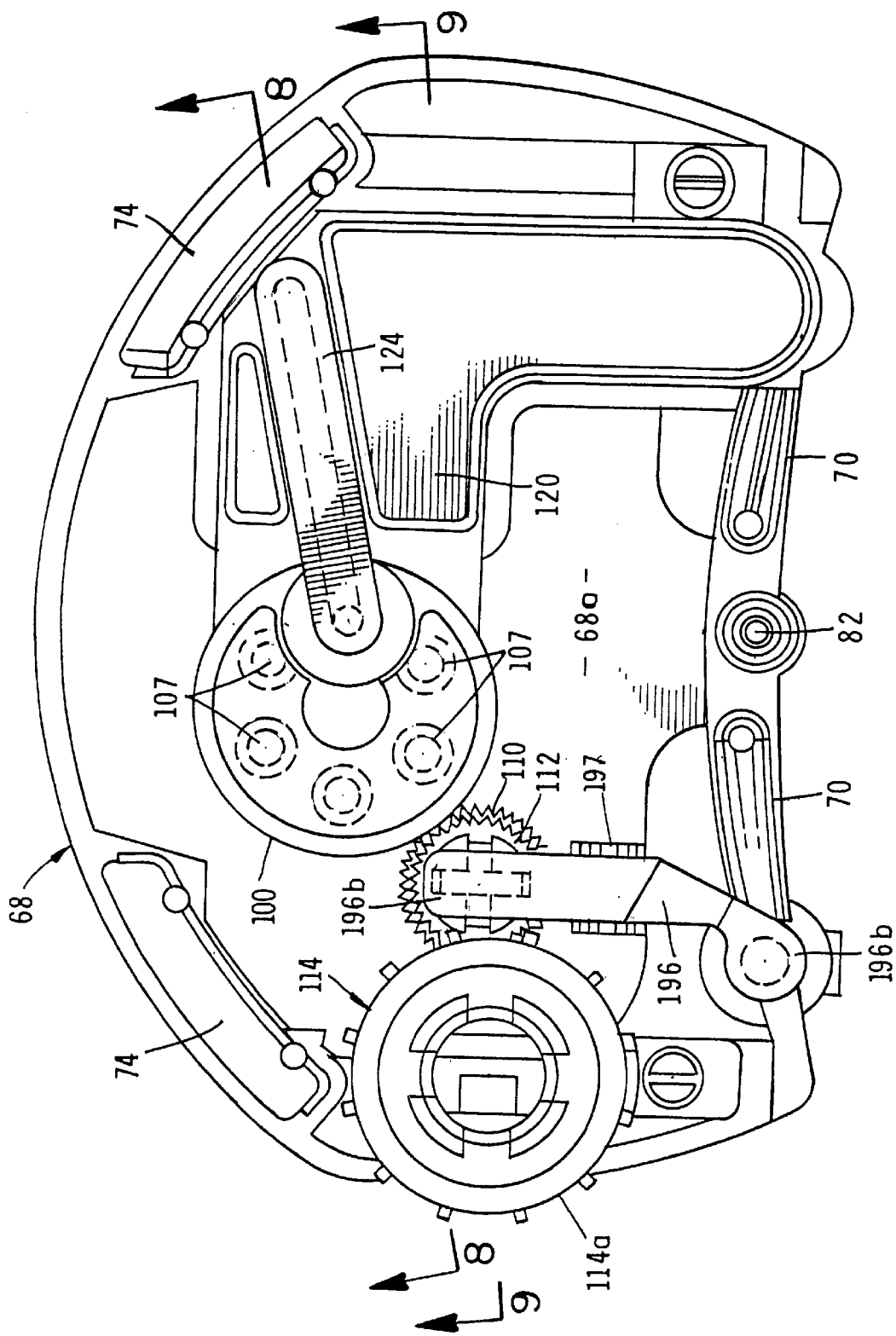
FIG. 7 is an enlarged, rear-elevational view of the support means and adjustable flow rate control mechanism of the apparatus shown in FIG. 6.
Figure 8:
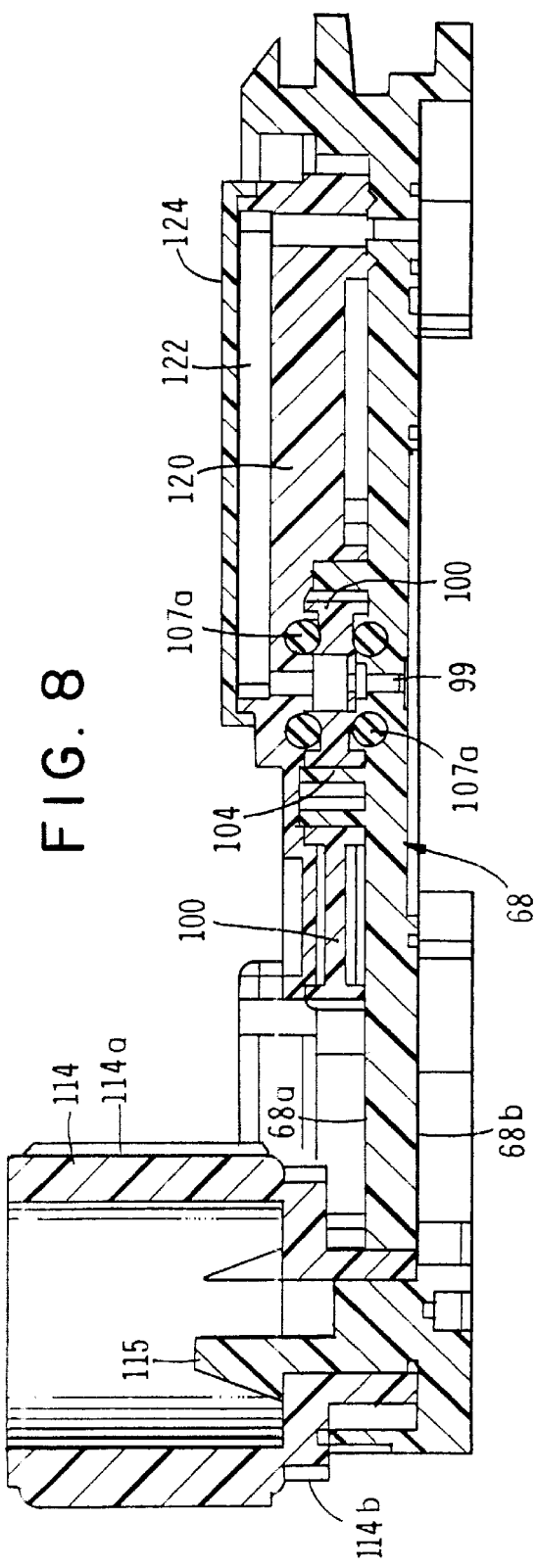
FIG. 8 is a cross-sectional view taken along lines 8—8 of FIG. 7.
Figure 9:
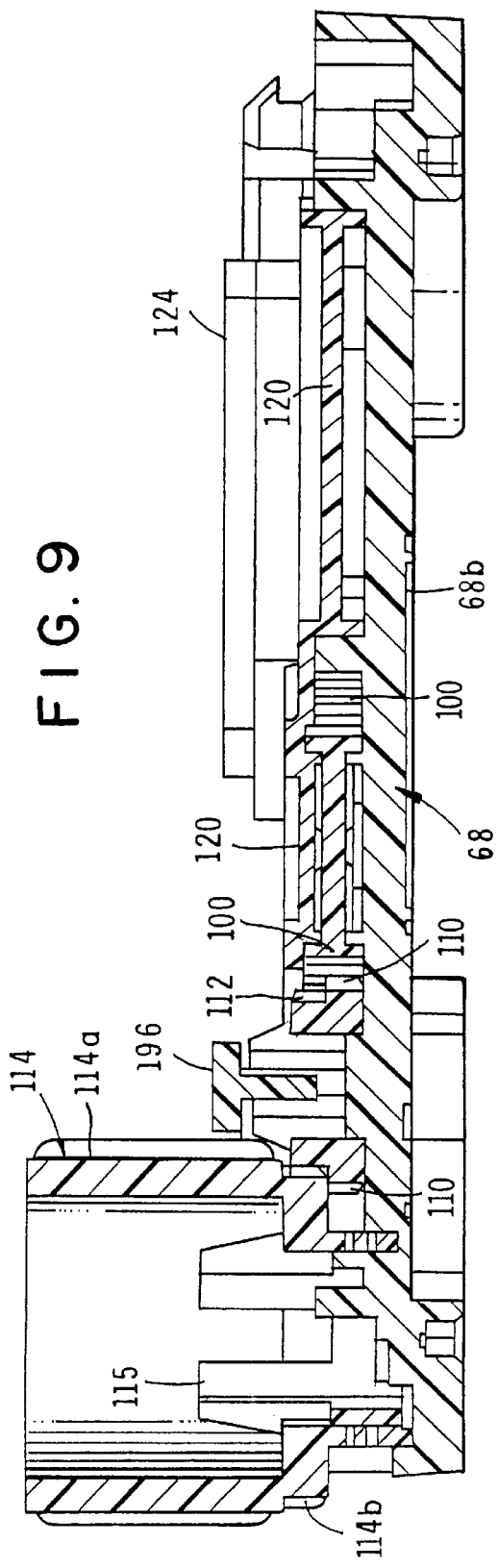
FIG. 9 is cross-sectional view taken along lines 9—9 of FIG. 7
Figure 10:
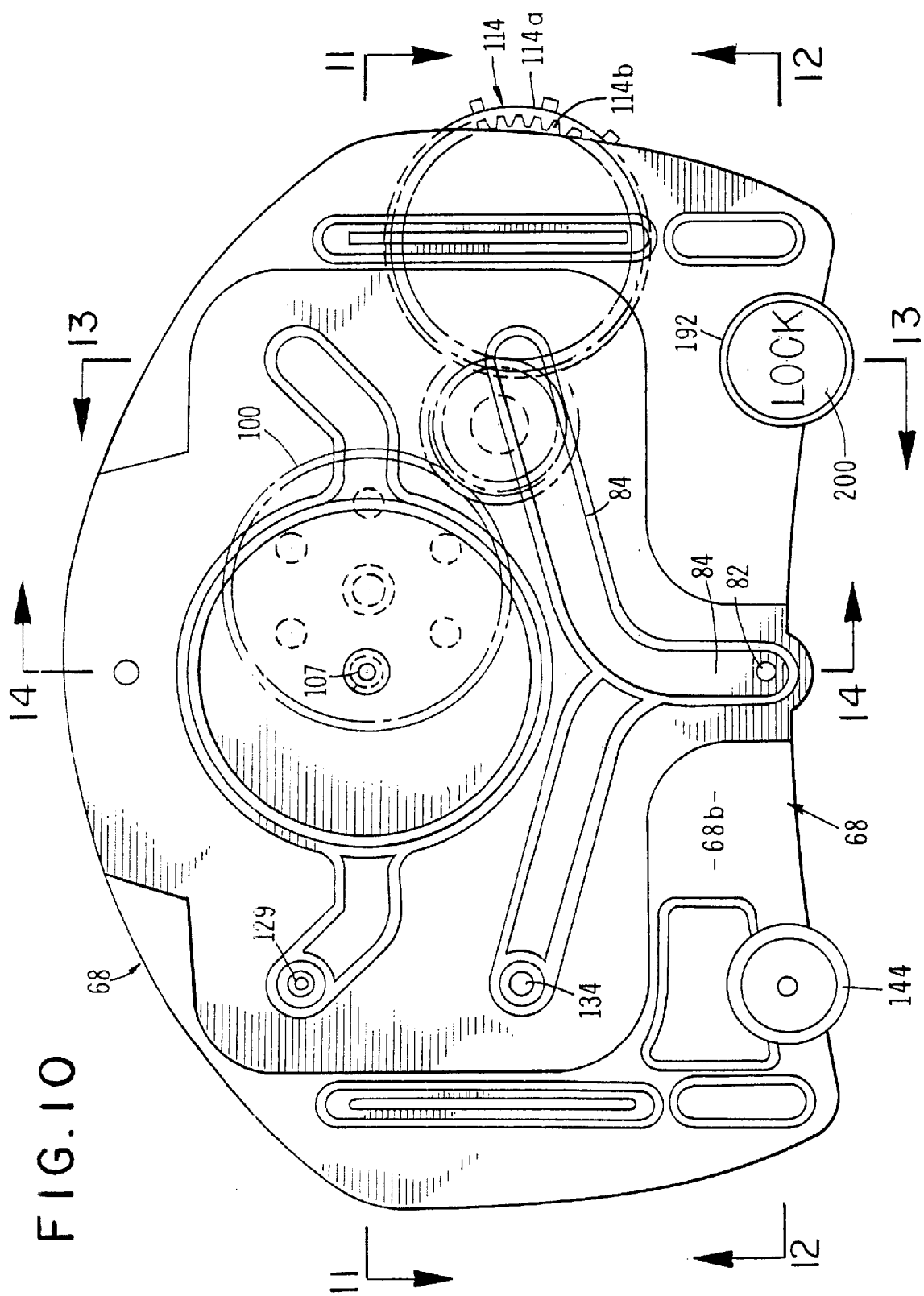
FIG. 10 is an enlarged front elevational view of the support means of the apparatus.
Figure 15B:
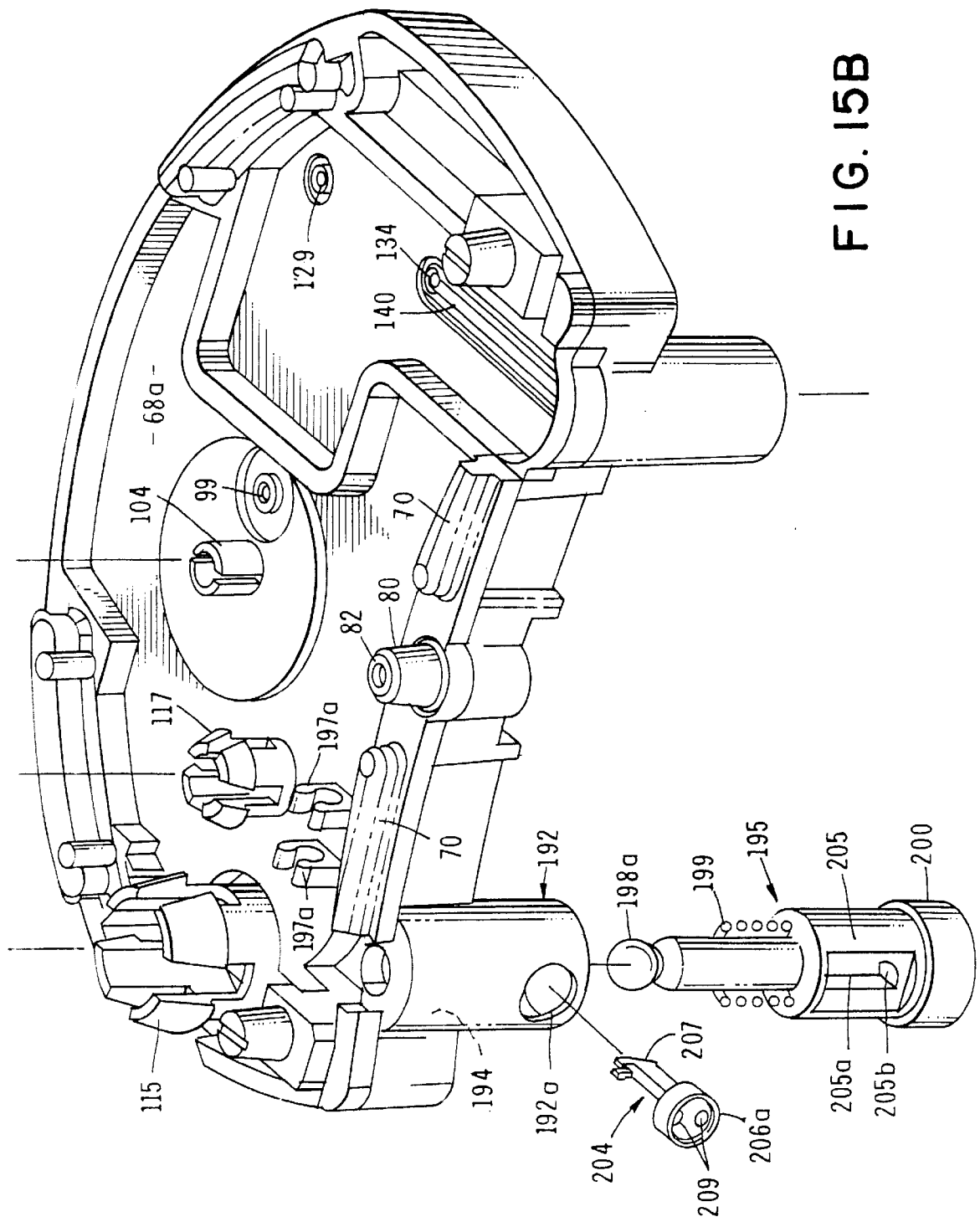

Considering further the novel control member 100, this member is here provided in the form of a generally disk shaped component having teeth 100a formed about its periphery (FIGS. 6 and 15A). As best seen in FIGS. 15A and 15B, control member 100 also has a central bore 101 which receives a spindle 104 so that the member can be controllably rotated relative to face 68a of support 68 (FIG. 6). Circumferentially spaced about central bore 101 is a plurality of apertures 106, each of which is adapted to carry one of the previously mentioned flow restrictors, which here take the form of a porous rate control frit 107 (FIG. 11A). Member 100 is controllably rotated about spindle 104 by a driving member shown here as a toothed wheel 110. Connected to wheel 110 is a coaxially aligned, toothed wheel 112 which is driven by a finger engaging control knob 114 which, as shown in FIGS. 1, 10, and 11 includes a peripheral portion 114a, a portion of which extends through an opening 114c formed in the forward portion of the device (FIG. 2A). Knob 114 includes a lower toothed portion 114b which meshes with toothed wheel 112 so that rotation of knob 114 about spindle 115 (FIG. 15B) will impart rotation to wheels 110 and 112 about a spindle 117 and will also impart rotation to control member 100. With this construction, by rotating knob 114 a selected one of the plurality of rate control frits 107 can be moved into alignment with central passageway 99 of support 68 so that fluid from reservoir 50 will flow therethrough. A pair of elastomeric O-rings 107a sealably engage frits 107 to prevent leakage about the periphery of the frit.

Figure 17D:
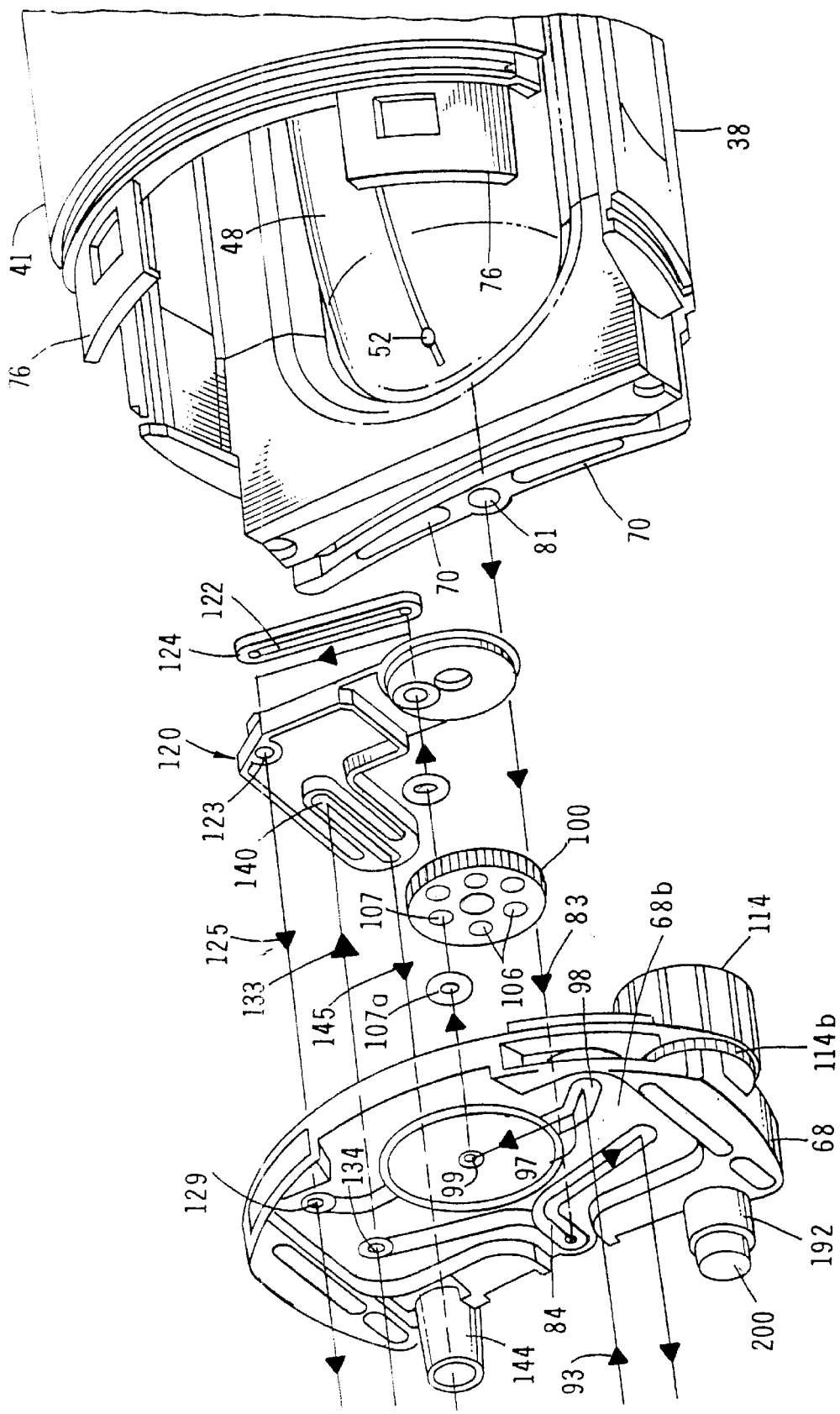
Figure 18:
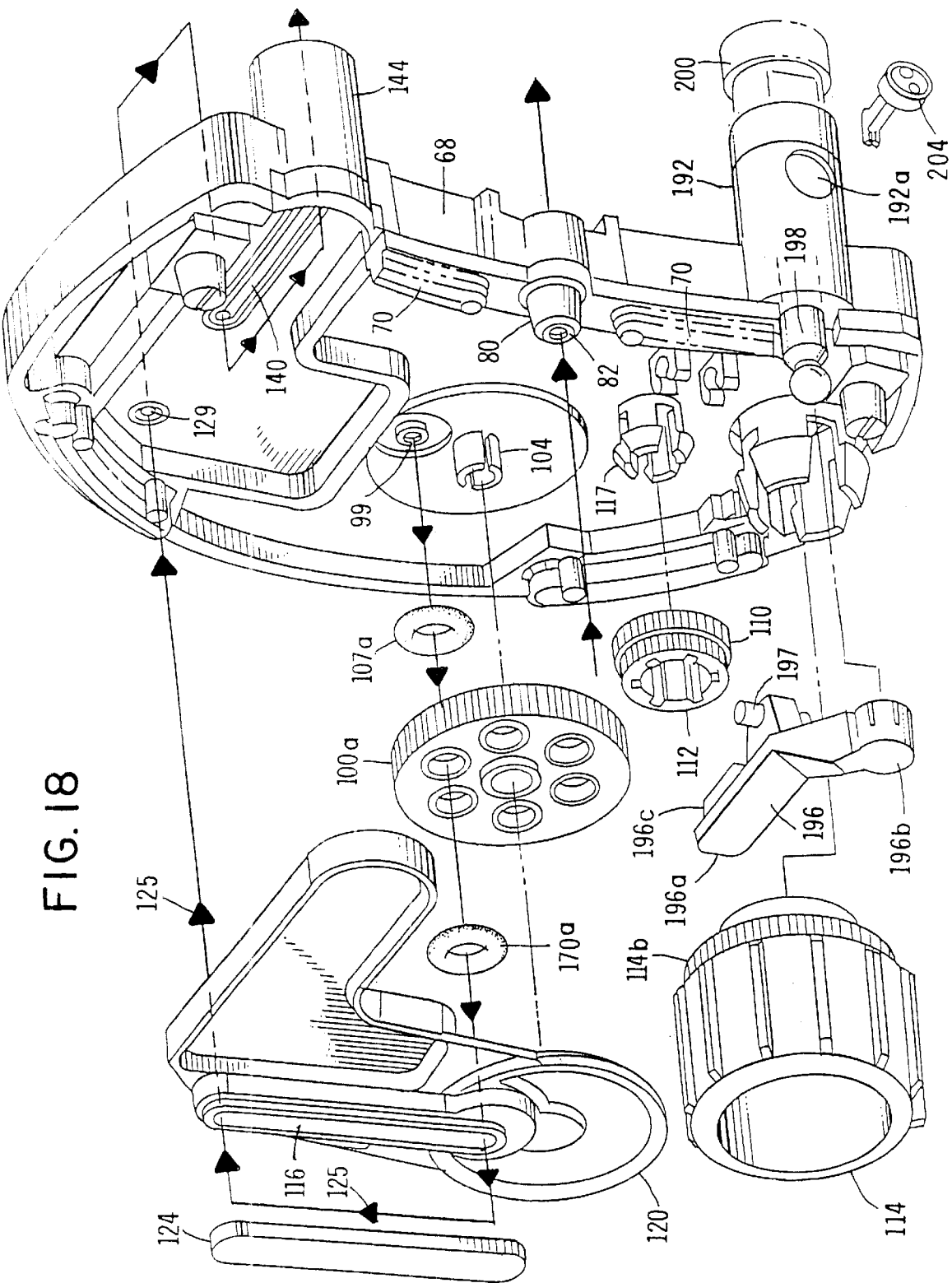
FIG. 18 is a greatly enlarged, generally perspective exploded rear view of the support means, the flow rate control means and the locking means of the invention, once again indicating with directional arrows the fluid flow path through the forward portion of the apparatus.
Figure 19:
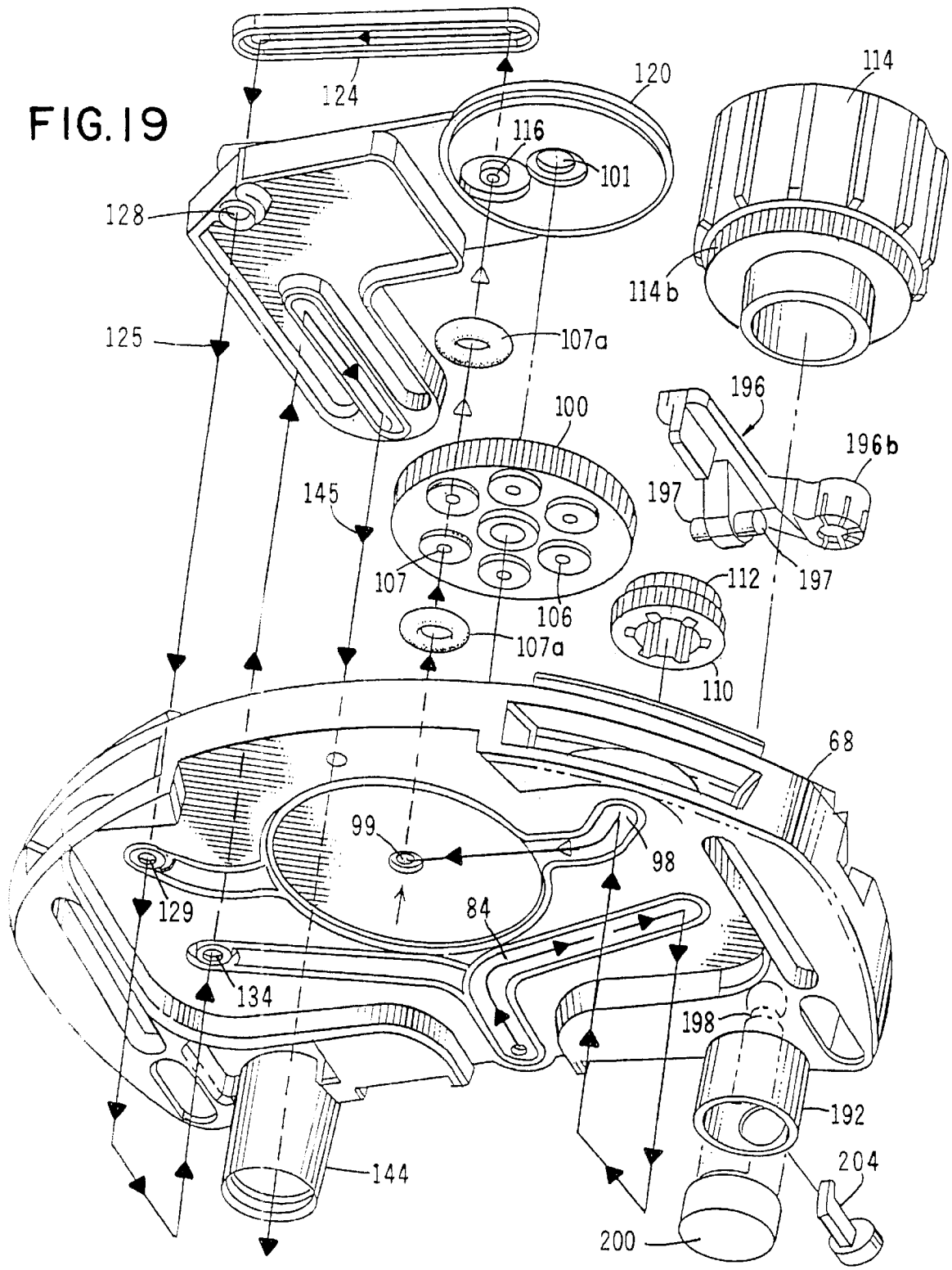
FIG. 19 is a greatly enlarged generally perspective exploded front view of the support means similar to FIG. 18 further illustrating the construction of the various operating systems of the apparatus of the invention and once again using directional arrows to indicate the fluid flow path through the forward portion of the apparatus.
Figure 21A:
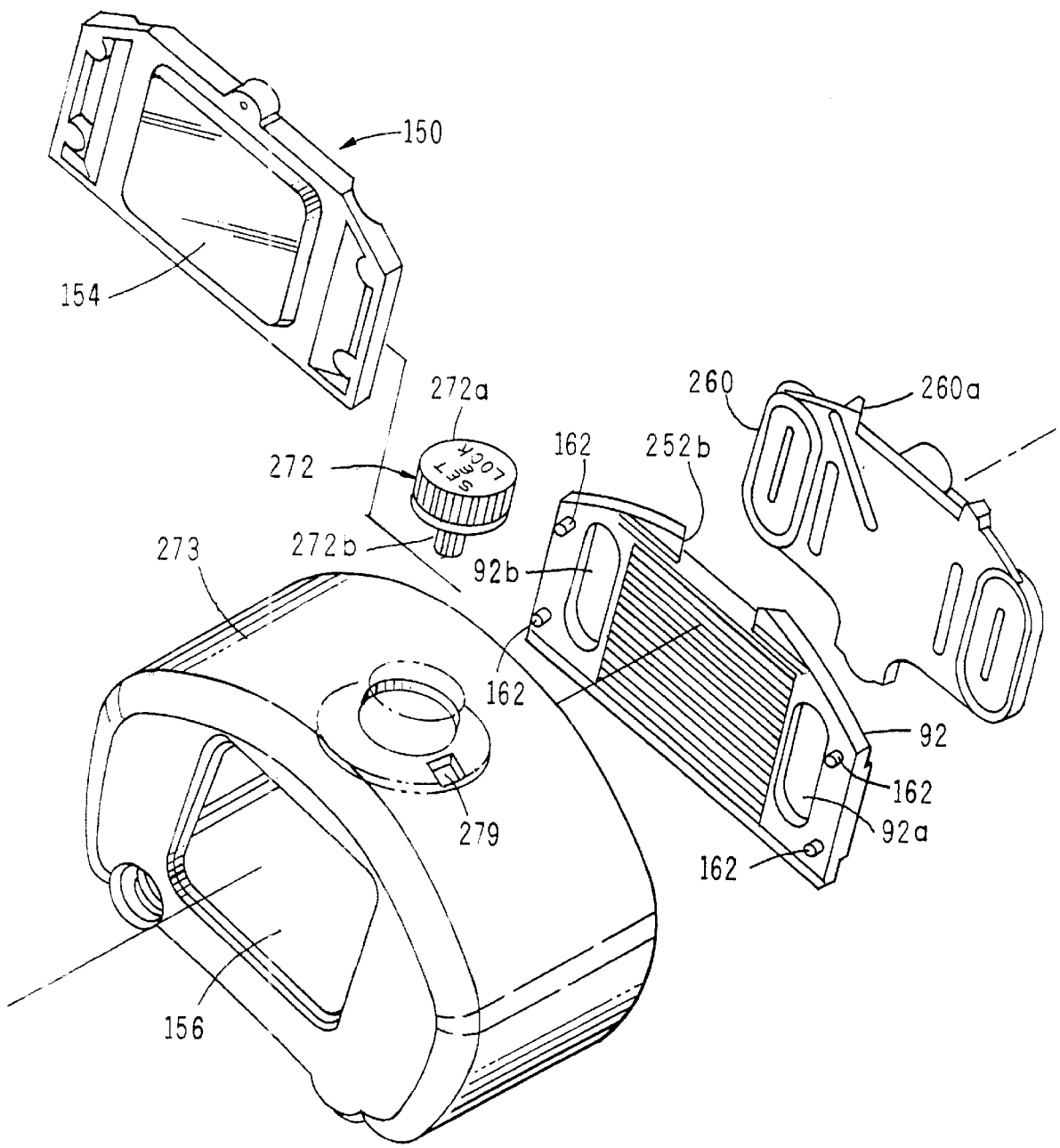
FIG. 21A is a generally perspective exploded view of the forward portion of the alternate form of the apparatus of the invention shown in FIG. 20 illustrating portions of the flow indicating means and of the locking means of this alternate embodiment.
Figure 21B:
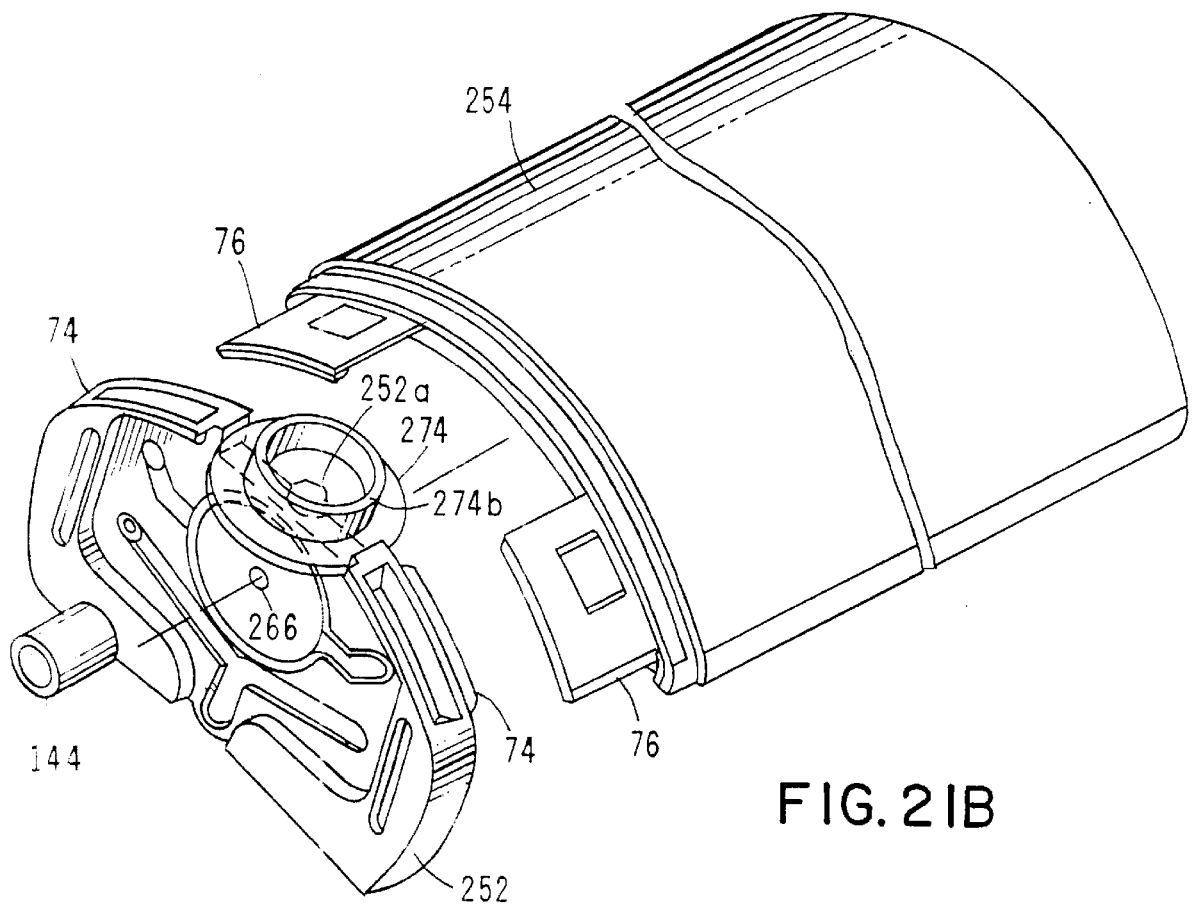
FIG. 21B is a generally perspective, exploded front view of the support means and a portion of the cover of the alternate form of the invention shown in FIG. 20.
Figure 21C:
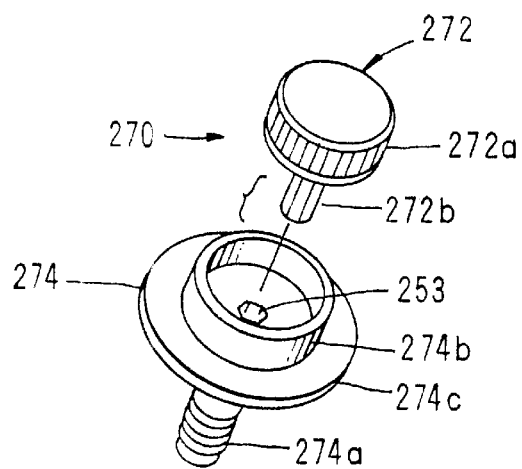
FIG. 21C is a generally perspective, exploded view of a portion of the adjustable flow rate control mechanism which is mounted proximate the top of the support means.

Considering once again the flow indicator means of the invention, it is to be observed that the fluid which is diverted back from boot 88 toward support 68 will flow in the direction of the arrow 93 of FIGS. 17C and 17D, through passageway 99 in support 68 and then through a selected rate control frit 107. After flowing through the selected rate control frit 107, the fluid will flow through a passageway 116 provided in a cover 120 which overlays control member 68. Next, the fluid will flow in the direction of the arrow 125 (FIGS. 17B, 17D, and 18), into passageway 122 formed in a second cover 124 which is connected to cover 120. Next the fluid will flow forwardly in the direction of arrow 125 through a passageway 129 formed in support 68 and through a passageway 127 formed in plate 90 (FIG. 17A). Next the fluid will impinge on a second elastomeric, distendable boot 130 (FIG. 17A) which also forms a part of the indicator means of the invention. The periphery 130a of indicator boot 130, which is of identical construction to boot 88, (see also FIG. 13A of U.S. Ser. No. 08/768,663) is clamped within an opening 92b formed in indicator base 92. After impinging on boot 130, the fluid will next flow back toward support 68 in the direction of arrow 133 (FIGS. 17A, 17B, and 17D), through orifice 131 formed in plate 90 and then, via an orifice 134 formed in support 68, into a passageway 140 which is formed by support 68 and plate 120. Upon entering passageway 140, the fluid will flow downwardly of the passageway and then into a tubular extension 144 formed on support 68 and finally in the direction of arrow 145 into a delivery line 146 via outlet port 76 (FIG. 17A).

It is to be observed that fluid flowing from reservoir 50 into passageways 54, 56, into passageway 82 and then on toward boot 88 is under a higher pressure than fluid flowing toward boot 130. This is because the pressure of the fluid flowing toward boot 130 has been reduced as a result of the fluid flowing through rate control frit 107. As will be discussed more fully in the paragraphs which follow, this result enables a determination of the various fluid flow operating conditions of the device namely normal fluid flow, fluid flow blockage or occlusion, and reservoir empty.

Turning particularly to FIGS. 17A, 17B, 17C and 17D, in addition to platform 92 and boots 88 and 130, the flow indicator means also comprises the boot clamping plate 90, a support or lens plate 150, and a hollow forward housing 152 within which the platform and the support plate are enclosed (FIG. 4). As seen in FIG. 4, a viewing lens 154 is viewable through an aperture 152a provided in forward housing 152. Disposed between platform 92 and lens plate 150 are first and second indicia-carrying means 155 shown here as a pair of closely adjacent, thin films. These films are virtually identical in construction and operation to films 306 and 308 of the embodiment described in incorporated by reference U.S. Ser. No 08/768,663 and, for a more complete understanding of these films, reference should be made to this application and particularly to FIGS. 12 and 13 and to the discussion of these figure drawings. The films are in intimate contact and are preferably constructed from a substantially transparent, flexible polymer material such as mylar. The downstream surface of the inferior or first film 306 is printed with three integrated symbols (see FIG. 12 of U.S. Ser. No. 08/768,663), which may comprise, by way of example, a blue circle, a green arrow, and a red X, each consisting of diagonal strips of color printed in an alternating pattern (blue, green, red, blue, green, red, and so on (see also FIGS. 1, 4B and 4C). The second film 308 serves as a "mask" over film 306 and is printed with a pattern of diagonal alternating clear and opaque strips that occur in approximately a 1:2 ratio. The printed ratio of the "mask" allows only one colored symbol to appear at a time when viewed through viewing lens 154. As in the embodiments described in U.S. Ser. No. 08/768,663, the inferior and superior films are provided at their opposite ends with apertures 160 which receive retention pins 162 provided on platform 92 (FIG. 17C) which permit attachment of the films to platform 92 in a manner such that the non-patterned portions of each film covers boot openings 92a and 92b provided proximate each end of platform 92 with the patterned portions of both the superior and inferior films being maintained in index. With this construction, each thin film is able to move in response to pressure exerted thereon by the elastomeric boots 88 and 130 in opposing directions parallel to the film plane with its range of motion limited to one axis in the film plane by edge guides 163 provided on platform 92 (FIG. 17C). As more fully described in U.S. Ser. No. 08/768,663, the films move, the visible symbol pattern will, of course, change due to the transverse displacement of the patterns imprinted thereon.

Figure 4B:
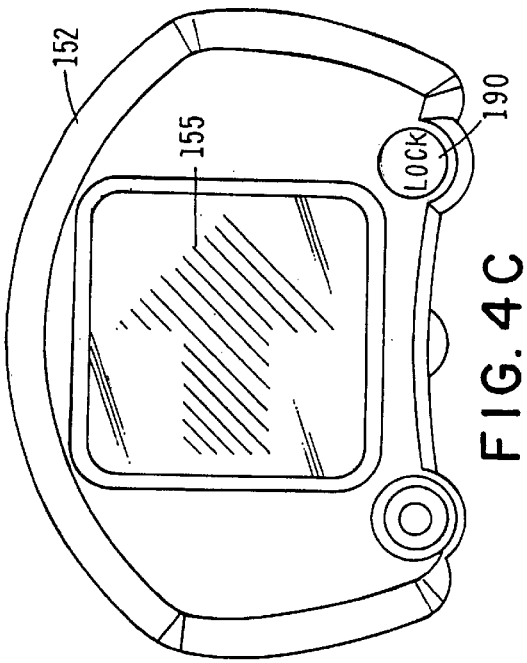
FIG. 4B is a diagrammatic front view of the apparatus illustrated in FIG. 4 showing one form of fluid flow indicia of the flow indicator means being displayed.
Figure 4C:
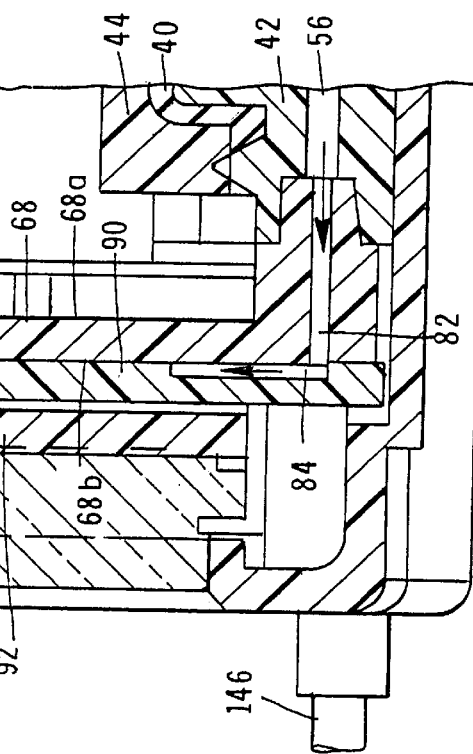
FIG. 4C is a diagrammatic front view similar to FIG. 4B, but showing another form of fluid flow indicia.

As is apparent from a study of FIGS. 13 and 13A of incorporated by reference U.S. Ser. No. 08/768,663, the central portions of both the first and second elastomeric actuator elements or boots 88 and 130 will be deflected outwardly toward plate 92 when the device is filled and primed, but not in a state of delivery or when there is a build up of fluid pressure during delivery that is caused by blockage of the delivery line downstream from boot 130. While boot 88 can be deflected by normal line pressure, boot 130 is deflected only by pressure buildup resulting from the downstream blockage. When both elastomeric boots 88 and 130 are deflected outwardly, both the superior and inferior films are displaced transversely to a second position revealing a second symbol, as for example, an X as viewed through the viewing aperture of the support plate (FIG. 4B). When fluid is flowing through the device, an indicia such as an arrow (FIG. 4C) is visible through the viewing window.

A third alignment of symbol patterns is visible when the device is in an unfilled state or when the delivery line is open, the reservoir is empty and fluid delivery to the patient has been completed. In this case, there is no fluid pressure in the line on either the upstream or the downstream side of the flow control means and thus both the first and second boots are in a non-deflected position. In this condition, the inferior and superior films are not transversely displaced and thus exhibit a third combination of patterns resulting in a third symbol as, for example, a circle being visible through the viewing aperture of the support plate. Boots 88 and 130 can be precisely tailored to deflect under various pressures thereby permitting great apparatus versatility. Reference should also be made to U.S. Ser. No. 08/432,221, which application was incorporated by reference in U.S. Ser. No. 08/738,663, for a further discussion of the construction and operation of the indicator means of the invention.

Operation

Considering now the method of using the apparatus of the invention for delivering medicinal fluid to a patient. Presuming that reservoir 50 was not filled at the factory, the first step in using the apparatus of the invention is to fill the reservoir using the fill means of the invention. As previously mentioned, the fill means here includes a fill subassembly 49 and also includes a fill line assembly 170 which comprises an elongated fill line 172 having at one end a luer connector 174 of the character adapted to be readily interconnected with a luer connector 176 which extends from a bottom of ullage substrate 42 and comprises a part of the fill assembly 49 (FIG. 4). Also forming a part of fill assembly 49 is valve means for controlling fluid flow from fill line 172 toward reservoir 50. In the present form of the invention, this valve means comprises a conventional type of umbrella valve 180 having a resiliently deformable skirt portion 182. When fill line 172 is appropriately interconnected with a source of the fluid to be infused into the patient, fluid will flow through line 172 into luer connector 176 and then into an internal chamber 184 within which umbrella valve 180 is disposed. Fluid flowing into chamber 184 under pressure will resiliently deform skirt portion 182 permitting fluid to flow into reservoir 50 via reservoir inlet port 186. As the fluid flows under pressure into reservoir 50, yieldably deformable membrane 40 will be deformed outwardly into the configuration shown in FIG. 4.

After reservoir 50 is appropriately filled, the next step in using the apparatus of the invention is for the physician or caregiver to set the adjustable fluid rate control mechanism of the invention to establish the desired rate of fluid flow from the apparatus toward the patient. However, before the adjustable flow rate control mechanisms can be operated, the physician must use the physicians key to unlock the novel rate control locking means of the invention. This locking means, which is generally designated in FIG. 1 by the numeral 190, comprises a generally cylindrically shaped hollow housing 192 which is closely received within an opening 193 formed in forward housing 152 and is also received within an opening 194 formed in support 68 (see FIGS. 2A and 15B). Also forming a part of the rate control locking means of the invention is a latch member 196 having a first end 196a and a second and 196b (FIG. 15A). As best seen by referring to FIG. 12A, latch member 196 is pivotally connected to support 68 by opposed hubs 197 for movement between first and second positions. Hubs 197 are pivotally mounted in cradles 197a formed on support 68 (FIG. 15B). When latch member 196 is in its flow rate selection position as shown in FIG. 6, end 196a is spaced apart from driver wheel 112 so as to permit free rotation thereof. However, when latch member 196 is in its locking, or first position, first end 196a operably engages drive wheel 112 so as to prevent its rotation and also the rotation of control member 100. More particularly, as shown in FIGS. 13 and 14, when latch member 196 is moved into a first locking position, an outwardly extending tongue 196c provided on the locking member is received within a pair of oppositely disposed, circumferentially spaced slots 112a formed in driven wheel 112 (FIG. 15A).

In order to move latch member 196 between its first and second positions, a latch operating assembly 195 which includes a latch operating member 198 is provided. Latch operating assembly 193 is telescopically received within hollow housing 192 and is movable against the urging of an operating member biasing means between a first extended position and a second depressed position. As best seen in FIG. 12A, latch operating member 198 includes a generally spherically shaped inboard extremity 198a which is in snug engagement with a cavity formed in second end 196b of latch 196. To move operating member 198 into its second, depressed position, an outwardly extending push button 200 is telescopically movable within hollow housing 192. The previously mentioned operating member biasing means is here provided in the form of a spring 199 which is carried by the shank portion of member 198 and functions to normally urge the latch member into the disengaged or rate selection position shown and FIG. 12A and, at the same time, to urge the push button 200 outwardly in the direction of arrow 201 into the extended position as shown in FIG. 12A.

Also forming a part of the rate control locking means of the invention is a key operated assembly 204 which is received within an opening 192a of hollow housing 192 (FIG. 15B). Assembly 204 is rotatable between a first locked position, shown in FIG. 5A, and a second unlocked position, shown in FIG. 5B (see also FIGS. 12A and 13). Referring particularly to FIGS. 15B and 16B it is to be noted a pusher member 205 which is disposed between push button 200 and member 198 is provided with a longitudinally extending slot 205a which terminates proximate one end in a transversely extending segment 205b. As best seen in FIG. 16B, key operated assembly 204 comprises a key operated member 206 which includes an apertured key receiving head 206a and a stem portion 206b which is closely receivable within slot 205a. Stem portion 206b terminates in a foot portion 207 which is receivable in segment 205b when the device is in the locked position shown in FIG. 14.

With the locking means of the invention in the locked configuration shown in FIG. 13, the physician or caregiver can insert the tines 210a formed on the physician's key 210 (see FIG. 1) into the openings 209 provided in head portion 206a of the key operated member 206. As illustrated in FIG. 1, tines 210a are provided at the extremity of a stem-like portion 210b of the physician's key so that upon rotation of the physician's key, operated member 206 can be rotated from the locked position shown in FIG. 14 to the unlocked position shown in FIG. 12a where the latch biasing means move it in the direction of the arrow 211 of FIG. 12A. This, in turn, will move push button 200 outwardly in the direction of the arrow 201. With the latch member 196 in the unlocked position shown in FIG. 12A, rotation of knob 114 will impart rotation to control member 100 via drive wheel 110. As the control member 100 is rotated, the various rate control frits 107 will sequentially move into index with fluid passageway 99. In this way, the particular control frit which will provide the desired rate of fluid flow outwardly of the device can be selected. Once the selection has been made button 200 can once again be depressed which will cause latch operating member 198 to pivot latch member 196 into the locked position shown in FIG. 13. With latch member 196 in this locked position, rotation of wheel 112 as well as drive wheel 110 is blocked thereby preventing further adjustment of the flow rate control. By turning the physician's key to the locked position shown in FIG. 5A the flow rate control mechanism will remain in its locking position until the physician's key is once again used to place the rate control mechanism in the rate selection configuration shown in FIG. 12A (see also FIGS. 5A and 5B).

Once the adjustable flow rate control mechanism has been set in the manner described in the preceding paragraphs, the delivery line 146 of the delivery means of the invention is interconnected with the outlet 144 of the device. In addition to the delivery line 146, the delivery means of the invention also includes a line clamp 214 which is of conventional construction and a gas vent and filter unit 216 which is also of a conventional construction well known to those skilled in the art.

Referring to FIG. 2B, it is to be noted that attachment means, generally designated by the numeral 218, are affixed to the lower surface of the base unit 38. This attachment means here comprises a generally rectangularly shaped foam pad 220 which includes lower adhesive covered surface 220a that enables the device to be removably affixed to a portion of the patient's body such as the patient's abdomen or the like. Alternatively, the device can be affixed to the patient's clothing or can be connected to a belt or the like.

Once the device is suitably affixed to the patient, the infusion cannula 221 of the cannula assembly 220 of the invention (FIG. 3) can be invasively interconnected with the patient. As best seen in FIG. 3, the cannula assembly 221 of the present form of the invention is of a conventional construction and is attached proximate the outboard end of delivery line 146. In addition to the infusion cannula, the assembly includes a butterfly assembly 222 which provides a convenient means for taping the assembly securely in position. With the cannula invasively interconnected with the patient, line clamp 214 can be open to permit fluid flow outwardly of the device through delivery line 146 and toward the patient. Fluid will flow toward the patient at the rate of flow selected by the physician at the time of setting the fluid flow rate control means of the invention. In the manner previously described, the fluid status of the device can be continuously monitored by observing the various flow symbols of the indicator means that appear through viewing window 154 of the apparatus.

Referring next to FIGS. 20 through 25, an alternate form of the invention is there illustrated and generally designated by the numeral 250. The apparatus of this latest form of the invention is quite similar to that shown in FIGS. 1 through 19 and also comprises four major cooperating subassemblies namely, a reservoir subassembly, an adjustable flow rate control subassembly, a flow indicator subassembly and fill means for filing the fluid reservoir of the reservoir subassembly. The reservoir subassembly, the flow indicator subassembly and the fill means are substantially identical in construction and operation to those earlier described and, accordingly, like numbers are used in FIGS. 20 through 25 to identify like components.

Considering first the reservoir subassembly shown in FIG. 4, this subassembly includes a base assembly which is identical to base assembly 38 and operates in precisely the same way. Therefore, this assembly is not shown in FIGS. 20 through 25.

With respect to the flow rate control means of this latest form of the invention, this means also here comprises an adjustable rate control mechanism which is carried by a support means 252 which is similar to support 68 but, in this instance, carries the flow rate control mechanism at a location proximate the upper portion of the support. As shown in FIG. 22B, support 252 also includes wing-like protuberances 70 which are received within spaced-apart, arcuate-shaped cavities formed in base assembly 38. Located proximate the upper edge of support 252 are arcuately, spaced-apart connector members 74 (FIG. 22B) which mate with arcuately spaced connectors 76 provided on cover 254 (FIG. 21 B) to enable secure interconnection of support 252 with the base assembly to form the hollow housing of the device.

Figure 22A:
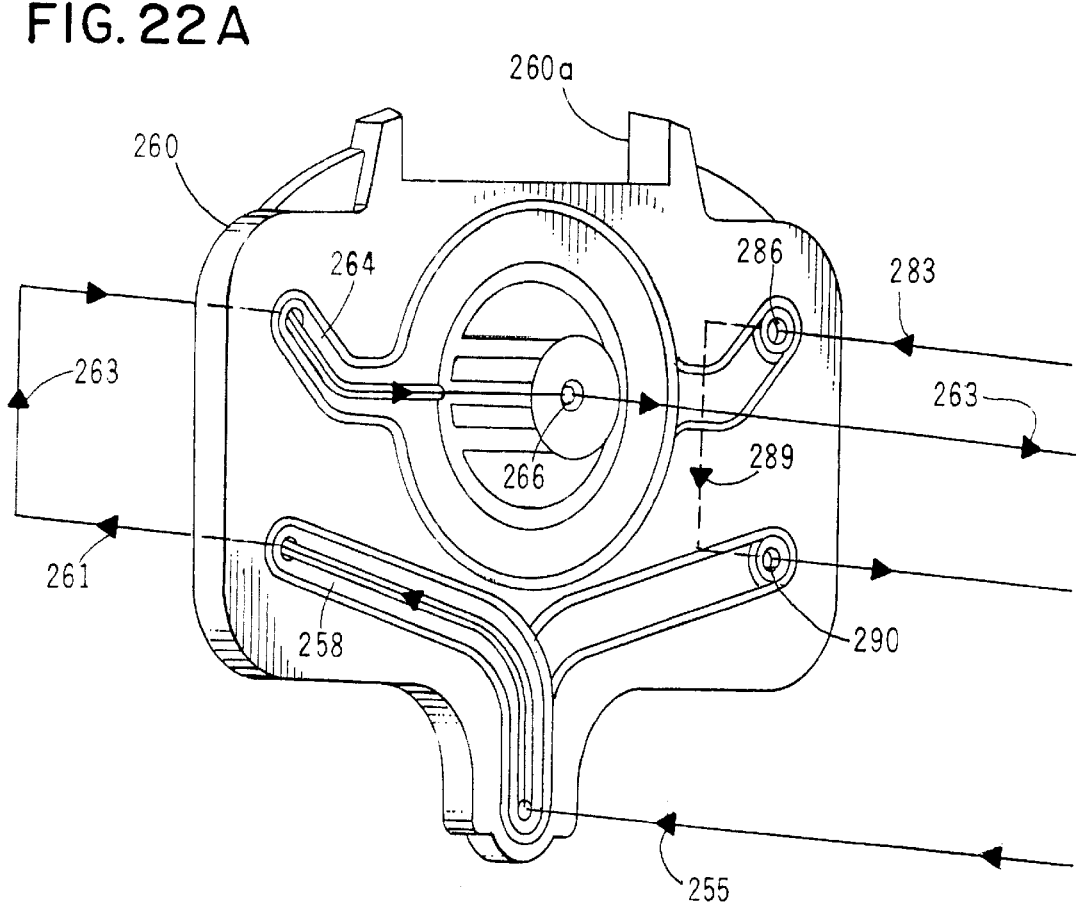

Turning to FIG. 22B it can be seen that support 252 of the support means also includes an outwardly extending, generally frustoconically shaped fluid inlet protuberance 80 which is closely receivable within a socket like cavity 81 formed in base member 42. When support 252 is mated with base assembly 38 and cover 254, a fluid inlet passageway 82 formed in protuberance 80 and is placed in fluid communication with reservoir 50 of the base assembly. As before, when fluid is forced through reservoir outlet 52 by the stored energy means, the fluid will flow through protuberance 80 in the direction of arrow 255 (FIG. 22B). The fluid will then flow into a passageway 258 formed in manifold plate 260 (FIGS. 22A and 22B) and finally in the direction of arrow 261 into a chamber formed in a distendable, elastomeric first boot of the flow indicator means of the invention which is identical in construction and operation to boot 88 of the earlier described embodiment. As before, when the fluid flowing from reservoir 50 impinges upon boot 88, flow will be diverted back in the direction of arrows 263 of FIG. 22A toward plate 260 and into a passageway 264 formed therein. When plate 260 is abutted against support 252, passageway 264 will cooperate with an aligned passageway formed in support 252 to form a closed flow passageway which is in communication with a control passageway 266 which extends through support 252 (FIGS. 22A and 22B) so that fluid will flow toward a flow rate control means mounted in support 252. This control means, which is of a different construction from the previously described control means, functions to control the rate of fluid flowing outwardly from the device.

The adjustable flow rate control means of this latest embodiment of the invention, comprises a control assembly 270 which is mounted within a vertically extending chamber 252*a* formed proximate the top support 252. As illustrated in FIGS. 20, 21C, 22B and 23, control assembly 270 includes knob-like selector member 272 which includes a head portion 272*a* and a shank portion 272*b*. Head portion 272*a* extends upwardly from the forward housing 273 of this latest form of the invention. Shank portion 272*b* of control selector 272 is receivable within the hollow stem portion 274*a* of a flow control assemblage 274 which is rotatably mounted within chamber 253. Control assemblage 274 also includes a cup like head portion 274*b* within which a portion of head portion 272*a* of selector member 272 is closely received. A flange 274*c*, which is disposed between stem portion 274*a* and cup like portion 274*b*, is closely receivable within notch-like openings 252*b* and 260*a* formed in support 252 and in manifold 260 (FIGS. 22A and 22B).

Circumferentially spaced about the lower extremity of stem portion 274*a* are the flow restrictor means of this latest embodiment. The flow restrictor means can take several forms such as orifices of various sizes or, as here shown, can comprise a plurality of porous rate control frits 277 of various porosity. Shank portion 272*b* of selector member 272 is provided with driving splines 272*c* which drivably engage control assemblage 274 to cause it to rotate within chamber 252*a* upon rotation of the knob-like head portion 272*a* which extends upwardly from the forward device housing in the manner shown in FIG. 20. As stem 274*a* rotates, frits 277 can be sequentially moved into index with control passageway 266. To prevent leakage between stem 274*a* and the wall of chamber 252*a*, a plurality of O-rings 278 are carried by stem 274*a* in a manner to sealably engage mating grooves 253 in the wall of chamber 252*a*. With this construction, by rotating knob 272*a*, a selected one of the plurality of rate control frits 277 can be moved into alignment with central passageway 266 of support 252 so that fluid from reservoir 50 will flow therethrough at a selected rate. Rate indicating indicia 274*d* are provided on flange 274*c* and are viewable through a viewing window 279 formed in the forward housing 273 (FIGS. 20 and 25).

Considering once again the flow indicator means of the invention, it is to be observed that fluid which is diverted back from boot 88 toward support 252, will flow in the direction of the arrow 263 of FIG. 22A through central passageway 266 and then through a selected rate control frit 277. After flowing through the selected rate control frit 277, the fluid will flow upwardly of hollow stem 274*a* and outwardly thereof through a passageway 280 provided therein (FIG. 22B). Next, the fluid will flow in the direction of the arrow 281, into passageway 282 formed in support 252. The fluid will then flow forwardly in the direction of arrow 283 through an orifice 286 formed in plate 260 where it will impinge in a second elastomeric, distendable boot which is also identical to boot 130 of the earlier described embodiment. After impinging on the boot, the fluid will next flow back toward support 252 in the direction of arrow 289 (FIGS. 22A and 22B) through orifice 290 formed in plate 260 and then, via an orifice formed in support 252, into a passageway 292 formed by cover 292*a* and support 252. Upon entering passageway 292, the fluid will flow downwardly of the passageway and then into a tubular extension 144 formed on support 252 and finally into the delivery line 146 of the apparatus via the outlet port.

As previously discussed, fluid flowing from reservoir 50 toward boot 88 is under a higher pressure than fluid flowing toward boot 130. This is because the pressure of the fluid flowing toward boot 130 has been reduced as a result of the fluid flowing through rate control frit 277. As before, this result enables determination by the substantially identical indicator assembly of the various fluid flow operating conditions of the device of this latest form of the invention, namely normal fluid flow, fluid flow blockage or occlusion, and reservoir empty.

Turning to FIGS. 26 through 37, still another form of the apparatus of the present form of the invention is there illustrated and generally designated by the numeral 300. The apparatus of this latest embodiment is similar to that shown in FIGS. 1 through 19 and also comprises four major cooperating subassemblies namely, a reservoir subassembly, an adjustable flow rate control subassembly, a flow indicator subassembly and fill means for filling the fluid reservoir of the reservoir subassembly. Because of the similarities between this latest form of the invention and those earlier described, like numerals are used in FIGS. 26 through 37 to identify like components.

Figure 27:
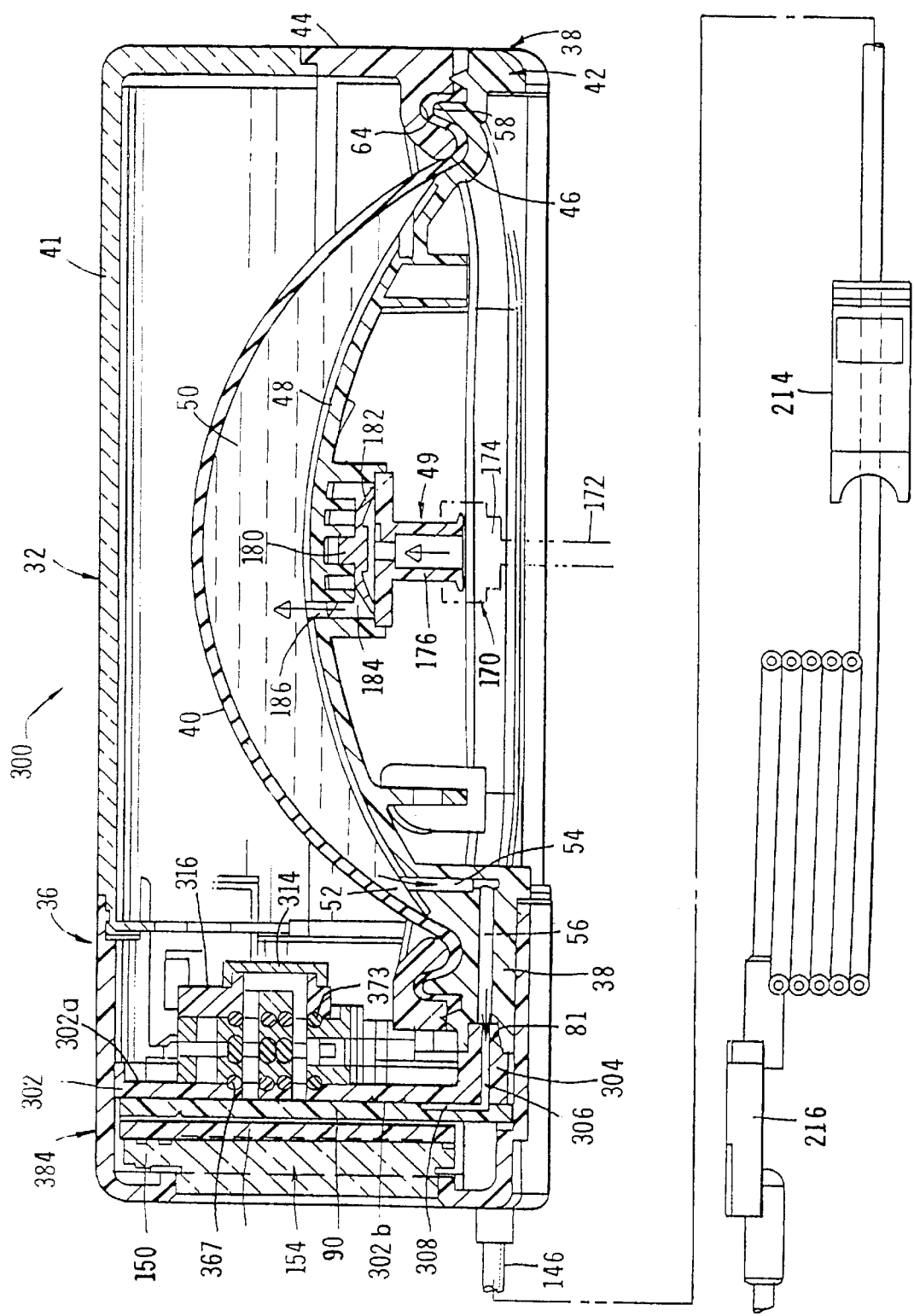
FIG. 27 is an enlarged, cross-sectional view taken along lines 27—27 of FIG. 26.
Figure 27A:
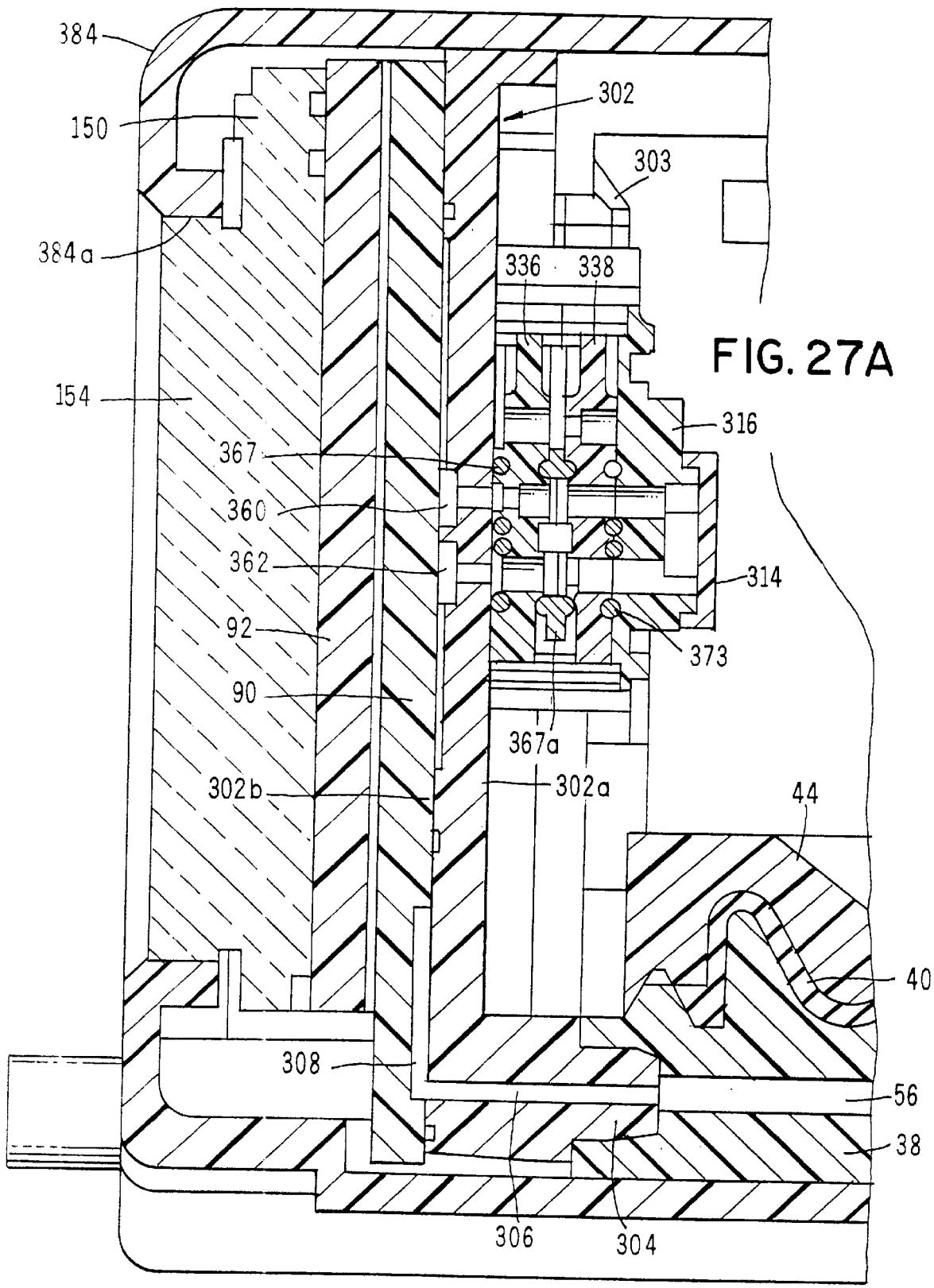
FIG. 27A is an enlarged, fragmentary, side-elevational view of the forward portion of the apparatus shown in FIG. 26 showing the adjustable flow rate control means.
Figure 27B:
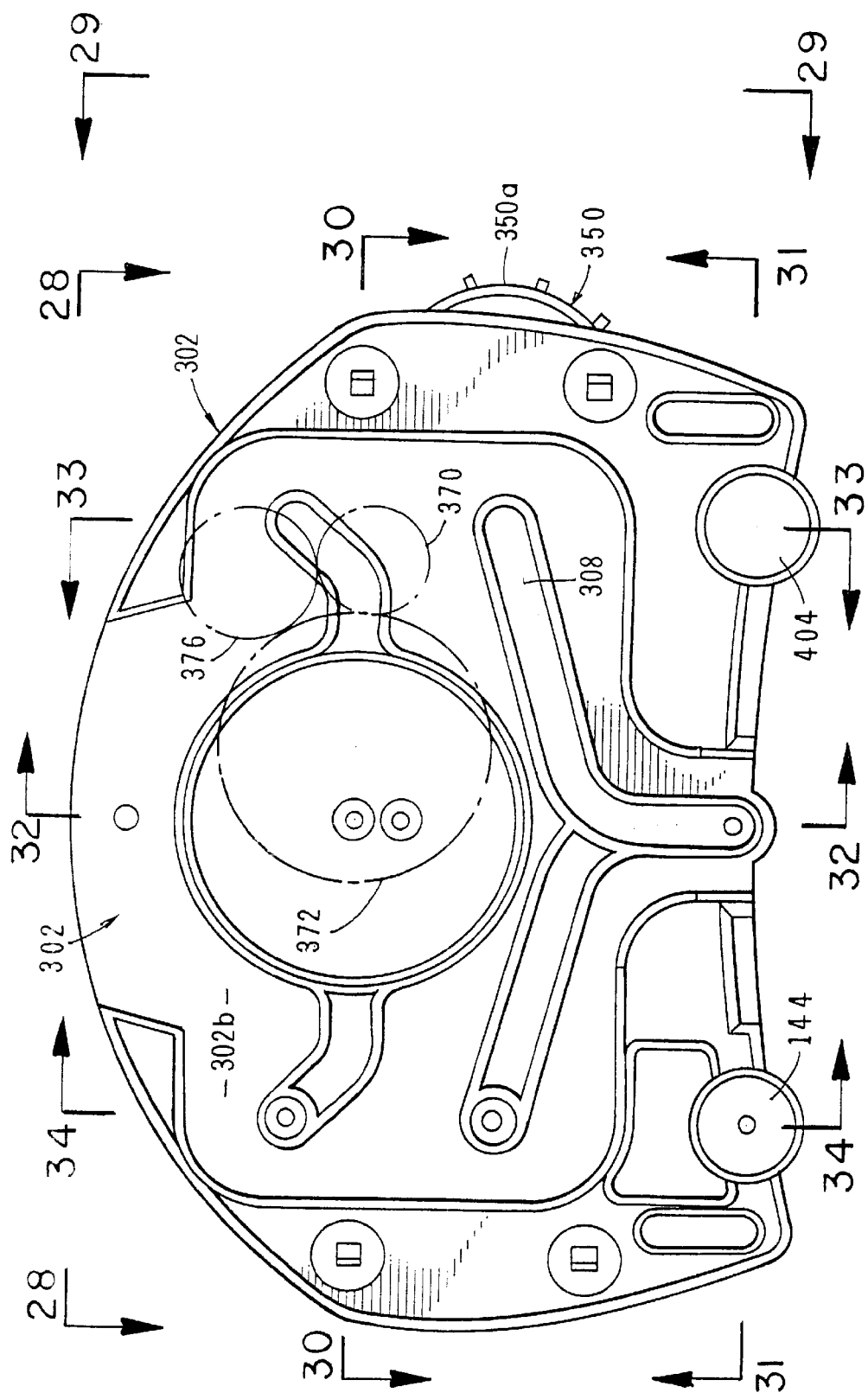
FIG. 27B is an enlarged front view of the support member of the apparatus of the invention.

Considering first the reservoir subassembly shown in FIG. 27, this subassembly is virtually identical in construction and operation to that shown in FIG. 4 and includes a base assembly 38, a stored energy source, shown here as a distendable membrane 40, and a cover 41 for enclosing the stored energy source. The base assembly includes an ullage substrate 42 and a membrane capture housing 44 having a bottom opening 46 which receives the distendable membrane engaging element or protuberance 48 of ullage substrate 42. As shown in FIG. 27 the ullage substrate, or base, 42 also includes a fill assembly 49, which is substantially identical in construction and operation to that previously described herein and illustrated in FIG. 3. The assembly of the ullage substrate, capture housing and cover is the same as previously described in connection with FIGS. 1 through 8.

The major difference between this latest embodiment of the invention and that shown in FIGS. 1 through 8 is the differently configured flow rate control means of the invention, for controlling the rate of fluid flow of fluid from the device. This means here comprises a pair of cooperating, adjustable rate control mechanisms which are carried by a support means shown here as comprising a deck-like support 302 which includes first and second faces 302a and 302b. Support 302 is connected to base assembly 38 and cover 41 in the manner best seen in FIG. 27. Located proximate the upper edge of support 302 are arcuately, spaced, apart connector members 303 (FIG. 36B) which mate with arcuately spaced connectors provided on cover 41 to enable secure interconnection of support 302 with the base assembly to form the hollow housing of the device.

As shown in FIG. 27, support 302 of the support means includes an outwardly extending, generally frustoconically shaped fluid inlet protuberance 304 which is closely receivable within a socket like cavity 81 formed in base member 42. When support 302 is mated with base assembly 38, a fluid inlet passageway 306 formed in protuberance 304 and is placed in fluid communication with reservoir 50 via passageways 54 and 56. With this construction, when fluid is forced through reservoir outlet 52 by the stored energy means, the fluid will flow into passageway 54, into passageway 56 and then into passageway 306 formed in protuberance 304. Next, the fluid will flow into a passageway 308 formed in face 302b of support 302 (FIG. 37) and finally into a chamber formed in a distendable, elastomeric first boot of the flow indicator means of the invention. The flow indicator means of this latest form of the invention is generally similar to that previously described and reference should be made to FIGS. 1 through 19 and the earlier discussion thereof for a more complete understanding of the construction and operation of the flow indicator means of this latest form of the invention. However, by way of summary, when the fluid flowing from reservoir 50 fills passageways 56 and 306 and impinges upon the first boot, flow will be diverted in the direction of arrows 310 of FIG. 37 rearwardly toward the novel flow rate control means, the character of which will presently be described. After flowing through the rate control means, the fluid will flow through a passageway 312 provided in a first cover 314 which overlays a first rate control housing 316. Next, the fluid will flow in the direction of the arrow 318 (FIG. 37), and into passageway 320. The fluid will then flow forwardly in the direction of arrow 324 through a passageway 326 formed in support 302. Next the fluid will impinge on a second elastomeric, distendable boot which also forms a part of the indicator means of the invention. After impinging on the second boot, the fluid will flow back toward cover 316 in the direction of arrows 330 through passageway 332 formed in cover 316 and then in the direction of arrow 332 into a delivery line 146 via the outlet port of the device (FIG. 27).

As before, the fluid flowing from reservoir 50 into passageway 56, into passageway 306 and then on toward the first boot is under a higher pressure than fluid flowing toward the second boot. This is because the pressure of the fluid flowing toward the second boot has been reduced as a result of the fluid flowing through the novel rate control means of the invention. As previously described, this enables a determination of the various fluid flow operating conditions of the device namely normal fluid flow, fluid flow blockage or occlusion, and reservoir empty (see the discussion on pages 21 through 34).

Figures 28, 29:
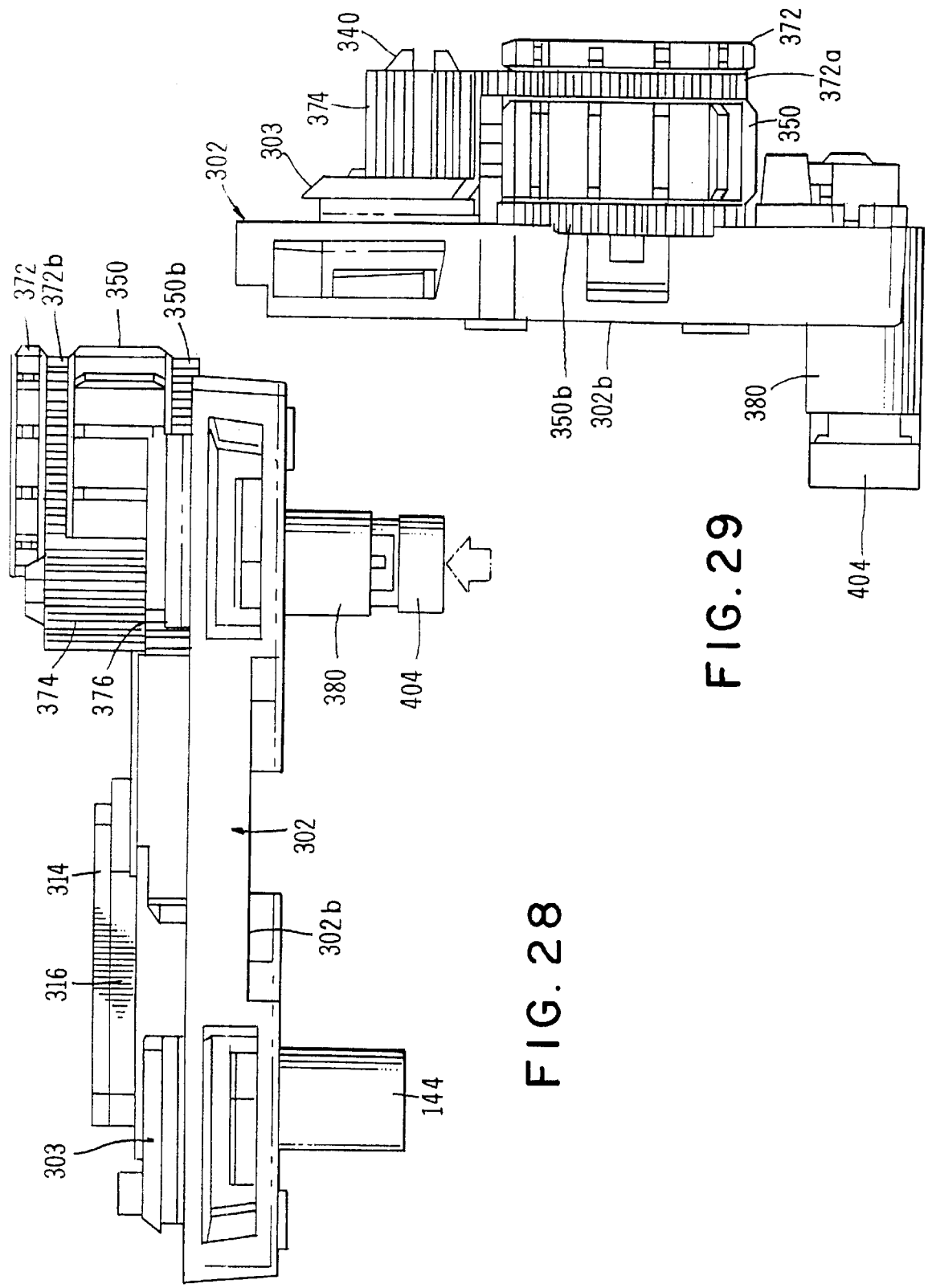
FIG. 28 is a view taken along lines 28—28 of FIG. 27B.
FIG. 29 is a view taken along lines 29—29 of FIG. 27B.
Figure 30:
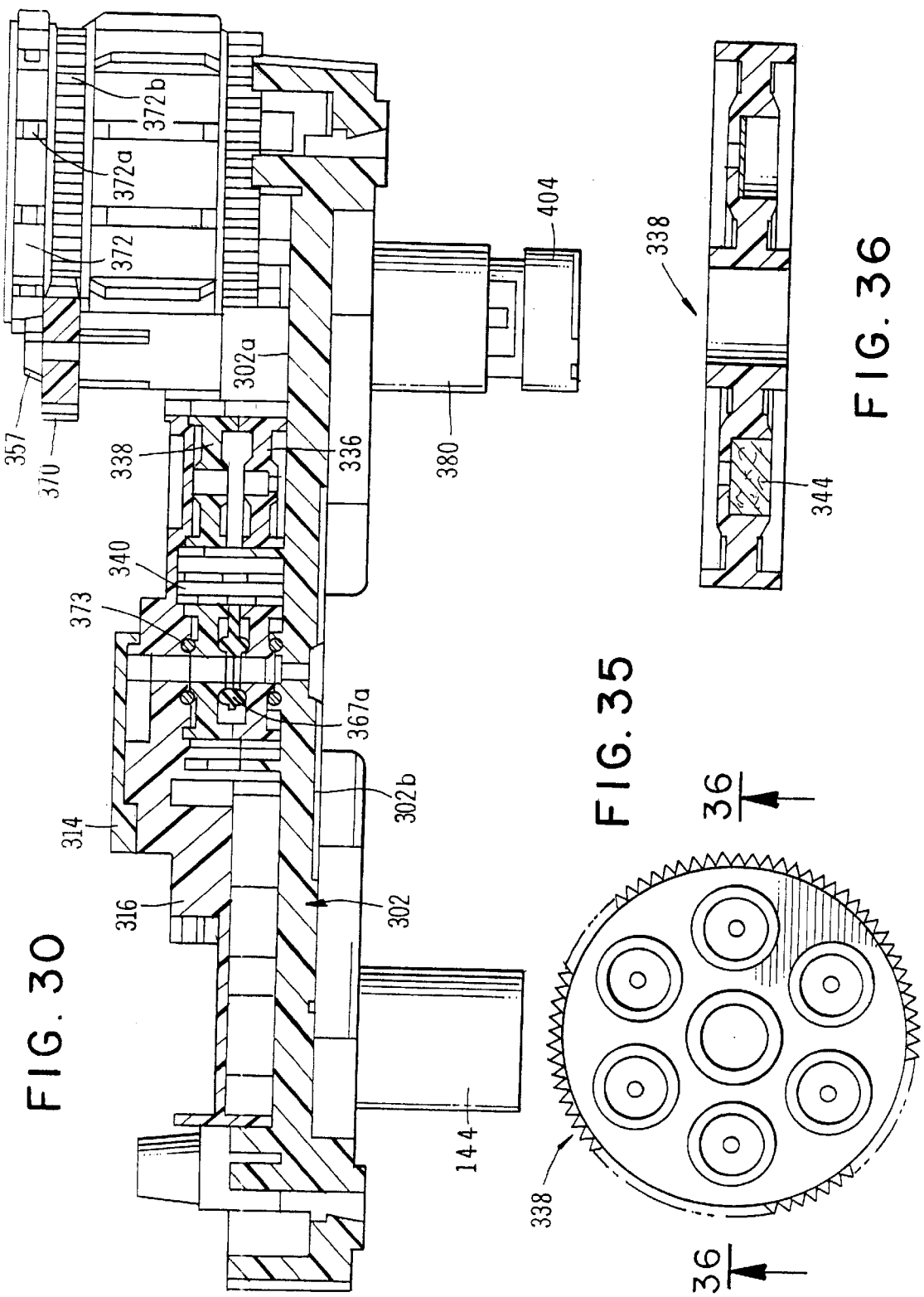
FIG. 30 is an enlarged, cross-sectional view taken along lines 30—30 of FIG. 27B.
Figures 31, 38:
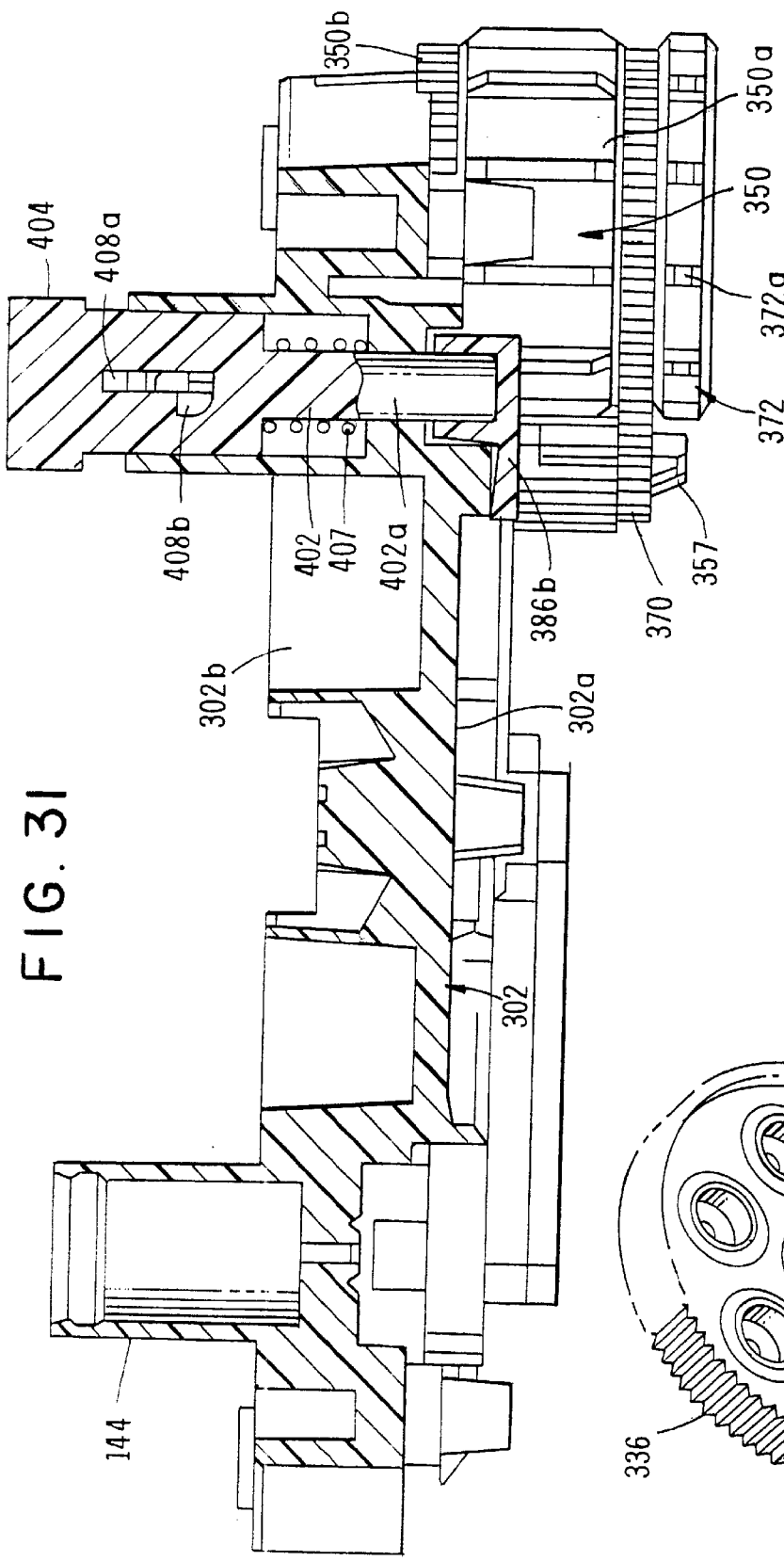
FIG. 31 is an enlarged, cross-sectional view taken along lines 31—31 of FIG. 27B.
FIG. 38 is a generally perspective, exploded view of one type of the flow rate control members of the invention.
Figure 36A:
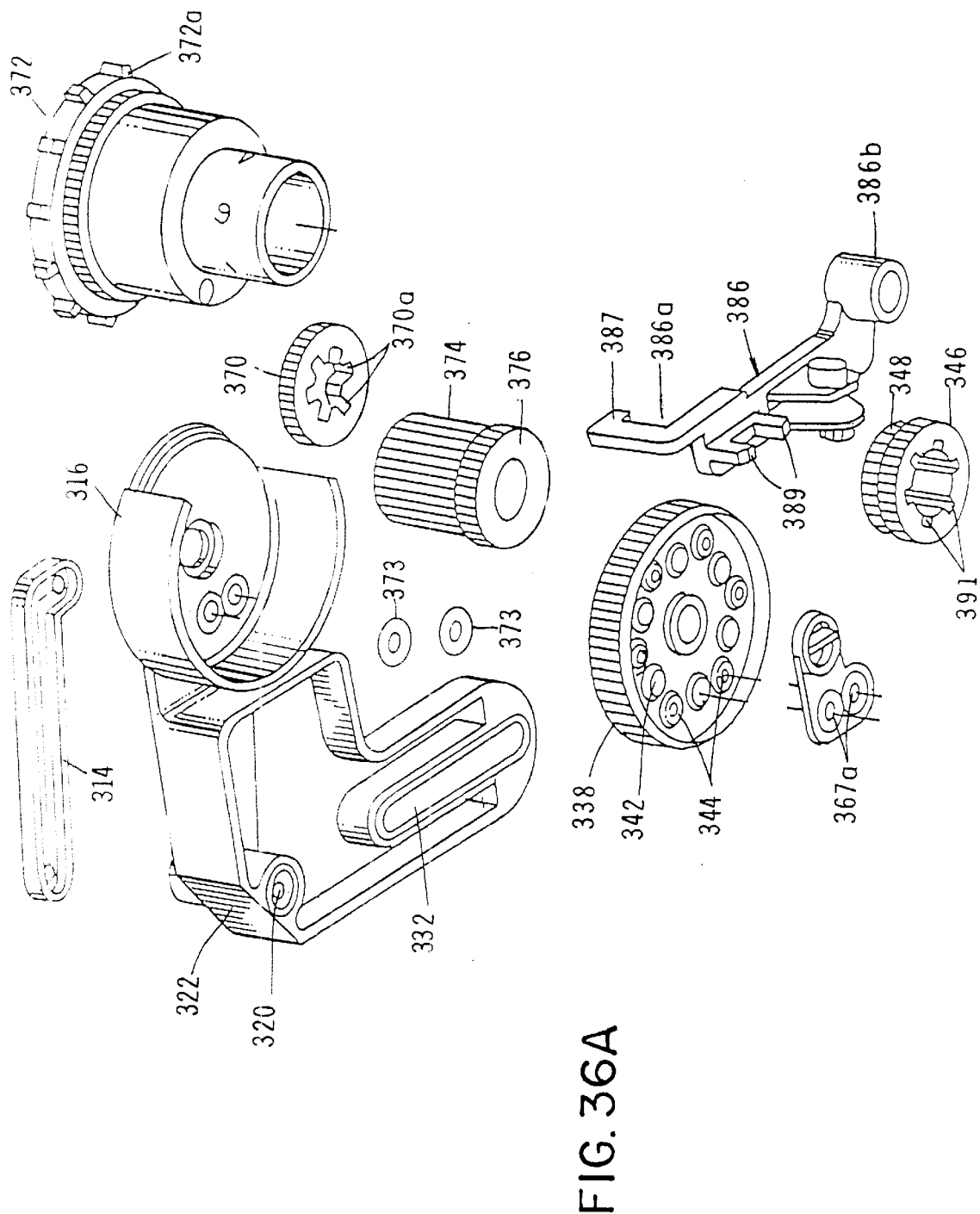
FIGS. 36A and 36B, when considered together, comprise an enlarged, generally perspective exploded front view of the support member and the adjustable flow rate control mechanisms of the apparatus of the invention.
Figure 36B:
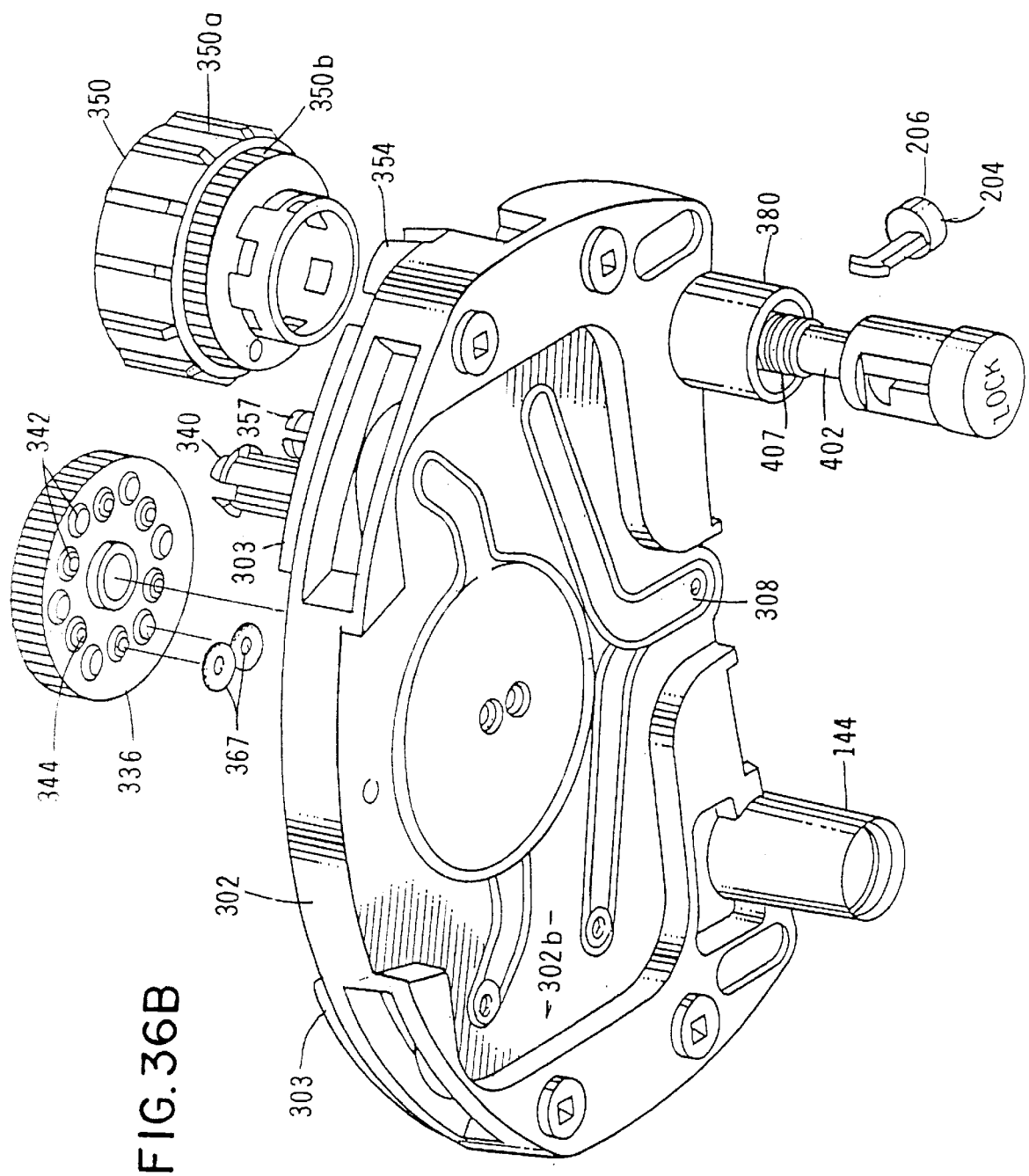
Figure 37:
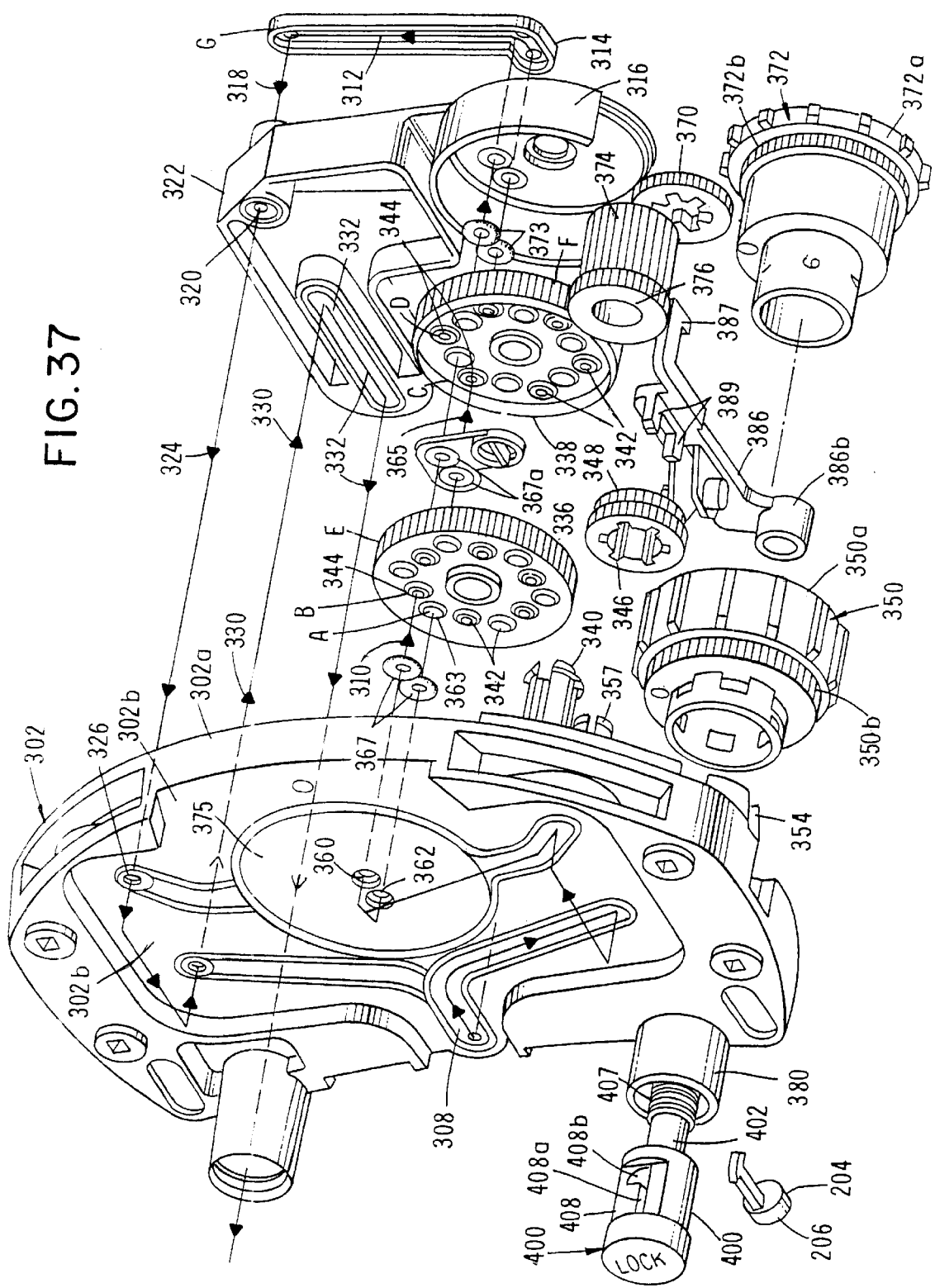
FIG. 37 is an enlarged, generally perspective exploded front view similar to FIGS. 36A and 36B but showing the fluid flow paths of the fluid flowing from the fluid reservoir toward the outlet of the device

Considering now the details of the novel flow rate control means of the invention, this means here comprises a pair of rate control members 336 and 338 each of which has teeth formed about its periphery (FIGS. 36A, 36B and 37). Each control member also has a central bore which receives a spindle 340 so that the member can be controllably rotated relative to face 302a of support 302 (FIG. 30). Circumferentially spaced about the central bore of each member is a plurality of apertures 342, each of which is adapted to carry a flow restrictor of the general character previously described. Once again the flow restrictors take the form of a porous rate control frit 344 (FIG. 11A). Member 336 is controllably rotated about spindle 340 by a driving member shown here as a toothed wheel 346. Connected to wheel 346 is a coaxially aligned, toothed wheel 348 which is driven by a finger engaging control knob 350 which, as shown in FIGS. 26 and 28 includes a peripheral portion 350a, a portion of which extends through an opening 352 formed in the forward portion of the device (FIG. 26). Knob 350 includes a lower toothed portion 350b which meshes with toothed wheel 348 so that rotation of knob 350 about spindle 354 (FIG. 37) will impart rotation to wheels 346 and 348 about a spindle 357 and will also impart rotation to control member 336. With this construction, by rotating knob 350 a selected one of the plurality of rate control frits 344 carried thereby can be moved into alignment with a first passageway 360 of support 302 so that fluid from reservoir 50 will flow therethrough. At the same time, fluid will flow from reservoir 50 through a second passageway 362 provided in support 302. Second passageway 362 is aligned with an open, non-frit carrying aperture 363 provided in member 336 so that a portion of the fluid will flow toward second control member 338 in the direction of arrow 365. Two pairs of elastomeric O-rings 367 and 367a sealably engage either the side of member 336 to prevent leakage about the periphery of the openings aligned with the fluid flow paths. O-rings 367a are carried by a generally "L" shaped member which is disposed between members 336 and 338 in the manner shown in FIG. 37.

As indicated in the drawings, member 338 is separately rotatable by a second driving mechanism which includes a toothed drive wheel 370. Drive wheel 370 is driven by a second finger engaging control knob 372 which also includes a peripheral portion 372a, a portion of which extends through opening 352 formed in the forward portion of the device (FIG. 26). Second knob 372 includes a toothed portion 372b which meshes with drive wheel 370 so that rotation of knob 372 about spindle 354 will impart rotation to a pair of coaxially aligned gear wheels 374 and 376 and will also impart rotation to second control member 338 which is operably associated with gear wheel 376. With this construction, by rotating knob 372 a selected one of the plurality of rate control frits carried by control member 338 can be moved into alignment with the fluid flow paths of fluid flowing from reservoir 50 in the direction of arrows 310 and 365. Once again, pairs of elastomeric O-rings 373 sealably engage member 338 to prevent leakage about the periphery of the apertures 342 formed therein.

Figure 39:
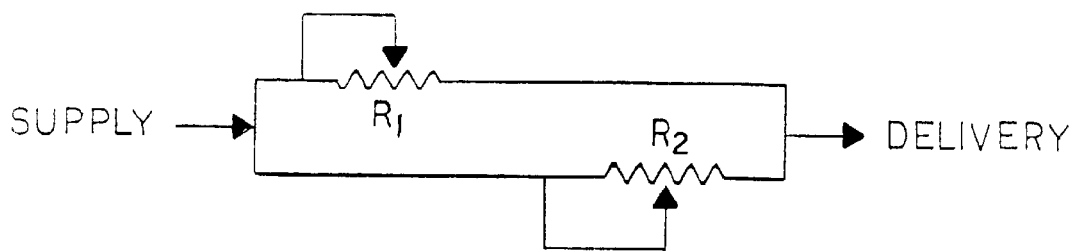
FIG. 39 is a generally diagrammatic view illustrating the fluid flow rate control adjustments.
Figure 40:
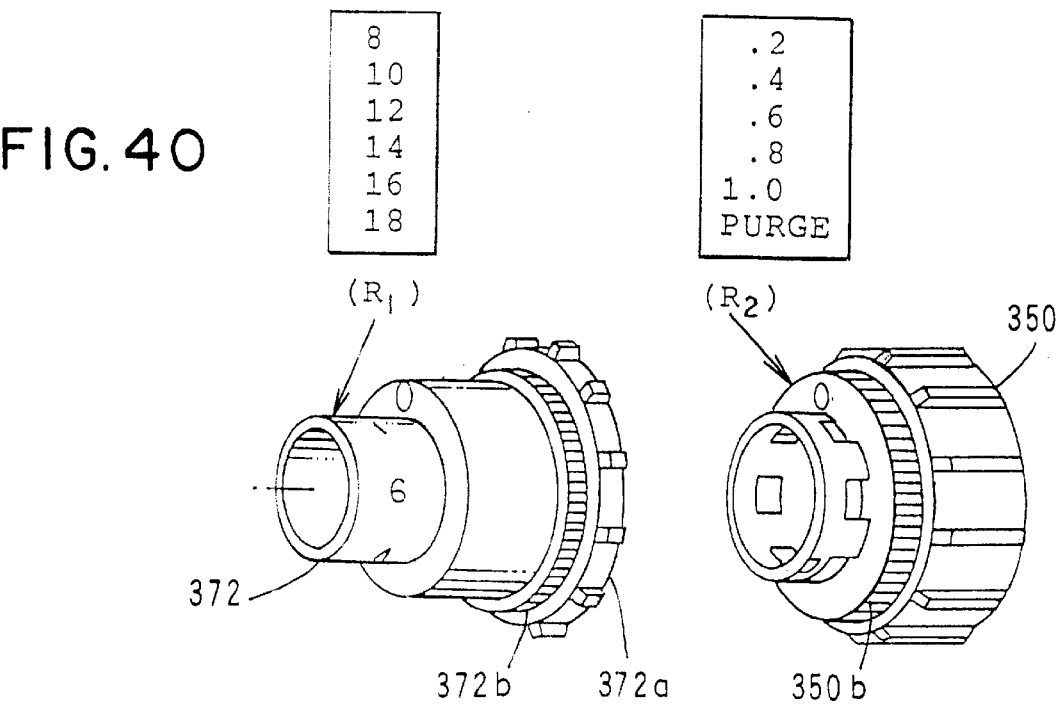
FIG. 40 is a generally diagrammatic view illustrating the character of the flow rate and indicator bands provided on the control knob.

Referring particularly to FIGS. 37, 39 and 40, with the construction there shown, it is apparent that through the use of the dual control members 336 and 338, a very precise fluid flow rate from the device can be achieved. More particularly, as indicated in FIG. 40, finger engaging wheel 350 can be provided with indicia such as 8, 10, 12, 14, 16 and 18 milliliter per hour bands. Rotation of knobs 350 will, therefore, accomplish the coarse rate control for fluid flowing along the flow control path indicated by the arrow 310 in FIG. 37. Similarly, rate control knob 372 can be provided with indicia in tenths of milliliter per hour such as 0.2, 0.4, 0.6, 0.8, and 1.0. These indicia indicate flow rate through the control members along the fluid flow path indicated by the arrow 365. As indicated in FIG. 37, aperture 342 designated by the letter "B" is provided with a porous flow control frit 344 which is represented in FIG. 39 by the resistance symbol R-1. This flow control frit would permit fluid flow toward the fluid delivery outlet of the device in coarse milliliter per hour increments such as 8, 10, 12, 14, 16, 18 and so forth. It is to be observed by referring to FIG. 37 that fluid flowing through rate control frit 344 will continue in the direction of the arrow 310 through an open aperture in control member 338 which is designated in FIG. 37 by the letter "D". Therefore, the coarsely controlled fluid will flow forwardly of the device into cover 314 in the manner shown in FIG. 37. On the other hand, fluid flowing into chamber 375, which is formed in support 302, will also flow through an open aperture provided in control member 336 which aperture is designated by the letter "A" in FIG. 37. The fluid flowing freely through open aperture "A" will flow onwardly toward control member 338 where it will flow through a porous rate control frit "C" which will limit fluid flow in one-tenth milliliter per hour increments as for example 0.2, 0.4, 0.6, 0.8 and so on. as indicated in FIG. 40. After the fluid flow through fine rate control frit "C", the fluid will flow toward cover 314 where it will mix with the fluid flowing along fluid flow path 310. The mixture of fluid then flowing toward the outlet of the device will be the sum of the fluids flowing along fluid flow paths 310 and 365. With this novel construction, precise fluid flow rates can be achieved. For example, if finger wheel 350 is rotated so that the numeral 14 appears in the window, rate control frit "B" will permit a fluid flow rate along fluid path 310 at 14 milliliters per hour. Similarly, if control wheel 372 is rotated so that the indicia 06 aligns with the viewing window, fluid flowing along flow path 365 will flow at a rate of 0.6 milliliters per hour in the direction toward cover 314. As is indicated by FIG. 40, the summation of these two fluid flows will move on to the delivery outlet port of the device at a rate of 14.6 milliliters per hour. With this novel arrangement, precise fluid flow rates to the tenth of a milliliter per hour flow rate can be achieved using the dual flow rate control mechanism of the invention shown in FIGS. 26 through 40.

In using the apparatus of the latest form of the invention, after reservoir 50 is appropriately filled, the physician or caregiver will set the course and fine adjustable rate control mechanisms of the invention in the manner just described. However, as before, in order to operate the adjustable flow rate control mechanisms, the physician must use the physicians key to unlock the novel rate control locking means of the invention. This locking means, which is generally similar to that previously described, comprises a generally cylindrically shaped hollow housing 380 which is closely received within an opening 382 formed in a forward housing 384 (FIG. 26). Also forming a part of the rate control locking means of the invention is a latch member 386 having a first end 386a and a second end 386b (FIG. 36A). As before latch member 386 is pivotally connected to support 302 for movement between first and second position. When latch member 386 is in its flow rate selection position, end 386a permits rotation of driver wheel 370 and also permits free rotation of driver wheels 346 and 348. However, when latch member 386 is in its locking, or first position, a tab 387 provided on first end 386a moves into a selected slot 370a provided in wheel 370 so as to prevent rotation of the wheel. Similarly, locking tabs 389 provided on latch 386 move into one of the circumferentially spaced slots 391 formed in wheels 346 and 348 thereby preventing rotation of these wheels.

In order to move latch member 386 between its first and second positions, a latch operating assembly 400 which includes a latch operating member 402 is provided (FIG. 37). Latch operating assembly 400 is telescopically received within hollow housing 380 and is movable against the urging of an operating member biasing means between a first extended position and a second depressed position. Latch operating member 402 includes an inboard extremity 402a (FIG. 33) which is in snug engagement with a cavity formed in second end 386b of latch 386. To move operating member 386 into its second, depressed position, an outwardly extending push button 404 is telescopically movable within hollow housing 380. The previously mentioned operating member biasing means is here provided in the form of a spring 407 which is carried by the shank portion of member 402 and functions to normally urge the latch member into the disengaged or rate selection position (FIG. 33). Spring 407 functions to continuously urge the push button 404 outward of housing 380 into an extended position to permit operation of the flow rate control means.

Also forming a part of the rate control locking means of this latest form of the invention is a key operated assembly 204 which is of similar construction and operation to that described in the embodiment shown in FIGS. 1 through 19. In this regard, a pusher member 408 which is disposed between push button 404 and member 402 is provided with a longitudinally extending slot 408a which terminates proximate one end in a transversely extending segment 408b. As before, key operated assembly 204 comprises a key operated member 206 which is of identical construction and operation to that previously described. Using the physician's key, member 206 can be rotated from the locked position to the unlocked position where the latch biasing means will move the latch member 386 into the unlocked position to permit rotation of knobs 350 and 372 which will, in turn, impart rotation to control members 336 and 338. As the control members are rotated, the various rate control frits can be sequentially move into index with the fluid passageways indicated by the arrows 310 and 365 of FIG. 37. In this way, the precise fluid flow outwardly of the device can be selected and the device can be interconnected with the patient in the manner previously described.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

What is claimed is:

1. A fluid delivery device for dispensing fluid, said device comprising:
    (a) a housing including a fixedly located fluid passageway defining a flow path having an inlet and an outlet;
    (b) a fluid reservoir disposed within said housing in fluid communication with said inlet of said fluid passageway;
    (c) stored energy means cooperatively associated with said fluid reservoir for urging fluid to flow therefrom toward said outlet of said fluid passageway; and
    (d) flow rate control means carried by said housing intermediate said fluid reservoir and said outlet for controlling of the rate of fluid flow toward said outlet of said fluid passageway, said flow rate control means comprising a control member having first and second spaced apart flow restrictors, said control member being rotatable from a first position wherein said first flow restrictor is aligned with said flow path to a second position wherein said second flow restrictor is aligned with said flow path.

2. The device as defined in claim 1 in which said control member comprises a generally planar member intersecting said flow path.

3. The device as defined in claim 1 in which each of said first and second flow restrictors comprises a porous frit.

4. The device as defined in claim 1 in which said flow rate control means comprises a control knob rotatably carried by said housing, said control knob being connected to said control member so as to impart rotation thereto upon rotation of said control knob.

5. The device as defined in claim 1 in which said housing includes a base and in which said stored energy means comprises a distendable member superimposed over said base, said member being distendable as a result of pressure imparted by the fluid to be dispensed to establish internal stresses, said stresses tending to move said member toward a less distended configuration.

6. The device as defined in claim 1 further including a fill means carried by said base for filling said fluid reservoir with the fluid to be dispensed.

* * * * *